US008809290B2

(12) United States Patent
Bot et al.

(10) Patent No.: US 8,809,290 B2
(45) Date of Patent: Aug. 19, 2014

(54) METHODS AND COMPOSITIONS TO GENERATE AND CONTROL THE EFFECTOR PROFILE OF T CELLS BY SIMULTANEOUS LOADING AND ACTIVATION OF SELECTED SUBSETS OF ANTIGEN PRESENTING CELLS

(75) Inventors: Adrian Bot, Beverly Hills, CA (US); Lilin Wang, San Diego, CA (US); Dan Joseph Smith, San Diego, CA (US); William Joseph Phillips, Jr., San Diego, CA (US); Luis A. Dellamary, San Marcos, CA (US)

(73) Assignee: Multicell Immunotherapeutics, Inc., Woonsocket, RI (US)

( * ) Notice: Subject to any disclaimer, the term of this patent is extended or adjusted under 35 U.S.C. 154(b) by 379 days.

(21) Appl. No.: 13/078,119

(22) Filed: Apr. 1, 2011

(65) Prior Publication Data

US 2011/0274705 A1  Nov. 10, 2011

Related U.S. Application Data

(63) Continuation of application No. 10/527,931, filed as application No. PCT/US03/30188 on Sep. 18, 2003, now abandoned.

(60) Provisional application No. 60/412,219, filed on Sep. 20, 2002.

(51) Int. Cl.
| | |
|---|---|
| *C12N 15/117* | (2010.01) |
| *A61K 39/12* | (2006.01) |
| *A61K 38/02* | (2006.01) |
| *A61K 31/713* | (2006.01) |
| *A61K 39/145* | (2006.01) |
| *A61K 39/39* | (2006.01) |
| *A61K 31/7105* | (2006.01) |
| *A61K 45/06* | (2006.01) |
| *A61K 39/21* | (2006.01) |
| *A61K 39/00* | (2006.01) |

(52) U.S. Cl.
CPC ........... *A61K 31/7105* (2013.01); *A61K 31/713* (2013.01); *A61K 39/145* (2013.01); *C12N 2740/16034* (2013.01); *A61K 2039/55561* (2013.01); *A61K 39/0011* (2013.01); *A61K 2039/55511* (2013.01); *A61K 2039/53* (2013.01); *A61K 2039/5252* (2013.01); *A61K 39/39* (2013.01); *A61K 2039/57* (2013.01); *A61K 45/06* (2013.01); *C12N 2710/20034* (2013.01); *A61K 2039/544* (2013.01); *A61K 39/12* (2013.01); *A61K 39/21* (2013.01); *C12N 2760/16134* (2013.01)
USPC ............... 514/44 R; 424/192.1; 424/206.1; 424/278.1

(58) Field of Classification Search
CPC ............ A61K 31/713; A61K 31/7105; A61K 2300/00; A61K 39/12; A61K 2039/57; C12N 2760/16134
USPC .................. 514/44 R; 424/92.1, 206.1, 278.1
See application file for complete search history.

(56) References Cited

U.S. PATENT DOCUMENTS

| | | | |
|---|---|---|---|
| 3,906,092 A | * | 9/1975 | Hilleman et al. .......... 424/209.1 |
| 5,474,771 A | | 12/1995 | Lederman et al. |
| 5,508,386 A | | 4/1996 | Zanetti et al. |
| 5,583,202 A | | 12/1996 | Zanetti |
| 5,593,973 A | | 1/1997 | Carter |
| 5,612,035 A | | 3/1997 | Howell et al. |
| 5,663,153 A | | 9/1997 | Hutcherson et al. |
| 5,683,986 A | | 11/1997 | Carter |
| 5,698,679 A | | 12/1997 | Nemazee |
| 5,736,524 A | | 4/1998 | Content et al. |
| 5,763,417 A | | 6/1998 | Einck |
| 5,906,980 A | | 5/1999 | Carter |
| 5,958,457 A | | 9/1999 | Santiago et al. |
| 5,696,109 A | | 10/1999 | Bona et al. |
| 5,969,109 A | * | 10/1999 | Bona et al. ................. 530/387.3 |
| 5,976,800 A | | 11/1999 | Lau et al. |
| 5,998,366 A | | 12/1999 | Tobin et al. |
| 6,194,388 B1 | | 2/2001 | Krieg et al. |
| 6,207,646 B1 | | 3/2001 | Krieg et al. |
| 6,239,116 B1 | | 5/2001 | Krieg et al. |
| 6,245,894 B1 | | 6/2001 | Matsushima et al. |
| 6,294,654 B1 | | 9/2001 | Bogen et al. |

(Continued)

FOREIGN PATENT DOCUMENTS

| | | |
|---|---|---|
| EP | 1 074 617 A2 | 2/2001 |
| WO | WO 94/28026 | * 12/1994 |

(Continued)

OTHER PUBLICATIONS

Zaghouani et al. (1993) Eur. J. Immunol., vol. 23, 2746-2750.*

(Continued)

*Primary Examiner* — Anne Marie S Wehbe
(74) *Attorney, Agent, or Firm* — David J. Wilson; Kevin M. Farrell

(57) ABSTRACT

The present invention is directed to novel compositions that cause effective redirection of class I-immunity to Tc1 effectors, that take advantage of the unexpected loading of MHC I by peptide within IgG backbone combined with appropriate instruction of antigen presenting cells. Such compositions are able to transform a seemingly ineffective therapeutics into a highly effective one, associated with generation of class I-restricted cytolytic cells and IFN-γ, IL-2 producing T cells, further associated with protection against a highly virulent microbe or recovery from malignant tumoral process.

13 Claims, 63 Drawing Sheets

(56) References Cited

U.S. PATENT DOCUMENTS

| | | | |
|---|---|---|---|
| 6,339,068 | B1 | 1/2002 | Krieg et al. |
| 6,727,030 | B2 | 4/2002 | Krieg et al. |
| 6,406,705 | B1 | 6/2002 | Krieg et al. |
| 6,429,199 | B1 | 8/2002 | Krieg et al. |
| 6,458,934 | B1 | 10/2002 | Hong et al. |
| 6,506,559 | B1 | 1/2003 | Driver et al. |
| 6,514,948 | B1 | 2/2003 | Raz et al. |
| 6,653,292 | B1 | 11/2003 | Krieg et al. |
| 6,821,957 | B2 | 11/2004 | Krieg et al. |
| 6,861,408 | B2 * | 3/2005 | Nicolette ............... 514/19.3 |
| 7,252,829 | B1 | 8/2007 | Sette et al. |
| 7,981,673 | B2 | 7/2011 | Adams et al. |
| 8,076,460 | B2 | 12/2011 | Matsumoto et al. |
| 2002/0142974 | A1* | 10/2002 | Kohn et al. ............... 514/44 |
| 2004/0052820 | A1 | 3/2004 | Bolognesi et al. |
| 2004/0234531 | A1 | 11/2004 | Casares et al. |
| 2005/0044588 | A1 | 2/2005 | Langridge et al. |
| 2005/0074449 | A1 | 4/2005 | Bot et al. |
| 2005/0222060 | A1* | 10/2005 | Bot et al. ............... 514/44 |
| 2006/0110746 | A1 | 5/2006 | Andre et al. |
| 2006/0147456 | A1 | 7/2006 | Lebecque et al. |
| 2006/0172959 | A1 | 8/2006 | Smith et al. |

FOREIGN PATENT DOCUMENTS

| | | | |
|---|---|---|---|
| WO | WO 96/19658 | A1 | 6/1996 |
| WO | 96/22377 | A | 7/1996 |
| WO | WO98/36087 | | 8/1998 |
| WO | 99/54484 | A | 10/1999 |
| WO | 01/36641 | A | 5/2001 |
| WO | 01/93902 | A | 12/2001 |
| WO | 03/078595 | A2 | 9/2003 |
| WO | WO03/078595 | A2 | 9/2003 |
| WO | 2004/027049 | A2 | 4/2004 |
| WO | WO2004/027049 | A2 | 4/2004 |

OTHER PUBLICATIONS

Tagliani et al—"Selection of an Antibody Library Identifies a Pathway to Induce Immunity by Targeting CD36 on Steady-State CD8α+ Dendritic Cells." The Journal of Immunology. 2008. vol. 180, pp. 3201-3209.

Bot et al—"Immunologic Control of Tumors by In Vivo Fc(gamma) Receptor-Targeted Antigen Loading in Conjunction with Double-Stranded RNA-Mediated Immune Modulation." Journal of Immunology (Baltimore, Md. : 1950). Feb. 2006. vol. 176, pp. 1363-1374.

Phillips et al—"Recombinant immunoglobulin-based epitope delivery: A novel class of autoimmune regulators." International Reviews of Immunology. Sep. 2005. vol. 24 (5-6), pp. 501-517.

Carvey et al—"Intra-parenchymal injection of tumor necrosis factor-α and interleukin 1-β produces dopamine neuron loss in the rat." Journal of Neural Transmission. May 2005. vol. 112, pp. 601-612.

Jeng et al—"Roles of keratinocyte inflammation in oral cancer: regulating the prostaglandin E2, interleukin-6 and TNF-α production of oral epithelial cells by areca nut extract and arecoline." Aug. 2003. Carcinogenesis vol. 24, No. B pp. 1301-1315.

Coburn et al., "siRNAs: a new wave of RNA-based therapeutics." Journal of Antimicrobial Chemotherapy. Apr. 2003. vol. 51, pp. 753-756.

Agami, "RNAi and related mechanisms and their potential use for therapy." Current Opinion in Chemical Biology, Dec. 2002. vol. 6 (6), pp. 829-834.

Bonifaz et al—"Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance." Journal of Experimental Medicine. Dec. 16, 2002. vol. 196, No. 12, pp. 1627-1638.

Scanlan et al—"Cancer/testis antigens: an expanding family of targets for cancer immunotherapy." Immunological Reviews. Oct. 2002. vol. 188, pp. 22-32.

Melo et al - "Gene transfer if Ig-fusion proteins into B cells prevents and treats autoimmune diseases." Journal of Immunology. May 1, 2002. vol. 168 (9), pp. 4788-4795.

Chirila et al—"The use of synthetic polymers for delivery of therapeutic antisense oligodeoxynudeotides." Biomaterials. Jan. 2002. vol. 23 (2), pp. 321-342.

Fujita et al—"Overexpression of tumor necrosis factor-α produces an increase in lung volumes and pulmonary hypertension." American journal of physiology. Lung cellular and molecular physiology. Jan. 2001. vol. 280, Issue 1, pp. L39-L49.

Elbashir et al., "RNA interference is mediated by 21- and 22-nucleotide RNAs." Genes & Development. Jan. 2001. vol. 15 (2), pp. 188-200.

Svoboda et al., "Selective reduction of dormant maternal mRNAs in mouse oocytes by RNA interference." Development (Cambridge, England). Oct. 2000. vol. 127 (19), pp. 4147-4156.

Jen et al., "Suppression of gene expression by targeted disruption of messenger RNA: Available options and current strategies." Stem Cells. Sep. 2000. vol. 18 (5), pp. 307-319.

Oates et al., "Too much interference: Injection of double-stranded RNA has nonspecific effects in the zebrafish embryo." Development Biology. Aug. 2000. vol. 224, pp. 20-28.

Green et al., "Antisense Oligonucleotides: an evolving technology for the modulation of gene expression in human disease." Journal of the American College of Surgeons. Jul. 2000. vol. 191, pp. 93-105.

Wianny et al., "Specific interference with gene function by double-stranded RNA in early mouse development" Nature Cell Biology. Feb. 2000. vol. 2 (2), pp. 70-75.

Romero et al—"Grb2 and Its Apoptotic Isoform Grb3-3 Associated with Heterogeneous Nuclear Ribonucleoprotein C, and These Interactions Are Modulated by Poly(U) RNA." The Journal of Biological Chemistry. Mar. 27, 1998. vol. 273, No. 13, pp. 7776-7781.

Branch, "A good antisense molecule is hard to find." Trends in Biochemical Sciences. Feb. 1998. vol. 23 (2), pp. 45-50.

Khan et al—"Polyadenylic-polyuridylic acid enhances the natural cell-mediated cytotoxicity in patients with breast cancer undergoing mastectomy." Surgery. Sep. 1995. vol. 118 pp. 531-538.

Khan et al—"Synthetic polyribonucleotides: current role and potential use in oncological practice." Apr. 1995, European Journal of Surgical Oncology. vol. 21, pp. 224-227.

Johnson—"Molecular Adjuvants and Immunomodulators: New Approaches to Immunization." Clinical Microbology Reviews. Jul. 1994. pp. 277-289.

Brumeanu et al—"Efficient loading of identical viral peptide onto class II molecules by antigenized immunoglobulin and influenza virus." Journal of Experimental Medicine, Nov. 1, 1993. vol. 178, pp. 1795-1799.

Manetti et al—"Natural Killer Cell Stimulatory Factor (Interleukin 12 [IL-12]) Induces T Helper Type 1 (Th1)-specific Immune Responses and Inhibits the Development of IL-4-producing Th Cells," Journal of Experimental Medicine. Apr. 1993. vol. 177, pp. 1199-1204.

Hendrix et al—Biologic Effects after a Single Dose of Poly(l):poly(C12U) in Healthy Volunteers. Antimicrobial Agents and Chemotherapy. Mar. 1993. vol. 37 (3), pp. 429-435.

Goldfeld et al—"Coordinate viral induction of tumor necrosis factor α and interferon β in human B cells and monocytes." Proceedings of the National Academy of Sciences of the United States of America. Mar. 1989. vol. 86, pp. 1490-1494.

Wong et al—"Tumor necrosis factors a and ft inhibit virus replication and synergize with interferons." Oct. 30, 1986. Nature vol. 323, pp. 819-822.

Urban et al—"Tumor necrosis factor: A potent effector molecule for tumor cell killing by activated macrophages." Proceedings of the National Academy of Sciences of the United States of America. Jul. 1986. vol. 83, pp. 5233-5237.

Talmadge et al—"Immunomodulatory Effects in Mice of Polyinosinic-Polycytidylic Acid Complexed with Poly-L-lysing and Carboxymethylcellulose." Cancer Research. Mar. 1985 vol. 45, pp. 1058-1065.

Youn et al—"Adjuvant Treatment with Chemotherapeutic Agents and Polyadenylic-Polyuridylic Acid in Operable Stomach Cancers." Yonsei Medical Journal. 1985. vol. 26, No. 1, pp. 1-7.

(56) References Cited

OTHER PUBLICATIONS

Kleinerman et al—"Constitutive Production and Release of a Lymphokine with Macrophage-activating Factor Activity Distinct from γ-Interferon by a Human T-Cell Leukemia Virus-positive Cell Line." Cancer Research. Oct. 1984. vol. 44, pp. 4470-4475.

Fleit et at—"Production of Interferon by in vitro Derived Bone Marrow Macrophages." Cellular Immunology. Jan. 15, 1981. vol. 57, pp. 495-504.

Alexopoulou, et al., "Recognition of double-stranded RNA and activation of NF-κB by Toll-like receptor 3" Nature, vol. 413, pp. 732-738 (2001).

Bot et al., "Receptor-Mediated Targeting of Spray-Dried Lipid Particles Coformulated with Immunoglobulin and Loaded with a Prototype Vaccine" Pharamaceutical Research, vol. 18, No. 7, 971-979 (2001).

Bhardwaj, et al., "Influenza Virus-infected Dendritic Cells Stimulate Strong Proliferative and Cytolytic Responses from Human CD8+ T cells" J. Clin. Invest. vol. 94, 797-807 (1994).

Bot et al. "Noncoding RNA danger motifs bridge innate and adaptive immunity and are potent adjuvants for vaccination" Journal of Clinical Investigation (2002).

Braganca, et al., "Type I interferon gene expression: Differential expression of IFN-A genes induced by viruses and double stranded RNA" Biochimle, vol. 80, 673-687 (1998).

Donner, et al., Evavold, et al., "Changes in Lymphocyte Subpopulations in Mice Receiving a Single Injection of PolyA:U" Ann. Immunol. 128C, 1039-1052 (1977).

Dormer, et al. "Effects of PolyA. Poly U In Vivi Alterations or Proportions of T and B Cell Subsets" Develop. biol. Standard. vol. 38, pp. 159-165 (1978).

Cella, et al., "Maturation, Activation and Protection of Dendritic Cells Induced by Double=stranded RNA" J. Exp. Med., vol. 189, No. 5, pp. 821-829 (1999).

Gallucci, et al., "Danger signals: SOS to the immune system" Current Opinion in Immunology, vol. 13, pp. 114-119 (2001).

Haines, et al., "Cellular Response to Double-Stranded RNA" J. of Cellular Biochemistry:vol. 46, pp. 9-20 (1991).

Hemmi, et al., "A Toll-like receptor recognizes bacterial DNA" Nature, vol, 408, pp. 740-745 (2000).

Kalergis, et al.,"Inducung Tumor Immunity through the Selective Engagement of Activating Fcγ Receptors on Dendritic Cells" J. Exp. Medicine. vol. 195, No. 12, 1653-1659 (2002).

Klinman, et al., "Immune Recognition of Foreign DNA: A Cure for Bioterrorism" Immunity, vol. 11, 123-129 (1999).

Lacour, J, "Clinical Trials Using Polyadenylic-Polyuridylic Acid as an Adjuvant to Surgery in Treating Different Human Tumors" Journal of Biologic Response Modifiers, vol. 4, 538-543 (1985).

Lunde, et al. "Troybodies and Pepbodies" Biochemical Society Transactions, vol. 30, part 4, pp. 500-506 (2002).

Matzinger, P., "Essay 1: The Danger Model in Its Historical Context" Scand. J. Immunol. vol. 43, 4-9 (2001).

Mellitis, et al., "Interaction of Adenovirus VA RNA₁ with Protein Kinase DA1: Nonequivalence of Binding and Function" Cell, vol. 61, pp. 843-852 (1990).

Nelson-Rampy, et al., "Establishment of Unresponsiveness in Primed B Lymphocytes In Vivo" Journal of Immunology, vol. 127, No. 4, 1415-1419 (1981).

Prasad, et al., "Cutting Edge: Recombinant Adenoviruses Induce CD+ T Cell Responses to an Inserted Protein Whose Expression is Limites to Nonimmune Cells" American Association of Immunologists pp. 4809-4812 (2001).

Rafiq, et al., "Immune complex-mediated Antigen presentation induces tumor immunity" Journal of Clinical Investigation, vol. 110, 1, 71-79 (2002).

Regnault, et al. "Fcγ Receptor-mediated Induction of Dendritic Cell Maturation and Major Histocompatibility Complex Class I-restricted Antigen Presentation after Immune Complex Internalization" J. exp. Med., 189, 2, 371-380 (1999).

Spiegelberg, H. "Human Myeloma IgG Half-Molecules Catabolism and Biological Properties" Journal of Clinical Investigation, vol. 56:588-594 (1975).

Zinkernagel, et al., "The Discovery of MHC Restriction" Immunology Today, vol. 18, 1, pp. 14-17 (1997).

Zaghouani, et al., "Contrasting efficacy of presentation by major histocompatibility complex class I and class II products when peptides are administered within a common protein carrer, self immunoglobulin" Eur. J. Immunol. 23: 2746-2750 (1993).

Absher et al., "Toxic Properties of a Synthetic Double-strnaded RNA (three articles)" Nature, vol. 233, pp. 715-718 (1969).

Kruisbeek et al., "Mechanism Underlying T cell Tolerance". Current Opinion in Immunology, vol. 8, 233-244 (1996).

Couzin "Small RNAs Make Big Splash" *Science,* vol. 298, pp. 2296-2297 (Dec. 2001).

Kadowaki, N, et al., "Distinct CpG and polyinosinic-polycytidylic acid doublestranded RNA, respectively, stimulate CD11c-type 2 dendritic cell precursors and CD11c+ dendritic cells to produce type I IFN." Journal Immunol. Feb. 2001, vol. 166, pp. 2291-2295.

Park, S. et al., "Adjuvant effect of polyadenylic:polyuridylic acid on antibody production of recombinant hepatitis B surface antigen in mice." *Internat. Journal Immunopharmacol.* 1995, vol. 17, No. 6, pp. 513-516.

Haines, D. et al., "Cellular responses to double-stranded RNA." *Journal Cell Blochem,* 1991, vol. 46, pp. 9-20.

Zaghouani, H. et al., "Cells expressing an H chain Ig gene carrying a viral T cell epitope are lysed by specific cytolytic T cells." *J. Immunol.* vol. 148, pp. 3604-3609 (Jun. 1992).

Naama, et al., "Complement, Antigen-Antibody Complexes and Immune Complex Disease" *J. Clin. Lab. Immunol.,* vol. 17, pp. 59-67 (1985).

Weigle, "Factors and Events in the Activation, Proliferation, and Differentiation of B Cells" *CRC Critical Reviews in Immunology,* vol. 7, Issue 4.

Miller, "Self-Nonself Discrimination and Tolerance in T and B Lymphocytes" *Immunol. Res.* vol. 12, pp. 115-130 (1993).

Drake, et al., "Prophylactic Therapy of Spontaneous Leukemia in AKR Mice by Polyadenylic-Polyuridylic Acid", Journal of the National Cancer Institute, vol. 52, No. 3, Mar. 1974, pp. 941-944 (4 pages).

\* cited by examiner

Figure 1C:

| Isotype | Binding to FcγR[1] | Complement activation[2] | Induction of cytokines[3] |
|---|---|---|---|
| CCL-159 | γ1 | + | ND | ND |
| CRL-1621 | γ1 | ++ | -/+ | + |
| CRL-11538 | γ3 | ND | ND | ND |
| CRL-11539 | γ3 | ++ | ++ | + |
| HB-8636 | γ4 | + | -/+ | + |

[1] Binding to FcγR+ human monocytic THP-1 cells and endosomal internalization
[2] Measurement of C4d production as is / or after heat aggregation
[3] Induction of IL-10 and TGF-β by human PBMC or THP-1 cells exposed to adsorbed IgG

PD 02 74

Fig. 1E: Epitopes and antigens (model)

Hemagglutinin of A/PR/8 influenza virus (precursor; HMIV / NCBI)

I-E$^d$ mkanllvllc alaaadadti cigyhannst dtvdtvlekn vtvthsvnll edshngklcr lkgiaplqlg kcniagwllg npecdpllpv rswsyivetp nsengicypg dfidyeelre qlssvssfer feifpkessw pnhnttkgvt aacshagkss fymllwlte kegsypklkn syvnkkgkev lvlwgihhps nskdqqniyq nenayvsvvt snynrrftpe iaerpkvrdq agrmnyywtl lkpgdtiife angnliapry afalsrgfgs giitsnasmh ecntkcqtpl gainsslpfq nihpvtigec pkyvrsaklr mvtglrnips iqsrglfgai agfieggwtg midgwygyhh qneqgsgyaa dqkstqnain gitnkvnsvi ekmniqftav gkefnklekr menlnkkvdd gfldiwtyna ellvllener tldfhdsnvk nlyekvksql knnakeigng cfefyhkcdn ecmesvrngt ydypkysees klnrekvdgv klesmgiyqi laiystvass lvllvslgai sfwmcsngsl qcrici [Seq. I.D. No. 8]

Nucleoprotein of A/PR/8 influenza virus (precursor; HMIV / NCBI)

K[d]

masqgtkrsy eqmetggerq nateirasvg rmvggigrfy iqmctelqls dyegrliqns itiermvlsa fderrnkyle ehpsagkdpk ktggpiykkr dgkwmrelil ydkdeirriw rqanngedat aglthlmiwh snlndatyqr tralvrtgmd prmcslmqgs tlprrsgaag aavkgigtmv melirmikrg indrnfwrge ngrrtriaye rmcnilkgkf qtaaqrammd qvresrnpgn aeiedlifla rsalilrgsv ahksclpaci yglvvasgyd feregyslvg idpfrllqns qvfslirpne npvhksqliw machsaafed lrvssfirgt kvvprgqltt rgvqiasnen metmdsitle lrskywairt rsggntnqqr asagqisvqp tfsvqrnlpf eratimaaft gnnegrtsdm rteiirmmes arpddvsfqg rgvfelsdek atnpivpsfd msnegsyffg dnaeeydn [Seq. I.D. No. 9]

VH segment of murine anti-arsonate antibody (G1MSAA / NCBI)

evqlqqsgae lvkagssvkm sckatgytfs syelywvrqa pgqgledlgy issssaypny aqkfqgrvti tadestntay melsslrsed tavyfcavrv isryfdgwgq gtlv [Seq. I.D. No. 10]

Fig. 1F: Epitopes and antigens

Influenza virus

M1 (PN0086/NCBI)

*HLA-A2* mslltevety vlsiipsgpl kaeiaqrled vfagkntdle vlmewlktrp ilspltkgvl gfvftltvps erglqrrfv qnalngngdp nnmdkavkly rklkreitfy gakevalsys tgalascmgl iynrmgtvtt evafglvcat ceqiadsqhr shrqmvtttn plirhenrmv lasttakame qmagsseqaa eamevasqar qmvqamrtvg thpsssaglk ddllenlqay qkrmgvqlqr fk [Seq. I.D. No. 11]

M2 (PN0087/NCBI)

*TM* mslltevetp trngwecscs dssdplviaa siigilhfil wildrlffkc iyrrlkyglk rgpstegvpk smreeyrqeq qnavdvddgh fvniele

Hepatitis C virus

NS3 (AAK54587/NCBI)

apitayaqqt rgllgciits ltgrdrnqve gevqvvstat qsflatcing vcwtvfhgag sktlagpkgp itqmytnvdq dlvgwpappg arsltpctcg ssdlylvtrh advvpvrrrs dsrgsllspr pisylkgssg gpllcpsgha vgifraavct rgvakavdfv pvesmettmr s [Seq. I.D. No. 13]

Hepatitis B virus

Core antigen (AAM 18211/NCBI)

mdidpykefg asvellsflp sdffpsirdl ldtasalyre alespehcsp hhtalrqail cwgelmnlat wvgsnledpa srelvvsyvn vnmglkirql lrfhiscltf gretvleylv sfgvwirtpp ayrppnapi [Seq. I.D. No. 14]

Fig. 1G: Epitopes and antigens (human system)

Human Papilloma Virus

HPV 18-E7 (P06788/NCI)

<u>HLA-A2</u> mhgpkatlqd ivlhlepqne ipvdllcheq lsdseeende idgvnhqhlp arraepqrht mlcmcckcea riklvvessa ddlrafqqlf lntlsfvcpw casqq [Seq. I.D. No. 15]

HPV *16*-E7 (AAL96657/NCI)

<u>HLA-A2</u>                                                  <u>HLA-A2</u> mhgdtptlhe ymldlqpett dlycyeqlnd sseeedeidg paggaepdra hynivtfcck cdstlrlcvq sthvdirtle dllmgtlgiv epicsqkp [Seq. I.D. No. 16]

HPV 18-E6 (CAB53096/NCI)

<u>HLA-A2</u>     <u>HLA-A2</u> marfedpttr pyklpdllete lntslqdiei tcvycktvle ltevfefafk dlfvvyrdsi phaachkcid fysrirelrh ysdsvygdtl ekltntglyn llirclrcqk plnpaeklrh lnekrrfhki aghyrgqchs ccnrarqerl qrrretqv [Seq. I.D. No. 17]

HPV *16*-E6 (AAL96630/NCI)

<u>HLA-B18</u> mhqkrtamfq dpqerprklp hlctelqtti hdiilecvyc kqqllrrevy dfafrdlciv yrdgnpyavc dkclkfyski seyryvcysv ygttleqqyn kplcdlllrc lncqkplcpe ekqrhldkkq rfhnirgrwt gremsccrss rtrretql [Seq. I.D. No. 18]

Fig. 1H: Epitopes and Antigens (human system)

Melanoma – gp100 (P40967/NCBI)

*HLA-A2*                                                                                                              *HLA-A2* mdlvlkrcll hlavigalla vgatkvprmq dwlgvsrqlr tkawmrqlyp ewteaqrldc wrggqvslkv sndgptlliga nasfsialnf pgsqkvlpdg qviwvnttii ngsqvwggqp vypqetddac ifpdggpcps gswsqkrsfv yvwktwgqyw qvlggpvsgl sigtgramlg thtmevtvyh rrgsrsyvpl ahsssaftit dqvpfsvsvs qlraldggnk hflrnqplttf alqlhdpsgy laeadlsytw dfgdssgtli sralvvthty lepgpvtaqv vlqaaiplts cgsspvpgtt dghrptaeap nttagqvptt evvgttpgqa ptaepsgrts vqvpttevis tapvqmptae stgmtpekvp vsevmgttla emstpeatgm tpaevsivvl sgttaaqvtt tewvettare lpipepegpd assimstesi tgslgpllldg tatlrlvkrq vpldcvlyry gsfsvtlldiv qgiesaeilq avpsgegdaf eltvscqggl pkeacmeiss pgcappaqrl cqpvlspsac qlvlhqilkg gsgtyclnvs ladtnslavv stqlimpgqe aglgqvpliv gillvlmavv lasliyrrrl mkqdfsvpql phssshwlrl prifcscpig enspllsgqq v [Seq. I.D. No. 19]

[substitute the following sequences in place of the second epitope for agonists: fl dqvafsv ; fl dqrvfvv ; fl flwffev]

MART-1 (Q16655/NCI)

*HLA-A2* mpredahfiy gypkkghghs yttaeeaagi giltvilgvl lligcwycrr rngyralmdk slhvgtqcal trrcpqegfd hrdskvslqe kncepvvpna ppayeklsae qspppysp [Seq. I.D. No. 20]

TRP-2 (CAA0437/NCI)

msplwwgfll sclgckilpg aqgqfprvcm tvdslvnkec cprlgaesan vcgsqqgrgq ctevradtrp wsgpyilmq ddrelwprkf fhrtckctgn fagyncgdck fgwtgpncer kkppviqrni hslspqereq flgaldlakk rvhpdyvitt qhwvgllgpn gtqpqfancs vydffvwlhy ysvrdtllgg ffpwlkvyyy rfviglrvwq wevisckllk rattrqp [Seq. I.D. No. 21]  llpsgrpy r   svydffvw ]

[alternate epitopes:

Fig. 1I: Epitopes and antigens (human system)

Carcinoma Embryonic Antigen Precursor ( XP 064845/NCBI)

mdlsrprwsl wrrvflmasl lacgicqasg qifitqtlgi kgyrtvvald kvpedvqeys wywgandsag nmiishkpps aqqpgpmytg rervnregsl lirptalndt gnytvrvag netqratgwl evelgsnlg isvnasslve nmdsvaadcl tnvtnitwyv ndvptsssdr mtispdgktl vilrvsrydr tiqcmiesfp eifqrseris ltvaygpdyv llrsnpddfn givtaeigsq vemecicysf ldlkyhwihn gsllnfsdak mnlsslaweq mgryrctven pvtqlimymd vriqaphecs ssppgscfah lpasmpc [Seq. I.D. No. 22]

Her-2 (CAD28392 human Her-2/neu p/NCBI)

melaalcrwg lllallppga astqvctgtd mklrlpaspe thldmlrhly qgcqvvqgnl eltylptnas lsflqdiqev qgyvliahnq vrqvplqrlr ivrgtqlfed nyalavldng dplnnttpvt gaspgglrel qlrslteilk ggvliqrnpq lcyqdtilwk difhknnqla ltlidtnrsr achpcspmck gsrcwgesse dcqsltrtvc aggcarckgp lptdccheqc aagctgpkhs dclaclhfnh sgicelhcpa lvtyntdtfe smpnpegryt fgascvtacp ynylstdvgs ctlvcplhnq evtaedgtqr cekcskpcar vcyglgmehl revravtsan iqefagckki fgslaflpes fdgdpasnta plqpeqlqvf etleeitgyl yisawpdslp dlsvfqnlqv irgrilhnga ysltlqglgi swlglrslre lgsglalihh nthlcfvhtv pwdqlfrnph qallhtanrp edecvgegla chqlcarghc wgpgptqcvn csqflrgqec veecrvlqgl preyvnarhc lpchpecqpq ngsvtcfgpe adqcvacahy kdppfcvarc psgvkpdlsy mpiwkfpdee gacqpcpinc thscvdlddk gcpaeqrasp ltsiisavvg illvvvlgvv fgilikrrqq kirkytmrrl lqetelvepl tpsgampnqa qmrilketel rkvkvlgsga fgtvykgiwi pdgenvkipv aikvlrents pkankeilde ayvmagvgsp yvsrllgicl tstvqlvtql mpygclldhv renrgrlgsq dllnwcmqia kgmsyledvr lvhrdlaarn vlvkspnhvk itdfglarll dideteyhad ggkvpikwma lesilrrrft hqsdvwsygv tvwelmtfga kpydgipare ipdllekger lpqppictid vymimvkcwm idsecrprfr elvsefsrma rdpqrfvviq nedlgpaspl dstfyrslle dddmgdlvda eeylvpqqgf fcpdpapgag gmvhhrhrss strsgggdlt lglepseeea prsplapseg agsdvfdgdl gmgaakglqs lpthdpsplq rysedptvpl psetdgyvap ltcspqpeyv nqpdvrpqpp spregplpaa rpagatlerp ktlspgkngv vkdvfafgga venpeyltpq ggaapqphpp pafspafdnl yywdqdpper gappstfkgt ptaenpeylg ldvpv [Seq. I.D. No. 23]

HLA-A2 anchor motif

FLXXXXXXV (X any aminoacid except C) [Seq. I.D. No. 24]

Fig. 1J: Epitopes and antigens (human system)

Tetanus toxin (AAM57257/NCBI)

kiipptnire nlynrtaslt dlggelciki knedltfiae knsfseepfq deivsyntkn kplnfnysld kiivdynlqs kitlpndrtt pvtkgipyap eyksnaasti eihniddnti yqylyaqksp ttlqritmtn svddalinst kiysyfpsvi skvnqgaqgi lflqwvrdii ddftnessqk ttidkisdvs tivpyigpal nivkqgyegn figalettgv vllleyipei tlpviaalsi aesstqkeki iktidnflek ryekwievyk lvkakwlgtv ntqfqkrsyq myrsleyqvd aikkiidyey kiysgpdkeq iadeinnlkn kleekankam ininifmres srsflvnqmi neakkqllef dtqsknilmq yikanskfig itelkklesk inkvfstpip fsysknldcw vdneedidvi lkkstilnld inndiisdis gfnssvityp daqlvpging kaihlvnnes sevivhkamd ieyndmfnnf tvsfwlrvpk vsashleqyg tneysiissm kkhslsigsg wsvslkgnnl iwtlkdsage vrqitfrdlp dkfnaylank wvfititndr lssanlying vlmgsaeitg lgairednni tlkldrcnnn nqyvsidkfr ifckalnpke ieklytsyls itflrdfwgn plrydteyyl ipvassskdv qlknitdymy ltnapsytng klniyyrrly nglkfiikry tpnneidsfv ksgdfiklyv synnnehivg ypkdgnafnn ldrilrvgyn apgiplykkm eavklrdlkt ysvqlklydd knaslglvgt hngqigndpn rdiliasnwy fnhlkdkilg cdwyfvptde gwtnd
[Seq. I.D. No. 25]

Universal T helper epitope

QYIKANSKFIGITEL [Seq. I.D. No. 26]

HIV-1: reverse transcriptase (AAN02999/NCBI)

eictemekeg kiskigpenp yntpvfaikk kdstkwrklv dfrelnkrtq dfwevqlgip hpaglkkkks vtvldvgday fsvpldkdfr kytaftipst nnetpgiryq ynvlpqgwkg spaifqssmt kilepfrkqn peiviyqymd dlyigsdlei gqhrtkieel rqhllkwglt tpdkkhqkep [Seq. I.D. No. 27]

Universal T helper epitope

FRKQNPDIVIYQYMDDLYVG [Seq. I.D. No. 28]

HIV-1: gag (AAM98735/NCBI)

wdrlhpaqag piapgqirep rgsdiagtts tlqeqitwmt nnppipvgei ykrwiilgln kivrmyspvs ildikqgpke pfrdyvdrff kalraeqatq dvknwmtdtl lvqnanpdck silrglgpga sleemmtacq gvggpshkar vlaeamsqan svnmmqrsnf kgpkrtvkcf ncgkeghiar ncraprkkgc wkcgqeghqm kdcterqanf lgkiwpshkg rpgnfl
[Seq. I.D. No. 29]

Fig. 1K: Self antigen / Epitopes

Insulin precursor – human (P01308/NCBI)

DQ8 malwmrllpl lallalwgpd paaafvnqhlcg shlvealy lvcgergffy tpktrreaed lqvgqvelgg gpgagslqpl alegslqkrg iveqcctsic slyqlenycn
[Seq. I.D. No. 30]

Glutamic acid decarboxylase – human GAD 65 (Q05329/NCBI)

DR4 maspgsgfws fgsedgsgds enpgtarawc qvaqkftggi gnklcallyg daekpaesgg sqppraaark aacacdqkpc scskvdvnya flhatdllpa cdgerptlaf lqdvmnillq yvvksfdrst kvidfhypne llqeynwela dqpqnleeil mhcqttlkya iktghpryfn qlstgldmvg laadwltsta ntnmftyeia pvfvlleyvt lkkmreiigw pggsgdgifs pggaisnmya mmiarfkmfp evkekgmaal prliaftseh shfslkkgaa algigtdsvi likcdergkm ipsdlerril eakqkgfvpf lvsatagttv ygafdpllav adickkykiw mhvdaawggg llmsrkhkwk lsgveransv twnphkmmgv plqcsallvr eeglmqncnq mhasylfqqd khydlsydtg dkalqcgrhv dvfklwlmwr akgttgfeah vdkclelaey lyniiknreg yemvfdgkpq htnvcfwyip pslrtledne ermsr lskva pvikarmmey gttmvsyqpl gdkvnffrmv isnpaathqd idflieeier lgqdl
[Seq. I.D. No. 31]

DR4**(2 epitopes) DR4* DR4 DR4* (2 epitopes)

Example of composite self epitope Insulin-GAD (used for construction of anti-diabetes drug):

insert-cg shlvealy lvcgerg-XXXX- prliaftseh shfsl-XXXX-lyniiknreg yemvf -XXXX- pslrtledne ermsr-insert
[Seq. I.D. No. 32]

Example of composite non-self epitope Tetanus-gp100,MART-1, TRP-2 (used for construction of anti-melanoma drug):

insert-qyikanskfigitel-XXXX- fldqvafsv-XXXX- aagigiltv -XXXX-svrdtllgg-insert [Seq. I.D. No. 33]

Fig. 1L

Prostate associated PAGE-1 (Homo sapiens) AAC25990 mgflrrliyrrrpmiyvesseessdeqpdevesptqsqdstpaeeredegasaaqgqepeadsqelvqpkt
gcepgdgpdtkrvclrneeqmklpaegpepeadsqeqvhpktgcergdgpdvqelglpnpeevktpeedeg
qsqp Six transmembrane epithelial antigen of the prostate (Homo sapiens)
NP_036581 mesrkditnqeelwkmkprrnleeddylhkdtgetsmlkrpvllhlhqtahadefdcpselqhtqelfpqw
hlpikiaaiiasltflytllrevihplatshqqyfykipilvinkvlpmvsitllalvylpgviaaivqlh
ngtkykkfphwldkwmltrkqfgllsfffavlhaiyslsypmrrsyryklInwayqqvqqnkedawiehdv
wrmeiyvslgivglailallavtsipsvsdsltwrefhyiqsklgivslllgtihalifawnkwidikqfv
wytpptfmiavflpivvlifksilflpclrkkilkirhgwedvtkinkteicsql G antigen, family C, 1; JM27 proteins; prostate-associated gene protein
4 (Homo sapiens) NP_036581 msarvrsrsrgrgdgqeapdvvafvapgesqqeepptdnqdiepgqeregtppieerkvegdcqemdlekt
rsergdgsdvkektppnpkhaktkeagdgqp Mucin 1, transmembrane; (Homo sapiens) NP_002447

Mtpgtqspffllllltvltvvtgsghasstpggeketsatqrssvpssteknavsmtssvlsshspgsgss
ttqgqdvtlapatepasgsaatwgqdvtsvpvtrpalgsttppahdvtsapdnkpapgstappahgvtsap
dtrpapgstappahgvtsapdtrpapgstappahgvtsapdtrpapgstappahgvtsapdtrpapgstap
pahgvtsapdtrpapgstappahgvtsapdtrpapgstappahgvtsapdtrpapgstappahgvtsapdt
rpapgstappahgvtsapdtrpapgstappahgvtsapdtrpapgstappahgvtsapdtrpapgstappa
hgvtsapdtrpapgstappahgvtsapdtrpapgstappahgvtsapdtrpapgstappahgvtsapdtrp
apgstappahgvtsapdtrpapgstappahgvtsapdtrpapgstappahgvtsapdtrpapgstappahg
vtsapdtrpapgstappahgvtsapdtrpapgstappahgvtsapdtrpapgstappahgvtsapdtrpap
gstappahgvtsapdtrpapgstappahgvtsapdtrpapgstappahgvtsapdtrpapgstappahgvt
sapdtrpapgstappahgvtsapdtrpapgstappahgvtsapdtrpapgstappahgvtsapdtrpapgs
tappahgvtsapdtrpapgstappahgvtsapdtrpapgstappahgvtsapdtrpapgstappahgvtsa
pdtrpapgstappahgvtsapdtrpapgstappahgvtsapdtrpapgstappahgvtsapdtrpapgsta
ppahgvtsapdtrpapgstappahgvtsapdtrpapgstappahgvtsapdtrpapgstappahgvtsapd
trpapgstappahgvtsapdnrpalgstappvhnvtsasgsasgsastlvhngtsaratttpaskstpfsi
pshhsdtpttlashstktdassthhssvppltssnhstspqlstgvsffflsfhisnlqfnssledpstdy
yqelqrdisemflqiykqggflglsnikfrpgsvvvqltlafregtinvhdvetqfnqykteaasrynlti
sdvsvsdvpfpfsaqsgagvpgwgiallvlvcvlvalaivylialavcqcrrknygqldifpardtyhpms
eyptyhthgryvppsstdrspyekvsagnggsslsytnpavaaasanl

Fig. 1M

Major surface glycoprotein G (attachment glycoprotein G) of O. RSV
Q86695 msnhthhfefktlkkawkaskyfivglsclyklnlkslvqmalsalamitlvsltitaiiyistgntkakp
mptptiqitqqfqnhtslpptehnhnsthsptqgttsphtfavdvtegtryyhltlktqggktkgpptpha
trkppissqksnpseiqqdysdfqilpyvpcnicegdsaclslcqdrsesildkaltttpkktpkpmttkk
ptktsthhrtslrnklyiktnmttpphglistakhnknqstvqnprhtla Attachment glycoprotein (Human respiratory syncytial virus) AAM82069 atdqiknttptyltqnpqlgisfsnlsettsqpttilasttpsaestpqsttvkikntttttqiqpskpttk
qrqnkpqnkpnndfhfevfnfvpcsicsnnptcwaickripnkkpgkktttkptkkptikttkkdpkpqtt
kpkevlttkptekptisttktnirttlltsnttgnpehtsqkgnpplnhl Glycoprotein G (Human herpes virus 1) AAN04791 tppmpsigleeeeeegagdgehleggdgtrdtlpqspgpafplaedvekdkpnrpvvpspdpnnsparpe
tsrpktpptiigplatrpttrlt Immediate early protein ICP47 (human herpes virus 1) AAG33134 mswalemadtfldt

Neurovirulence factor (ICP 34.5) (Human herpes virus 2) BAA23428 msrrrgprrrgprrrprpgapavprpgapavprpgalptadsqmvpaydsgtavesapaassllrrwllvp
qaddsddadyagnddaewansppsegggkapeaphaapaaacpppppprkergpqrplpphlalrlrtttey
larlslrrrrppasppadaprgkvcfsprvqvrhlvawetaarlarrgswareradrdrfrrrvaaaeavi
gpclepeararararahedggpaeeeeaaaaargssaaagpgrrav

Superior in vivo loading of APC by Ig-peptide technology

| | Spleen | Local lymph nodes | Thymus |
|---|---|---|---|
| HA -saline (4.5nM) | 0.12-0.4* | <0.04 | 0.12 |
| HA-saline (450nM) | 0.4-1.2 | 0.12-0.4 | 1.1-3.5 |
| HA-IFA (4.5nM) | 0.12-0.4 | 0.04-0.12 | 0.04-0.12 |
| HA-IFA (450nM) | 0.4-1.2 | 3.5-10.0 | 1.1-3.5 |
| IgHA (0.45nM) | 1.2-3.5 | 0.4-1.2 | 1.1-3.5 |
| IgHA (4.5nM) | 10.0 | 10.0-33.3 | 1.1-3.5 |

% of APC that are able to present peptide in given condition

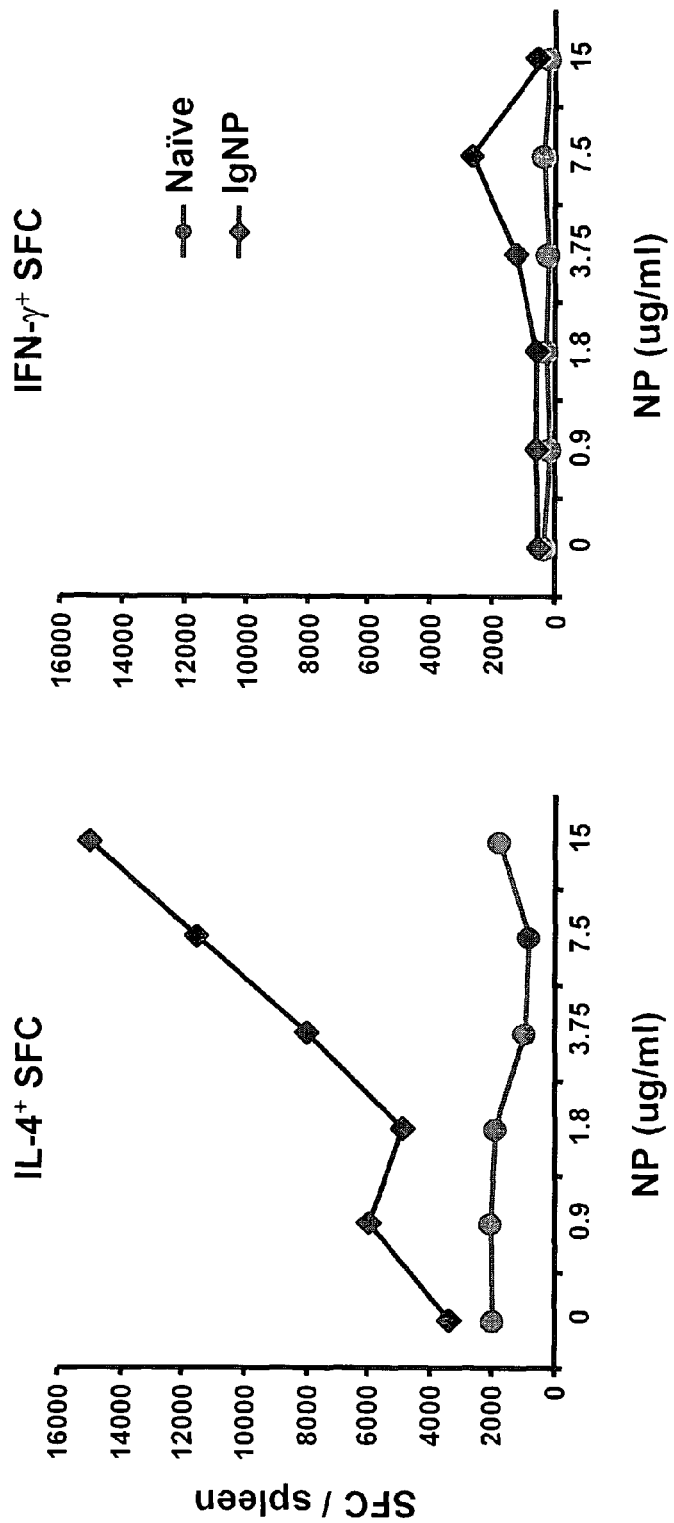
Fig. 19A: The Default Pathway: Induction of Tc2 Immunity

Figure 23A: Nucleotide composition of synthetic RNA compounds used for screening of immunomodulatory motifs.

| Category of RNA[A] | | Nucleotide composition |
|---|---|---|
| Single-stranded RNA | Group 1 (Pool 1) | p[B](A); p(C); p(G); p(I); p(U) |
| | Group 2 (Pool 2) | p(G,U); p(C,U); p(A,C); p(I,U) |
| | Group 3 (Pool 3) | p(C,I); p(A,U); p(A,G) |
| | Group 4 (Pool 4) | p(A,C,G); p(A,C,U); p(A,G,U) |
| Double-stranded RNA | Group 5 (Pool 5) | pC:pG; pA:pU; pI:pC |

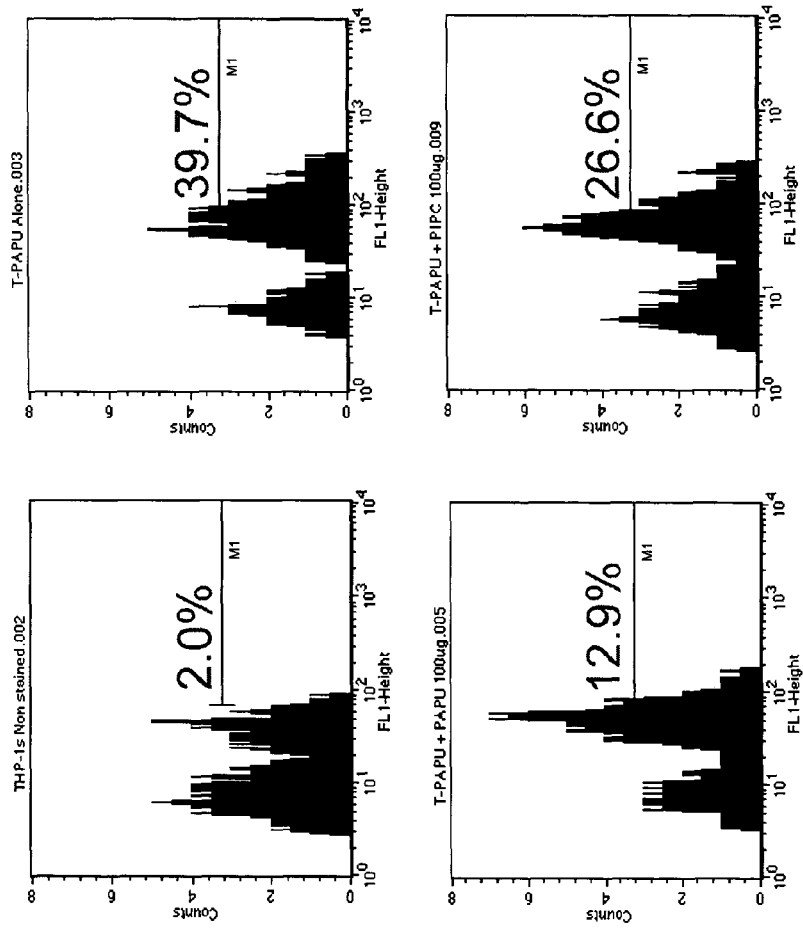
Figure 30A: Binding (FACS) to human cells

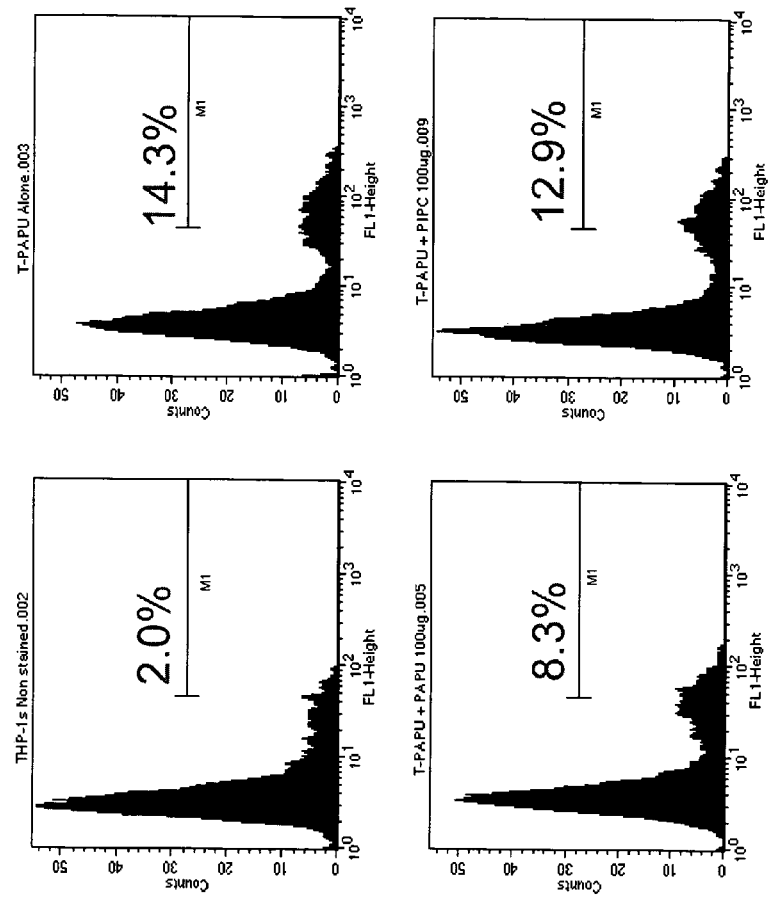
Figure 30B: Binding (FACS) to human cells

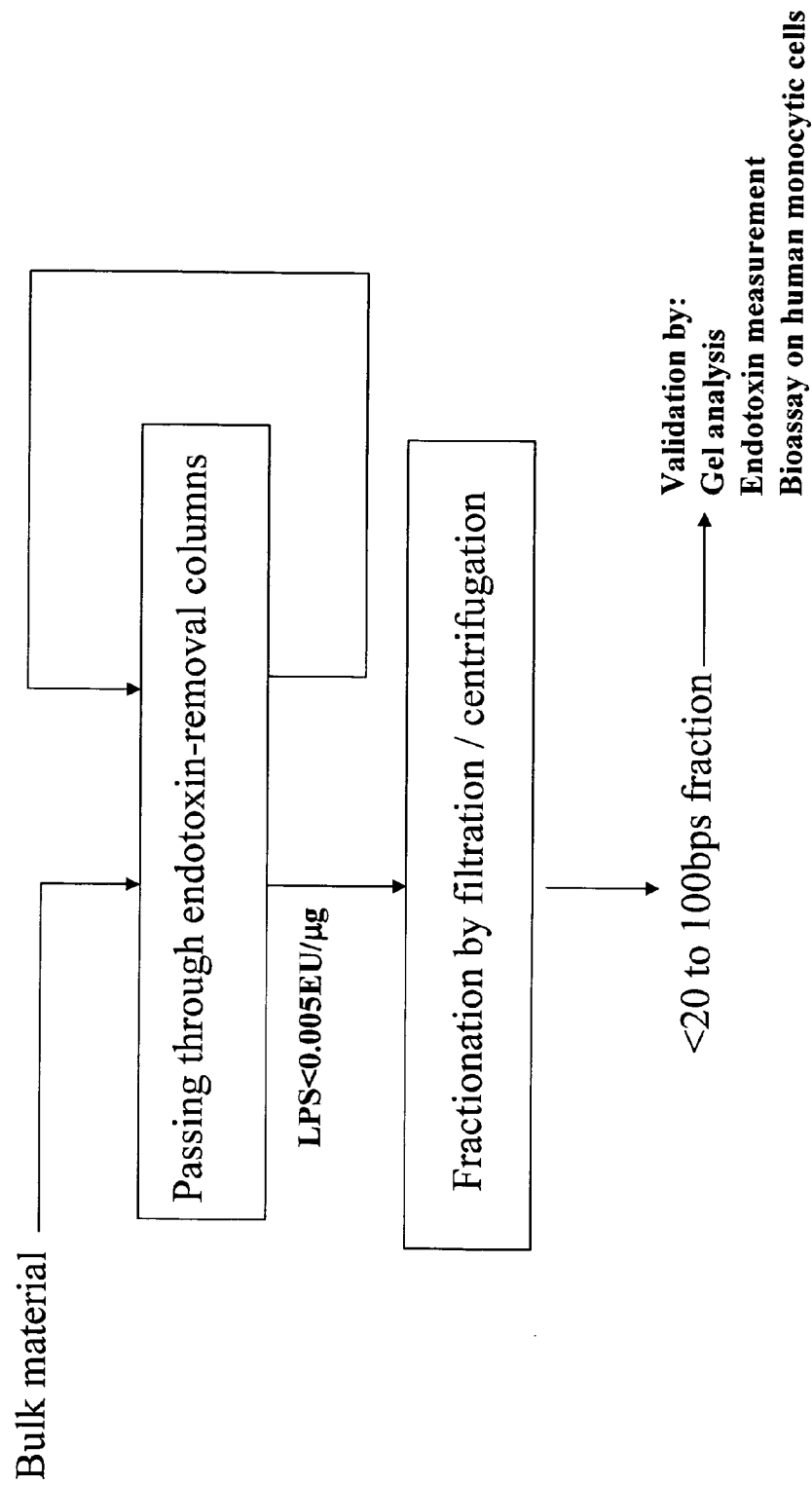
Figure 31: Fractionation of adjuvant dsRNA

Figure 32: Activity of different fractions
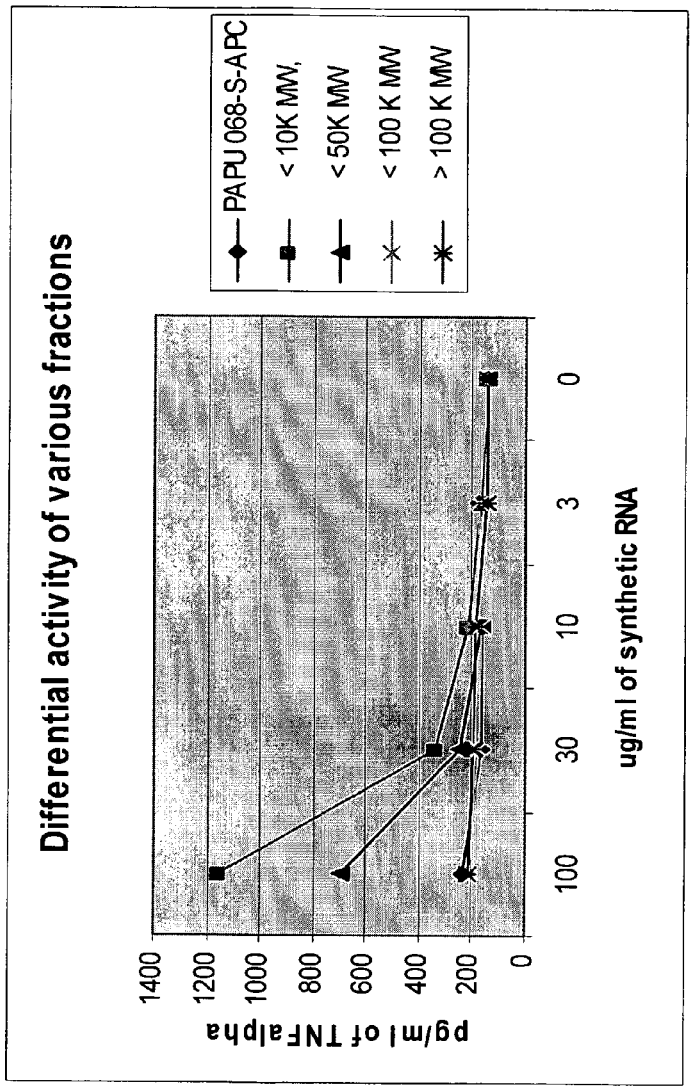
Amounts of endotoxin similar to contamination result in < 160pg/ml TNF-alpha

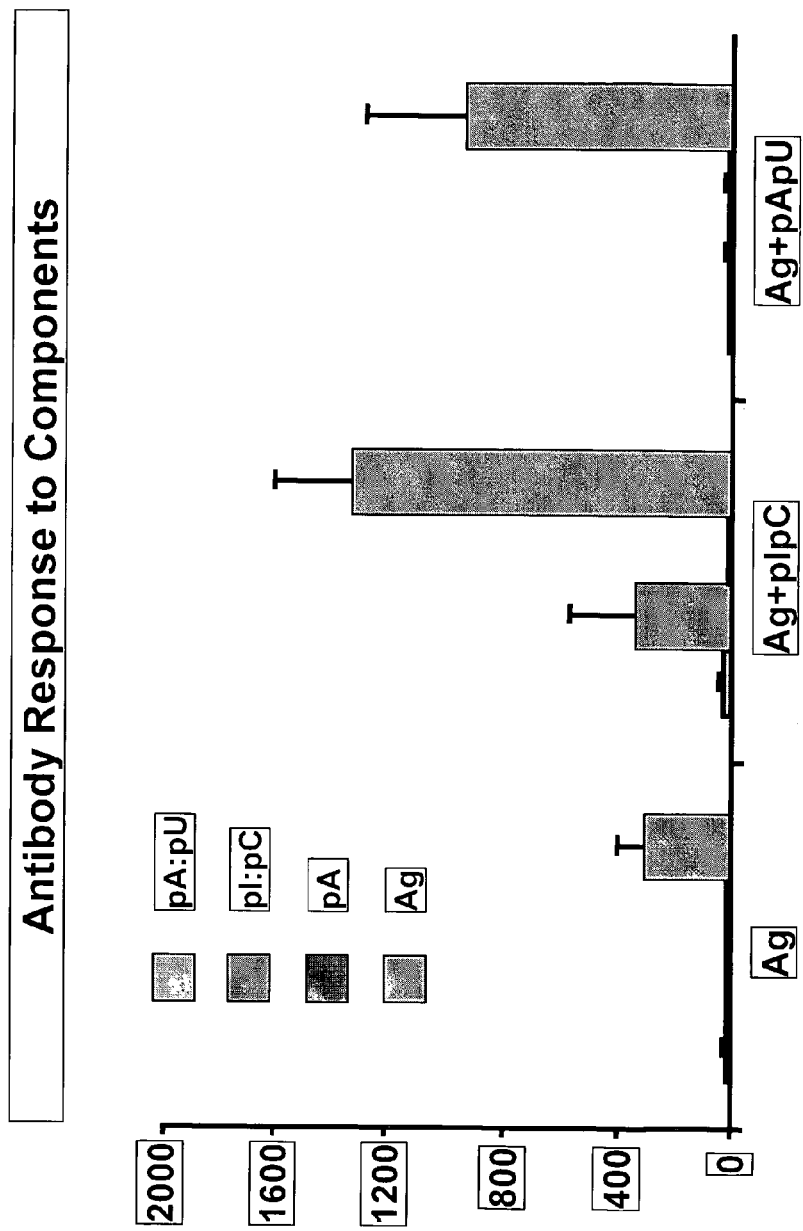
Fig. 33: Lack of Immunogenicity of Synthetic dsRNA Comprising Naturally Occurring Nucleotides Note: the immunotherapeutic protocol comprised administration of Ig0TAA + dsRNA$_1$

Figure 45A:

| Tumor challenge | Status of animals prior to the challenge | Rate of tumoral disease upon subsequent challenge |
|---|---|---|
| SP2/0-IgNP (homologous) | Naïve<br>Cured | 4/4<br>0/10 |
| SP2/0-IgHA (heterologous) | Naïve<br>Cured | 4/4<br>0/10 |
| SP2/0 (heterologous) | Naïve<br>Cured | 4/4<br>0/8 |
| SP2/0-IgW (heterologous) | Naïve<br>Cured | 4/4<br>0/2 |
| 4T-1 (breast cancer) | Naïve<br>Cured | 4/4<br>4/4 | ns # METHODS AND COMPOSITIONS TO GENERATE AND CONTROL THE EFFECTOR PROFILE OF T CELLS BY SIMULTANEOUS LOADING AND ACTIVATION OF SELECTED SUBSETS OF ANTIGEN PRESENTING CELLS

RELATED CASES

The present application claims priority to U.S. patent application Ser. No. 60/412,219 filed Sep. 20, 2002 and international application number PCT/US03/07995 filed on Mar. 14, 2003, both of which are hereby incorporated by reference in their entireties.

FIELD OF THE INVENTION

The present invention is generally directed to methods and compositions to generate an immune response. More specifically, the present invention is directed to methods and compositions of loading an antigen presenting cell to display a delivered epitope on a MHC class I molecule in a context appropriate for the generation of desired T cell responses.

BACKGROUND OF THE INVENTION

No direct evidence has been shown that delivery of antigen via Fc gamma receptors ("FcγR") triggers an effective anti-tumoral or antiinfectious response. For example, it was previously shown that delivery of a viral NP (nucleoprotein) derived epitope within an immunoglobulin or IgG backbone did not result in detectable induction of cytotoxic immunity (Zaghouani et al., Eur J Immunol. 1993 November; 23(11): 2746-50). In contrast, delivery of the same epitope in context of NP expressing cells (transfectomas) resulted in significant cytolytic activity. It was therefore concluded at that time that "APC (antigen presenting cells) are unable to present an influenza nucleoprotein [NP] peptide from the same context (1 microM Ig-NP) to an MHC class I-restricted T cell" and thus, "the endocytic compartment, when offered MHC class I- and II-restricted peptides within the same carrier protein context, favors presentation by class II by at least 1000-fold".

Access of the NP epitope to MHC class I presentation pathway is dependent on delivery strategy and was thus believed to be severely limited subsequent to FcγR internalization. More recently, it has been proposed that cross-linking or simultaneous engagement of FcγR on antigen presenting cells ("APC") may greatly optimize signal transduction and result in stimulation of cross-priming and APC stimulation, resulting in effective loading of MHC class I molecules (Regnault et al., J Exp Med. 1999, Jan. 18; 189(2):371-80). This could be achieved using immune complexes (multivalent antigen-antibody non-covalent complexes); however, due to the potential of C ("complement") mediated disease, the complexes could only be administered to the APC ex vivo (Naama et al., J Clin Lab Immunol. 1985 June; 17(2):59-67; Rafiq et al., J Clin Invest. 2002 July; 110(1):71-9). Alternatively, (Fab) 2-antigen recombinant fusion constructs directed to receptors onto APC, can result in receptor cross-linking internalization, and presentation in context of MHC class II molecules (Lunde et al., Biochem Soc Trans 2002; 30(4):500-6). The insertion of antigen, however, modifies the Fc portion of the constant domains (CH2 and CH3) of the immunoglobulin ("Ig") that can result in serious and unpredictable effects on the half life and pharmacokinetics, two parameters that are tightly associated with the integrity of this segment (Spiegelberg H L, J Clin Invest 1975 September; 56(3):588-94). Finally, there is no conclusive evidence to date that either one of the strategies described above, when applied in vivo, induce protective or therapeutic anti-tumoral or anti-microbial immunity that would be associated with the generation of optimal MHC class I and II-restricted T cells that produce specific cytokines such as IFN-γ. Even when applied ex vivo, the immune complex strategy has displayed limited efficacy due to the balance in the activity of ITAM+ and ITIM+ FcγR (Kalergis and Ravetch, J Exp Med 2002 June 17; 195(12): 1653-9). Thus, it has yet to be determined whether in vivo delivery of antigen to APC via the monovalent ligation of Fcγ receptors can be used to induce effective anti-tumoral or antiviral immunity.

PCT Application Serial Number PCT/US03/07995 filed Mar. 14, 2002 and U.S. patent application Ser. No. 60/364, 490 filed Apr. 30, 2002 are hereby incorporated by reference. Swiss-Protein/Trembl Protein Knowledgebase™ on CD-ROM, available from Geneva BioInformatics, is hereby incorporated by reference in its entirety.

SUMMARY OF THE INVENTION

The present invention demonstrates, contrary to expectations, that in vivo and ex vivo loading of APC via monovalent engagement of FcγR, using peptide epitopes covalently attached to the IgG backbone without modification of the Fc portion, results in access of the epitope to the MHC I processing and presentation pathway, with effective loading of MHC class I molecules. Unexpectedly, this results in generation of robust Tc2 responses characterized by IL-4, but not IL-2 or IFN-γ-producing, MHC class I restricted T cells that recognize the epitope within IgG backbone.

In addition, the generation of this "deviated" response was not effective in controlling a pathologic process associated with tumor growth, nor was it associated with significant priming of cytolytic T cells. This explains largely the previous failure to detect induction of immunity in similar context previously and demonstrates, unexpectedly, that cross-linking or multivalent engagement of FcγR on APC (such as in context of immune complexes or Fab2-antigen compounds) is not a prerequisite for effective loading of the peptide onto MHC class I molecules. This is important since the concept could be applied in vivo (in contrast to immune complexes) and the integrity of Fc portion and thus PK profile could be retained (in contrast to Fab2-antigen recombinant molecules). Despite effective loading of MHC class I molecules, the APC were not able to trigger protective anti-tumoral and anti-microbial immunity when loaded in vivo by peptide epitope within IgG backbone.

Further, the present application discloses novel compositions that result in effective redirection of class I-immunity to Tc1 effectors that take advantage of the unexpected loading of MHC I by peptide within IgG backbone. Such compositions are able to transform seemingly ineffective MHC class II and class I-restricted peptides into highly effective ones. FcγR-mediated loading of APC associated with stimulation of APC by novel synthetic polynucleotides, result in generation of class I-restricted cytolytic cells and IFN-γ, IL-2 producing T cells, further associated with protection against a highly virulent microbe or recovery from malignant tumoral process. It is also shown that variants of the technology, applied incorrectly or as previously proposed, are not optimal in generation of immunity protective against viruses or tumors, in particular of MHC class I-restricted nature. The present application demonstrates the reason for past failures and teaches how to obtain and apply the different components of the technology in order to obtain optimal effect.

Various embodiments of the invention include:
1. A method of loading an antigen presenting cell and generating a T cell response against an antigen or peptide epitope by use of at least one peptide epitope attached to an Ig, Ig backbone backbone or portion thereof thereby forming an Ig-peptide molecule/complex or portion thereof wherein when administered to a patient in vivo or ex vivo, the epitope is effectively processed and presented by the MHC I pathway of the antigen presenting cell resulting in effective loading of MHC class, I molecules on the antigen presenting cell thereby resulting in an MHC class I-peptide complex.
2. The method of paragraph 1 wherein the Ig-peptide molecule/complex or portion thereof is administered with RNA strands.
3. The method of paragraph 2 wherein the RNA is dsRNA strand and is pA:pU.
4. The method of paragraph 3 wherein the dsRNA is pA:pU and the dsRNA is between approximately 20-100 base pairs in size.
5. The method of paragraphs 1, 2, 3 or 4 wherein the Ig backbone is derived from human Ig.
6. The method of paragraphs 1, 2, 3 or 4 wherein the Ig backbone is derived from human IgG.
7. The method of paragraph 1, 2, 3 or 4 wherein the Ig backbone is humanized Ig.
8. The method of paragraph 1 wherein the antigen presenting cell is loaded via monovalent engagement of FcγR.
9. The method of paragraph 1 wherein the antigen presenting cell may be loaded in vivo or ex vivo.
10. The method of paragraph 1 wherein the peptide epitopes are covalently attached to the Ig backbone.
11. The method of paragraph 1 wherein the peptide epitope is attached to the Ig backbone without modification of the Fc portion of the Ig.
12. The method of paragraph 1 wherein the peptide epitope is inserted within a CDR region of the immunoglobulin molecule.
13. The method of paragraphs 1, 2, 3 or 4 wherein the peptide epitope is inserted within a CDR region of the immunoglobulin molecule by insertion or deletion.
14. The method of paragraphs 1, 2, 3 or 4 wherein the MHC class I-peptide complex results in generation of robust Tc2 responses characterized by IL-4 but not IL-2 or IFN-γ-production.
15. The method of paragraph 1 wherein the peptide epitope is selected from the group consisting of: influenza virus M1 or M2; hepatitis C virus NS3; hepatitis B virus core antigen; human papilloma virus HPV 18-E7, HPV 16-E7, HPV 18 E6, HPV 16 E6; melanoma-gp100; MART-1; TRP-2; carcinoembryonic antigen precursor; Her-2; tetanus toxin universal T helper epitope; HIV-1: reverse transcriptase; HIV1: gag; insulin precursor-human; human Gad 65; prostate tumor antigens; mucin 1; herpes simplex antigens; and, respiratory syncytial virus antigens.
16. The method of paragraph 1 wherein the negative effects of sera are avoided.
17. The method of paragraphs 1, 2, 3 or 4 wherein the Ig peptide molecule and dsRNA are administered by subcutaneous or intraperitoneal injection.
18. The method of paragraph 1 wherein the antigen presenting cell is selected from the group consisting of dendritic cells, monocytes, macrophages and B cells.
19. The method of paragraph 1 wherein the antigen presenting cell is selected from the group consisting of CD11c+ and CD11b+ APC.
20. The method of paragraph 1 wherein the resulting MHC-peptide complexes formed by in vivo delivery are expressed for up to 1 to 2 weeks.
21. The method of paragraphs 1, 2, 3 or 4 wherein the MHC-peptide complex results in activation of T cells.
22. The method of paragraph 21 wherein the T cell response is determined by ITAM+ and ITIM+ Fcgamma receptors on APC.
23. The method of paragraph 21 wherein expression of the gamma chain of ITAM+ FcγR isoforms induces the T cell response wherein ITIM+ FcγRII limits the T cell response.
24. The method of paragraphs 18 or 19 wherein monocytes induce Th2 and Tr1 cells, both dendritic cells and monocytes induce Th3 cells, and wherein CD11b+ monocytes are more potent than dendritic cells in triggering a regulatory response following IgG-mediated delivery of T cell epitope.
25. The method of paragraphs 1, 2, 3 or 4 wherein the loading of APC with a peptide delivered within an Ig backbone in vivo results in induction of Th2 immunity.
26. The method of paragraphs 1, 2, 3 or 4 wherein the loading of APC with a peptide delivered within an Ig backbone in vivo results in induction of Th3 and Tr1 immunity.
27. The method of paragraph 1 wherein the T cell response is enhanced by co-stimulation with one of the following selected from the group consisting of anti-CD40mAb, recombinant IL-12 or synthetic dsRNA.
28. The method of paragraphs 1, 2, 3 or 4 wherein IL-2, IFN-γ and IL-4 are down-regulated in a dose dependent manner and IL-10 and TGF-beta are upregulated in a dose-dependent manner.
29. The method of paragraphs 1, 2, 3, or 4 wherein the peptide epitope is recNP and induces NP-specific MHC class I-restricted T cell immunity consisting of IL-4 producing Tc2 cells.
30. The method of paragraph 1 further comprising the use of RNA motifs thereby resulting in a modified immune response.
31. The method of paragraph 30 wherein the RNA motifs are dsRNA.
32. The method of paragraph 27 wherein the IgG1 and IgG2a antibody responses were increased and associated with an enhanced Th1 and Th2 response.
33. The method of paragraph 2, 27 or 30 wherein the dsRNA was selected from the group consisting of pA:pU, pI:pC and pC:pG.
34. The method of paragraphs 27 or 30 wherein the dsRNA is pA:pU and induced MHC class I-restricted Tc1 cells thereby producing IFN-γ.
35. The method of paragraphs 33 or 34 wherein the dsRNA are from 10-50 Kd.
36. The method of paragraphs 2 or 30 wherein the RNA motifs are ssRNA selected from the group consisting of p(A), p(C), p(G), p(I) and p(U).
37. The method of paragraph 1 wherein the peptide-epitope is NP and further comprising the coadministration of dsRNA motifs thereby resulting in effective induction of IL-2 and IFN-gamma.
38. The method of paragraph 1 wherein the APC are loaded ex vivo resulting in the formation of MHC class I-peptide complexes and generation of a Tc response.
39. The method of paragraph 38 wherein the APC are administered to the patient by adoptive transfer.
40. The method of paragraph 38 wherein the formation of MHC class I-peptide complexes results in differentiation of Tc2 cells producing IL-4 but not IFN-gamma.

41. The method of paragraph 38 wherein further comprising the step of administering RNA motifs thereby resulting in a broadening of the T cell profile to include IFN-gamma producing Tc1 cells.
42. A method of immunization of a patient comprised of loading an antigen presenting cell by use of at least one peptide epitope of an antigen attached to an Ig backbone or portion thereof thereby forming an Ig-peptide molecule and administering to the patient in vivo the Ig-peptide molecule in conjunction with a dsRNA motif wherein the epitope is effectively processed and presented by the MHC I pathway resulting in effective loading of MHC class I molecules and thereby resulting in an effective secondary expansion of MHC class I-restricted T cells subsequent to in vivo exposure to the antigen.
43. The method of paragraph 42 wherein the antigen is a virus.
44. The method of paragraph 43 wherein the virus is the influenza virus.
45. The method of paragraph 42 wherein the peptide-epitope is recIgG-NP(Kd).
46. The method of paragraph 42 wherein the dsRNA is pA:pU.
47. The method of paragraph 42 wherein the T cells are cytotoxic T lymphocytes.
48. The method of paragraph 42 wherein the secondary expansion of MHC class I-restricted T cells subsequent to in vivo exposure to the antigen is greater than administration of the recombinant antigen in sterile saline only.
49. A method of controlling and treatment of a tumor after clinical diagnosis, by loading an antigen presenting cell by use of at least one tumor associated T cell epitope attached to an IgG backbone or portion thereof thereby forming an IgG-peptide molecule and administering the Ig-peptide molecule in vivo in conjunction with dsRNA.
50. The method of paragraph 49 wherein the tumor associated T cell epitope is effectively processed and presented by the MHC I pathway resulting in effective loading of MHC class I molecules on the antigen presenting cell thereby resulting in an MHC class I-peptide complex.
51. The method of paragraph 49 wherein the method results in an immune response to the tumor associated T cell epitope and tumor rejection.
52. The method of paragraphs 49, 50 or 51 wherein the dsRNA is pA:pU.
53. The method of paragraph 49 wherein the Ig-G peptide complex and dsRNA are administered repeatedly as an anti-tumor therapy.
54. The method of paragraph 49 wherein upon tumor rejection, Tc1 immunity is developed against the tumor associated epitope.
55. The method of paragraph 49 where upon administration of IgG-peptide and dsRNA, Tc2 immunity is developed against the tumor associated epitope.
56. The method of paragraph 49 wherein the method further induces an effective memory response to the same tumor associated epitope.
57. The method of paragraph 49 wherein the method results in continued immunity to tumor cell variants.
58. The method of paragraphs 49, 50, 51, 52, 53, 54, 55, 56, or 57 wherein the tumor associated T cell epitope is selected from the group consisting of melanoma-gp100, MART-1, TRP-2, carcinoembryonic antigen precursor XP 064845/NCB1, Her-2, prostate tumor antigens, and MUC 1.
59. A recombinant human Ig molecule or portion thereof capable of binding to an FcγR of an APC, comprising of a $CH_3$ region adjacent to a $CH_2$ region whereby a hinge region attaches an antigen to the $CH_2$ region wherein the antigen has an oligo-glycine linker attached to the hinge region.
60. The recombinant human Ig molecule of paragraph 59 whereby the antigen has a flanking sequence extending therefrom followed by a leader.
61. The recombinant human Ig molecule of paragraph 59 wherein the human Ig molecule is an IgG molecule.
62. The recombinant human Ig molecule of paragraph 59 wherein the antigen is a viral or tumor antigen.
63. The recombinant human Ig molecule of paragraph 59 wherein the amino acid sequence of the $CH_3$ region is: GQPREPQVYTLPPSREEMTKNQVSLT-CLVKGFYPSDIAVEWESNGQPENNY KTTPPVLDS-DGSFFLYSKLTVDKSRWQQGNVFSCSVM-HEALHNHYTQKSLSLSP GK and conservatively modified variants thereof. [Seq. I.D. No. 1].
64. The recombinant human Ig molecule of paragraph 59 wherein the amino acid sequence of the $CH_2$ region is: APELLGGPSVFLFPPKPKDTLMISRTPEVTCV VVD-VSHEDPEVKFNWYVDGVEVHNAKTKPRE-EQYNSTYRVVSVLTVLHQDWL NGKEYKCK-VFNKALPAPIEKTISKAK and conservatively modified variants thereof. [Seq. I.D. No. 2].
65. The recombinant human Ig molecule of paragraph 59 wherein the amino acid sequence of the hinge region is: EPKSCDKTHTCPPCP and conservatively modified variants thereof. [Seq. I.D. No. 3].
66. The recombinant human Ig molecule of paragraph 53 wherein the amino acid sequence of the flanking sequence is: QVQLQ and conservatively modified variants thereof. [Seq. I.D. No. 4].
67. A composition for enhancing an immune response to an antigen wherein the composition is a polynucleotide wherein the polynucleotide is made up of compounds selected from the group consisting of adenine, uracil, guanine, cytosine and inosine.
68. The composition of paragraph 67 wherein the polynucleotide is dsRNA.
69. The composition of paragraph 68 wherein the dsRNA is selected from the group consisting of pA:pU and pI:pC.
70. The composition of paragraph 69 wherein the dsRNA is pA:pU and wherein some of the adenine and uracil is occasionally replaced by guanine, cytosine or inosine along the polynucleotide chain.
71. The composition of paragraph 69 wherein the antigen is a virus.
72. The composition of paragraph 69 wherein the antigen is attached to an inunumoglobulin or portion thereof and administered in vivo.
73. The composition of paragraph 72 wherein the antigen is protein or a peptide.
74. The composition of paragraphs 67, 68, 69 or 70 wherein the antigen is a tumor associated epitope.
75. The composition of paragraph 74 wherein the antigen is a T cell epitope.
76. The composition of paragraphs 67, 68, 69 or 70 wherein the dsRNA is administered together with said antigen.
77. The composition of paragraph 67 wherein the polynucleotide is dsRNA and is coadministererd with the antigen.
78. The composition of paragraph 67 wherein the antigen is already present in the body.
79. The composition of paragraph 67 wherein the antigen is administered in a pharmaceutically acceptable carrier.

80. Use of dsRNA in the manufacture of a medicament for enhancing an immune response to an antigen in a patient, comprising administering said dsRNA to a patient in conjunction with said antigen.

81. The use of paragraph 80 wherein an epitope of said antigen is delivered to the patient in an immunoglobulin or portion thereof.

82. The use of paragraphs 80 or 81 wherein the dsRNA is comprised of pA:pU.

83. The use of paragraphs 80 or 81 wherein the dsRNA is comprised of pI:pC.

84. The use of paragraph 81 wherein the dsRNA consists of bases selected from the group consisting of adenine, cytosine, uracil, guanine and inosine.

85. The use of paragraphs 81, 82 or 83 wherein the use enhances the Th1 and/or Tc1 response to the antigen.

86. The use of paragraphs 81, 82 or 83 wherein the use induces a Tc1 cell response to the antigen.

87. The use of paragraphs 81, 82 or 83 wherein the immune response includes an enhanced B cell response.

88. The use of paragraphs 81, 82 or 83 wherein the antigen is administered with additional antigen.

89. The use of paragraphs 81, 82 or 83 wherein the use induces expression of CXC and CC chemokines.

90. The use of paragraphs 81, 82 or 83 wherein the administering of dsRNA enhances T or B cell responses or both T and B cell responses by recruitment and activation of CD11b+ monocytes.

91. The use of paragraphs 81, 82 or 83 wherein the administering of dsRNA enhances T or B cell responses or both T and B cell responses by recruitment and activation of dendritic cells.

92. The use of paragraphs 81, 82 or 83 wherein the dsRNA compositions enhance an immune response by recruiting antigen presenting cells.

93. The use of paragraph 92 wherein the antigen presenting cell is a professional antigen presenting cell.

94. The use of paragraph 92 wherein the antigen presenting cell is a naive antigen presenting cell.

95. The use of paragraphs 81, 82 or 83 wherein the antigen is a non-infectious antigen and wherein the MHC Class 1 restricted T cells are cross-primed by the dsRNA.

96. The use of paragraphs 81, 82 or 83 wherein the composition and antigens are administered by one of the following selected from the group consisting of mucosal administration, respiratory administration, intravenous administration, subcutaneous administration, and intramuscular administration.

97. The use of paragraph 81 wherein the antigen is administered in an immunoglobulin or portion thereof or in an immunoglobulin backbone.

98. The use of paragraph 97 wherein the wherein the antigen is a peptide epitope.

99. A method of preventing high zone tolerance in a patient to an antigen comprising administering said antigen together with a dsRNA composition wherein the dsRNA composition comprises at least one compound selected from the group consisting of poly-adenine, poly-uracil, poly-guanine, poly-cytosine, poly-inosine.

100. The method of paragraph 99 wherein the antigen is non-infectious.

101. The method of paragraph 99 wherein the antigen is administered in high doses or already present in the body.

102. The method of paragraphs 99, 100 or 101 wherein the dsRNA is selected from the group consisting of pA:pU and pI:pC.

103. The method of paragraphs 99, 100, 101 or 102 wherein the method prevents B cell unresponsiveness.

104. A method of enhancing the immune system in a patient exposed to a pathogen comprising the administration of dsRNA to the patient.

105. The method of paragraph 104 wherein the dsRNA is selected from the group consisting of pA:pU and pI:pC.

106. The method of paragraphs 104 or 105 wherein the dsRNA is administered to a patient in concentrations ranging from 100 ug/ml to 1 mg/ml.

107. The method of paragraphs 104, 105 or 106 wherein the pathogen is unknown.

108. The method of paragraphs 104, 105, 106 or 107 wherein the dsRNA is administered in a pharmaceutically acceptable carrier.

109. The method of paragraph 104 wherein a T cell response to the pathogen is enhanced.

110. A method of enhancing an immune response in a patient in need thereof comprising loading an antigen presenting cell by use of at least one peptide epitope of an antigen attached to an Ig backbone thereby forming an Ig-peptide complex or molecule and administering the Ig-peptide complex or molecule in vivo in conjunction with a dsRNA motif wherein the epitope is effectively processed and presented by the MHC pathway of the antigen presenting cell resulting in effective loading of MHC molecules and thereby resulting in an effective secondary expansion of MHC molecules subsequent to in vivo exposure to the antigen.

111. The method of paragraph 110 wherein the MHC pathway is the MHC I pathway.

112. The method of paragraph 110 wherein the MHC pathway is the MHC II pathway.

113. The method of paragraph 111 wherein the method results in effective loading of MHC Class I molecules on the antigen presenting cell.

114. The method of paragraph 112 wherein the method results in effective loading of MHC Class II molecules on the antigen presenting cell.

115. The method paragraphs 110, 111 or 112 wherein the dsRNA is pA:pU.

116. The method of paragraphs 110, 111 or 113 wherein the method results in secondary expansion of MHC Class I restricted T cells.

117. The method of paragraph 115 wherein the antigen is a virus.

118. The method of paragraph 117 wherein the virus is an influenza virus.

119. The method of paragraph 115 wherein the antigen is a tumor associated epitope.

120. The method of paragraph 115 wherein the T cell is a cytotoxic T lymphocyte.

121. A method of generating an immune response to an antigen in a patient comprising:
administering to the patient an immunoglobulin or portion thereof wherein said immunoglobulin has at least one peptide epitope of said antigen attached to said immunoglobulin or portion thereof and administering said immunoglobulin or portion thereof in conjunction with a dsRNA segment.

122. The method of paragraph 121 wherein the immunoglobulin or portion thereof and said dsRNA segment are administered together.

123. The method of paragraph 121 wherein the immunoglobulin or portion thereof and said dsRNA segment are administered separately.

124. The method of paragraph 121 wherein said patient is human.

125. The method of paragraph 121 wherein upon administration of said immunoglobulin or portion thereof to said patient the immunoglobulin or portion thereof loads the antigen presenting cell by engagement with the antigen presenting cell's FcγR said peptide epitope is effectively processed and presented by the MHC I pathway of the antigen presenting cell resulting in effective loading of the MHC class I molecules.

126. The method of paragraph 121 wherein the peptide epitope is attached within the CDR region of the immunoglobulin or portion thereof.

127. The method of paragraph 121 wherein the immune response generates an effective T cell response to the antigen.

128. The method of paragraph 121 wherein the T cells are cytotoxic T lymphocytes.

129. The method of paragraph 121 wherein the dsRNA segment is selected from the group consisting of pA:pU and pI:pC.

130. The method of paragraph 121 wherein the peptide epitope is a T cell epitope.

131. The method of paragraph 121 wherein the peptide epitope is selected from the group consisting of influenza virus M1 or M2; hepatitis C virus NS3; hepatitis B virus core antigen; human papilloma virus HPV 18-E7, HPV 16-E7, HPV 18 E6, HPV 16 E6; melanoma-gp100; MART-1; TRP-2; carcinoembryonic antigen precursor; Her-2; tetanus toxin universal T helper epitope; HIV-1: reverse transcriptase; HIV1: gag; insulin precursor-human; human Gad 65; prostate tumor antigens; mucin 1; herpes simplex antigens; and, respiratory syncytial virus antigens.

132. The method of paragraph 121 wherein the immunoglobulin or portion and dsRNA segment thereof is administered by one of the methods selected from the group consisting of intravenous administration and bolus injection.

133. The method of paragraph 121 wherein the immunoglobulin or portion thereof and the dsRNA are administered in a pharmaceutically acceptable carrier.

134. The method of paragraph 121 wherein the method induces an effective memory response to the peptide epitope.

BRIEF DESCRIPTION OF THE DRAWINGS

FIG. 1C shows properties of selected human IgG backbone;

FIGS. 1E-1M show the sequences of various antigens and epitopes discussed in the present application and which can be inserted into an immunoglobulin [sequences can be accessed on the internet at ncbi.nlm.nih.gov (add the proper address prefix: http://www.) by searching the "proteins" section by use of the provided accession number. The content of this database is hereby incorporated by reference in its entirety.];

FIGS. 7A-7B show that the use of oil-in-water adjuvant (incomplete Freund's adjuvant, IFA) only modestly enhanced the in vivo formation of MHC-peptide complexes on APC of lymph nodes but not the spleen or thymus;

FIGS. 19A-19B show that in contrast to viral immunization with an influenza virus strain bearing the cognate peptide, Ig-mediated peptide delivery was ineffective in triggering cytotoxic response;

FIG. 23A shows an extensive library of synthetic RNA motifs;

FIGS. 30A-30B show that non-tagged pA:pU, but not non-tagged pI:pC, was able to compete out the binding of tagged pA:pU to human THP-1 monocytic cells;

FIG. 31 shows the purification and fractionation steps of dsRNA;

FIG. 32 shows that lower molecular weight fractions of a selected synthetic RNA compounds are endowed with different biological activity;

FIG. 33 shows that pI:pC but not pA:pU induced antibody response against itself, with a cross-reactive component against another RNA motif;

DETAILED DESCRIPTION OF THE INVENTION

Figure 1A:
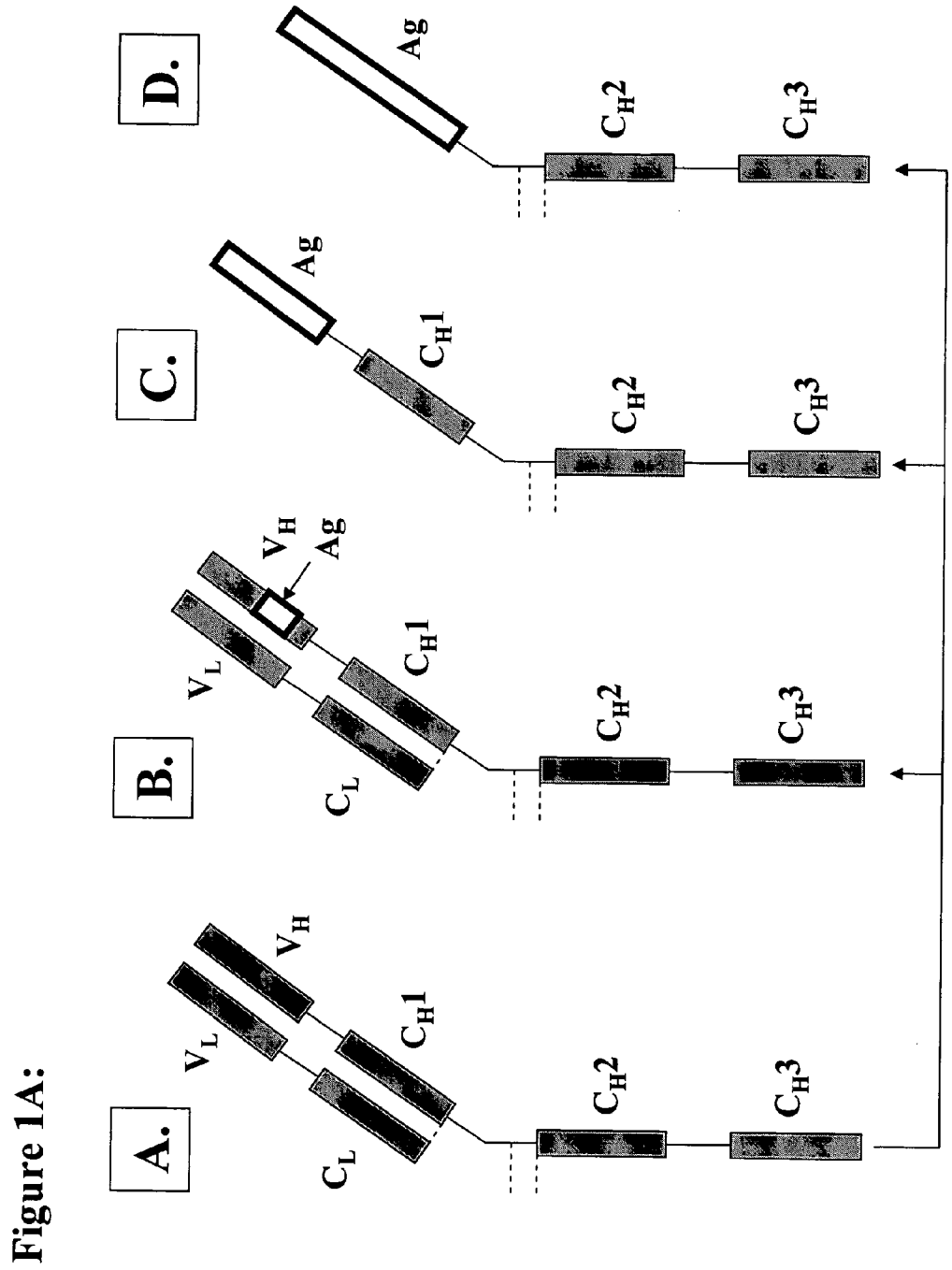
FIG. 1A shows (a) representation of natural IgG (light chain-heavy chain heterodimer); (B) antigen (Ag) derived peptide inserted within CDR (complementarity determining region) 3, 2, 1 or framework region; (C) VH (heavy chain, variable region) segment replaced with an antigen or fragment; (D) VH and CH1 segments replaced with antigen or antigen fragment.
Figure 1B:
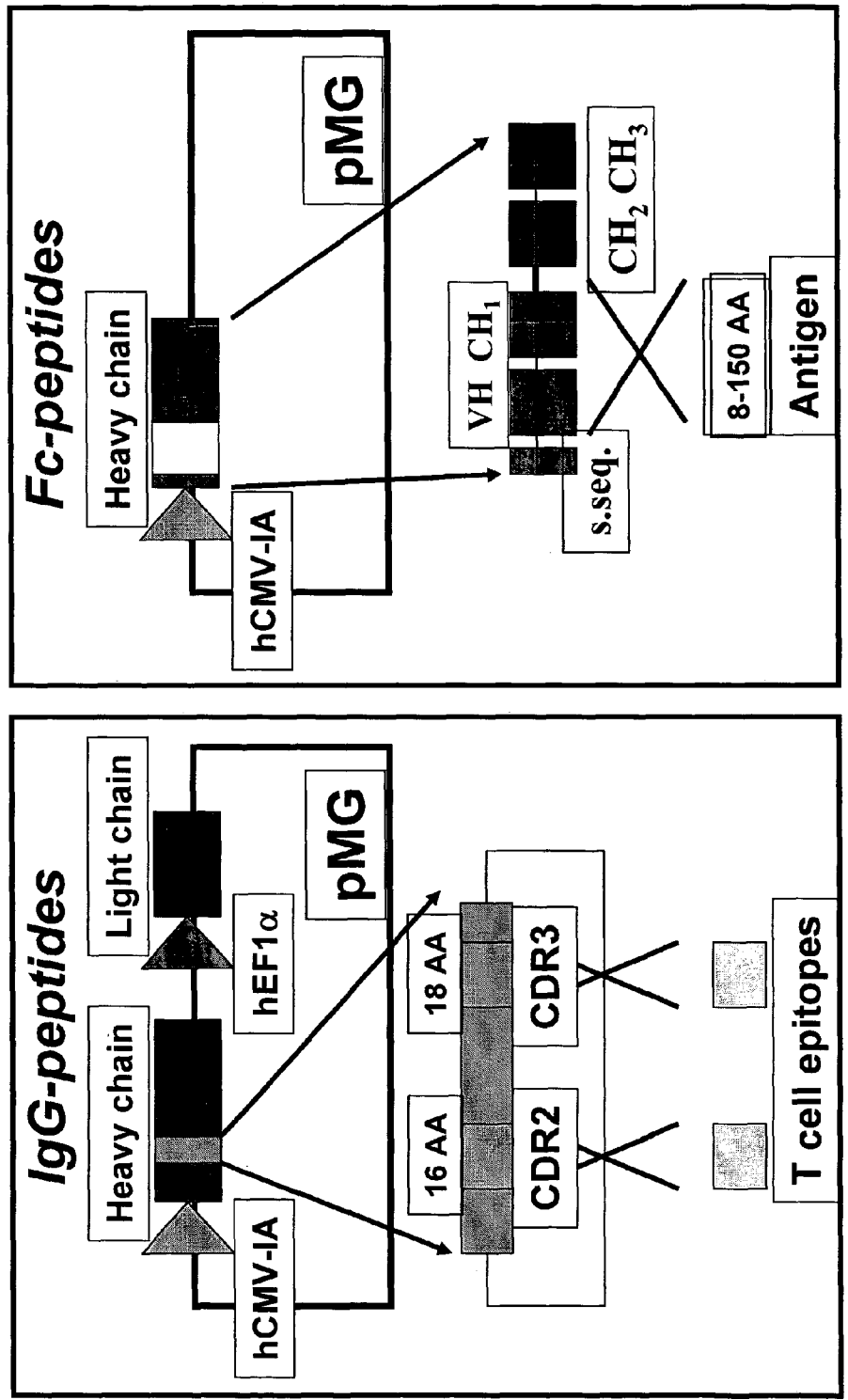
FIG. 1B illustrates diagramatically the IgG-peptide and Fc peptide.

Definitions:

The following definitions are intended to act as a guide and are not to be considered limiting of terms found throughout the specification:

adjuvant—a substance that enhances the adaptive arm of the immune response to an antigen;

adoptive transfer—transfer of a cell population from one animal to another of the same haplotype;

antigen—a molecule that can be specifically recognized by the adaptive elements of the immune system (B cells, T cells or both);

antigen presenting cell—heterogeneous population of leukocytes with very efficient immunostimulatory capacity;

BALB/C mouse—Widely distributed and among the most widely used inbred mouse strains;

B cell—a type of lymphocyte developed in the bone marrow. Each B cell encodes a surface receptor specific for a particular antigen. Upon recognition of a specific antigen, B cells multiply and produce large amounts of antibodies which in turn bind to the antigen which activated the B cell;

B cell unresponsiveness—antigen-specific lack of response by B cell;

CDR—Complementarity Determining Region; hypervariable regions in an immunoglobulin which create the antigen binding site. There are three CDR regions: CDR1, CDR2 and CDR3;

chemokines—a group of at least 25 small cytokines, all of which bind to heparin;

complete Freund's adjuvant—an oil-in-water emulsion containing mycobacterial cell wall components;

cross primed—antigen presenting cells that have acquired antigens from infected tissues and then present them to cognate T cells;

Dendritic Cells—A subtype of antigen presenting cells (i.e. CD11c+);

downregulation—decreasing the expression or activity of a particular compound or effect;

epitope—parts of an antigen which contact the antigen binding site of the antibody or T cell receptor;

FcγR—Ig receptors on cell surfaces of which there are three recognized groups: FcγRI (CD64), FcγRII (CD32) and FcγRIII (CD16);

heterodimer—dimeric protein consisting of 2 different protein sequences;

high zone tolerance—a state of unresponsiveness specific to a particular antigen that is induced upon challenge with a high concentration of said antigen;

IL-2—refers to interleukin-2;

IL-4—refers to interleukin-4;

Immunoglobulin—a group of glycoproteins present in the serum and tissue fluids of all mammals and are located on the surface of B cells and serve as antibodies free in the blood or lymph. There are five classes of immunoglobulins: IgG (70-75%), IgM (10%), IgA (15-20%), IgD (>1%) and IgE (found on basophils and mast cells in all individuals). IgG has four human subclasses (IgG1, IgG2, IgG3 and IgG4);

Immunoglobulin backbone—refers to an immunoglobulin molecule or portion thereof wherein at least one CDR region is able to receive an inserted peptide epitope;

immunoglobulin isotype switching—stimulation of B cells to switch production from one immunoglobulin isotype to another;

incomplete Freund's adjuvant—an oil-in-water emulsion not containing mycobacterial cell wall components;

innate immunity—The innate immune system provides broad relatively nonspecific host defenses that lack antigenic specificity but have the ability to guide acquired immunity. Among the cells types involved are dendritic cells and macrophages;

intraperitoneally—within peritoneal cavity;

intravenously—within vasculature;

isoforms—different glycosylation, phosphorylation, deamidation and other posttranslational modifications of proteins;

ITAM—immunoreceptor tyrosine-based activation motifs;

ITIM—immunoreceptor tyrosine-based inhibitory motifs;

macrophages—Any mononuclear, actively phagocytic cell arising from monocytic stem cells in the bone marrow;

MHC—refers to the Major Histocompatibility Complex;

modified immune response—enhanced or diminished immune response;

monocytes—Mononuclear leukocytes found in lymph nodes, spleen, bone marrow and loose connective tissue;

naive—non-differentiated, non-activated cell;

peptide—a compound consisting of two or more amino acids joined together by a peptide bond;

polynucleotide—a polymer of nucleotides;

professional antigen presenting cell—mature, able to present antigenic epitope;

recruitment—attraction of a cell population to inflammatory site;

secondary expansion—immune response which follows a second or subsequent encounter with a particular antigen;

self-antigens—antigens that are derived from the host;

subcutaneously—beneath the skin;

Tc1 immunity—Cytotoxic T cell type 1, CD 8+;

Th1 cells—T helper 1 cells which are involved in cell mediated inflammatory reactions, identified by production of IFNγ, TNFβ and IL-2;

Th2 cells—T helper 2 cells which encourage production of antibodies and are identified by production of IL-4 and IL-5;

Th3 cells—T helper regulatory cell, known to produce transforming growth factor (TGF)-beta;

TR1 cells—T regulatory, cell, known to produce interleukin 10; and, upregulation—enhancement of expression or activity of a particular compound or effect;

Materials and Methods

For selective in vivo loading of antigen presenting cell subsets, the use of compounds described schematically in the FIG. 1A are used: (A) representation of natural IgG (light chain—heavy chain heterodimer); (B) antigen (Ag) derived peptide inserted within CDR 3, 2, 1 or framework region; (C) VII segment replaced with an antigen or fragment; and, (D) VII and CH1 segments replaced with antigen or antigen fragment. This type of molecules are engineered using methods known in the art and as stated as follows:

Construction of Model Recombinant IgG.

Polymerase chain reaction (PCR) mutagenesis was used to replace the CDR3 region of VII chain with the stated epitopes. Briefly, a pUC19 plasmid harboring the 5.5-kb EcoRI fragment carrying the VH gene of the murine anti-arsonate antibody, 91A3, was used as template DNA in two PCRs to delete the diversity segment (D) of the complementarity-determining region 3' (CDR3) loop and inserted DNA fragments encoding various antigen epitopes. These chimeric VII and as well as wild type VH genes were then ligated with Ig gamma 1 heavy chain constant region within the plasmid pSV2ΔHgptDNSVH-hCgamma1 from which the EcoRI dansyl (dns)-conjugated VH gene was cut out. The sequences of VH and inserted epitopes were confirmed by. DNA sequencing. To express these chimeric IgGs with murine 91A3 VH-human C gamma1 heavy chain genes and a mouse-human chimeric k light chain gene, an 8-kb BamHI fragment encoding the entire murine 91A3 kappa light chain gene was subcloned into the BamHI site of pUC19 plasmid. Subsequently, a HindIII fragment with the kappa light chain promoter and the V kappa region coding sequences was cut out from this plasmid and subcloned into the HindIII site of pSV184ΔHneoDNSVk-hCk upstream of the gene encoding a human k light chain C region (Ck) from which the dns-conjugated Vk (dnsVk) had been excised. This plasmid, which will encode a murine 91A3 Vk-human Ck light chain, is designated pSV184Δhneo91A3'Vk-hCk.

Construction of Human Recombinant IgG.

The human IgG backbone was obtained from IgGA1 myeloma cell line by RT-PCR. The recombinant human IgG was cloned by inserting the stated epitopes to replace the CDR2 or CDR3 regions of the human IgG1 backbone. Briefly, T cell epitopes were created by PCR mutagenesis and subcloned into the CDR2/CDR3 region. The recombinant heavy chains were then subcloned into pMG vector (Invivogen, San Diego, Calif.) by BamHI and XbaI sites. The heavy chain expression was controlled by the hCMV promoter. In parallel, the human kappa light chain was subcloned into the pMG vector by StuI and NheI sites. The expression of the light chain was controlled by an EF-1 alpha and HTLV-1 LTR hybrid promoter. The double expression vector carrying both the recombinant heavy chain and light chain were then transfected into expression cell lines.

The Fc-peptides were constructed by cutting off the VH and CH1 fragment and replacing it with stated viral or tumor antigens (8-150 Aas). Briefly, the human IgG1 heavy chain was subcloned into pCDNA3 vector by EcoRI and XhoI sites. Then the stated antigens are inserted between the leader sequence and hinge region of IgG1 by PCR mutagenesis. To increase the flexibility of the fused antigens, an oligo-glycine linker (5 glycines) was added after the antigen. The expression of human IgG recombinant molecules can be performed by using either one of the strategies displayed in FIG. 1B.

The human IgG backbone has been selected rationally, based on the ability to bind to FcγR, complement and cytokine activation in various states. Properties of selected human IgG backbone are shown in the FIG. 1C and the sequence of the constant region of the heavy chain as well as the schematic depiction of a prospective construct, is shown in FIG. 1D.

Figure 1D:
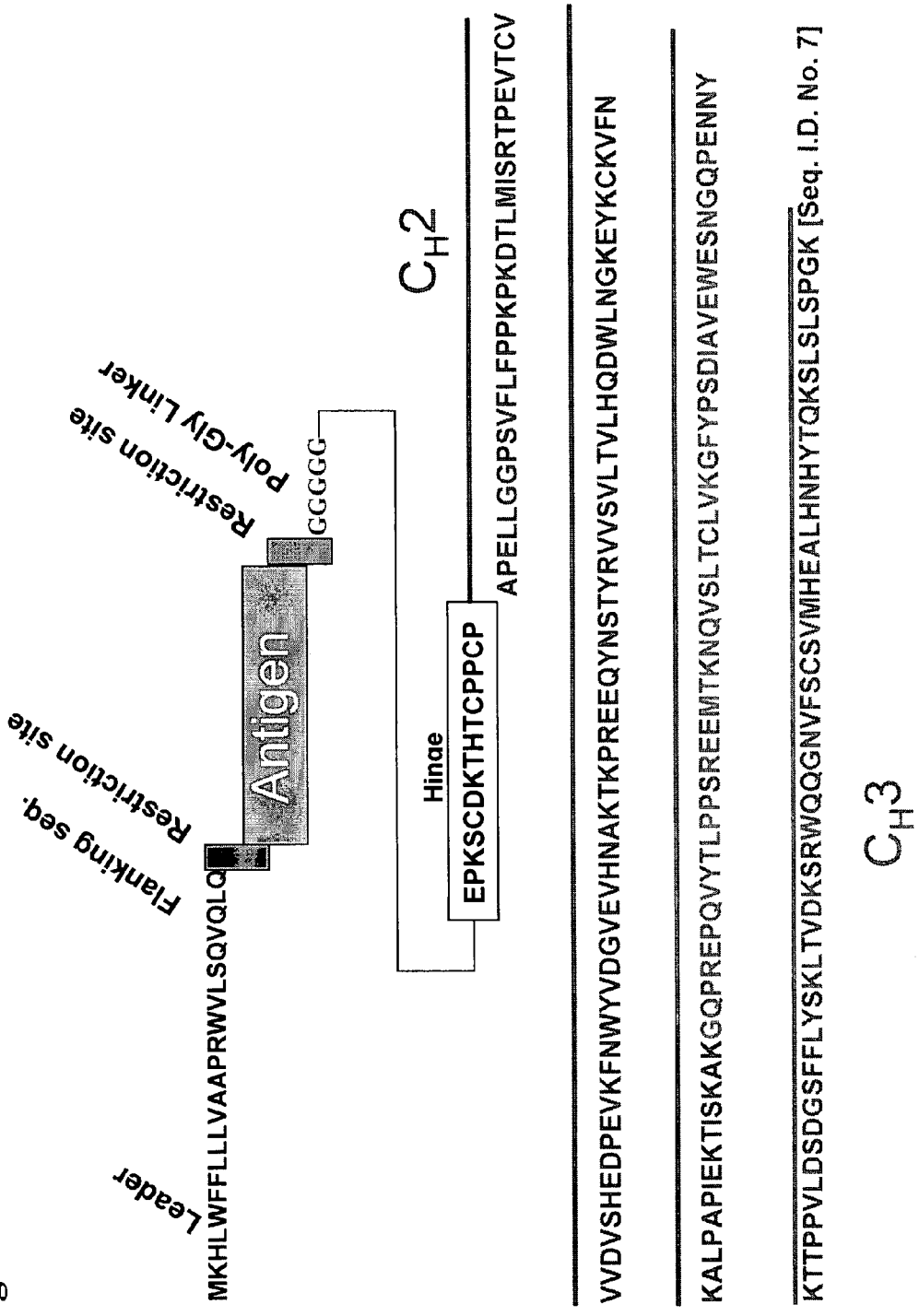
FIG. 1D shows the sequence of the constant region of the heavy chain as well as schematic depiction of a prospective construct.

Epitopes used for model recombinant IgG are shown in FIG. 1E (mouse MHC class II-restricted HA epitope and mouse MHC class I restricted NP epitope). The nomenclature of recombinant constructs is recIgG-epitope (HA or NP)-restriction element (I-Ed or Kd, respectively). In short, they may be referred to as IgHA or IgNP. Model molecules comprising defined mouse self epitopes (MBP or PLP derived) were similarly constructed. The sequence of the variable region of the heavy chain of anti-arsonate antibody used as the backbone has been depicted in FIG. 1E and the technology is well known in the art (Zaghouani et al., Science 1993 Jan. 8; 259(5092):224-7) the contents of which is hereby incorporated by reference.

In FIGS. 1E-1M, examples of antigens and epitopes (in bold) are provided that could be inserted (larger parts up to 150 AA spanning one or multiple epitopes) or attached to the backbone. Such constructs comprising the shown antigens/epitopes may be used as drugs against infectious or tumoral diseases. In FIG. 1I there is the HLA-A2 anchor motif displayed, that allows the prediction of location of potentially therapeutic cytotoxic epitopes in any protein, facilitating the selection of the antigen fragment to be used in the recombinant immunoglobulin.

In FIG. 1J, examples of "universal" T helper epitopes (Kumar et al. J Immunol 1992 Mar. 1; 148(5):1499-505) are provided, both dominant and promiscuous from the point of view of MHC restriction, that could be used for construction of composite molecules for the purpose of inducing or enhancing immunity to MHC class I-restricted epitopes, using compounds such as:

[antigen fragment]-[universal Th epitope]-Fc(IgG).

Examples of such constructs are schematically represented in FIG. 1K (bottom).

In FIG. 1K top, examples of human self antigens with epitopes bolded are shown, that could be used to generate recombinant IgG molecules against autoimmune/inflammatory disorders.

In FIGS. 1L and 1M other antigen sequences that could be used for the construction of above mentioned immunoglobulin constructs are shown. The antigen fragments of interest could be defined by using methods to predict MHC class I epitopes (Lim et al., Mol Immunol. 1996 February; 33[2]: 221-30).

Production of Recombinant IgG

The SP2/0 cell line (American Type Culture Collection) is used for the production of all the recombinant IgGs (rIgG) discussed in this patent application. Stable expressing cell lines (i.e. transfectomas) were produced using a double transfection protocol with plasmids encoding the heavy and light chains of an anti-arsenate mouse IgG. Each transfectoma differs only in the sequence of the CDR3 region of the heavy chain. Methods for growing the cell lines as well as producing the different purified rIgG used in the experiments reported in this application are identical in all cases.

The SP2/0 transfectomas were initially grown in Quantum Yield media (BD Biosciences) supplemented with 5% (v/v) heat-inactivated fetal bovine serum, 0.5 mg/mM gentamicin and 2.5 µg/mL Fugizone. Cultures were maintained at 37° C. in a humidified CO2 incubator. Efforts were made to adapt each of the cell lines to growth in different commercially available serum-free medias (Lymphocyte Growth Media 2, Clonetics; Cell MAb Growth Media Serum Free, BD Biosciences; Animal Component Free Cell Media, BD Biosciences). Each of the serum-free medias was supplemented with antibiotics as above. Culture media containing secreted IgG was produced from each media noted above. No difference in the IgGs produced in the different medias was observed over the course of this work (molecular weight analysis by SDS PAGE [see below], ELISPOT assays, and immune responses in mice).

The amount of secreted rIgG was quantitated using an ELISA: capture antibody was a goat anti-mouse IgG (Sigma) and secondary antibody was an anti-mouse IgG HRP conjugate (Sigma). Purified mouse IgG (Sigma) was used as a standard.

Four different methods have been used to produce media containing the different rIgGs (i.e. conditioned media, "CM"): flasks, stirred vessels, packed bed bioreactors (New Brunswick Cellagen), CELLine flasks (BD Biosciences). In the case of CM produced in flasks, the cells were fed and/or harvested twice a week and maintained at least 50% viability, but viability was generally greater than 70%. Collected media was filtered and held at 4 C. Stirred vessels (1 L) were seeded at $10^6$ cells per mL in 200 mL starting volume. Media was added weekly to keep the cell number between $10^7$ and $10^6$ per mL until 800 mL of total volume was reached. At this point cell viability was determined (typically greater than 80%), and the run was continued until such time that the viability fell below 50%. Media was then collected and sterile filtered to remove cells and held at 4° C. For the packed bed bioreactors: each unit was seeded with approximately $10^8$ cells in 400 mL of media; maintained in a $CO_2$ incubator at 37° C. with constant stirring; media was changed every 3-4 days and CM was filtered as above; production of rIgGs in the CM was monitored with ELISA. Bioreactor runs were continued until production of rIgGs began to decline or the vessel became contaminated. The 1 L CELLine flasks were used according to manufacturer's instructions.: each flask was seeded with $10^7$ to $10^8$ cells in a total volume 40 mL in the cell compartment; 1 L of media was added to the feed compartment; CM was harvested from the cell chamber after 2 to 3 weeks, or when viability of the cells fell below 20%.

Purification of rIgG

The rIgGs produced by the above methods were purified by one of two methods. For CM that contained FBS, an anti-mouse IgG immunoaffinity resin was used. The immunoaffinity resin was synthesized using the following protocol: 10 mL of cyanogen bromide-activated Sepharose 4B (Sigma) was washed with 1 mM HCl as per manufacturer's instructions; 10-20 mg of goat anti-mouse IgG (Sigma) was dissolved in coupling buffer (0.1 M sodium carbonate [pH 8.4]/ 0.5 M NaCl) at a concentration of 2 mg/mL; the IgG solution was added to the washed resin, and the slurry was mixed end-over-end at room temperature; the extent of coupling was monitored using the Bradford assay to determine the amount of remaining soluble IgG; the coupling was quenched by addition of ethanolamine to a final concentration of 10 mM when the amount of soluble IgG was less than 10% of the starting concentration (approximately 45 minutes). The immunoaffinity resin was then washed with the following buffers: PBS, 10 mM glycine (pH 2.4), 20 mM Tris/1 M NaCl (pH 8.0), PBS. The resin was stored at 4° C. in PBS. The protocol for purifying rIgG with this resin was initiated by passing CM through the column at 1 to 2 mL/min. The resin was then washed free of nonbound protein using the following protocol: 100 mL PBS/0.5M NaCl followed by 50 mL 1 mM Tris (pH 8). Fractions were monitored for protein using the Bradford assay. Specifically bound rIgG was eluted with a low pH buffer (5 mM glycine (pH 2.4)/0.5 M NaCl). The eluted protein was collected and held at 4° C. for further processing (see below).

The rIgG produced in serum-free culture media was purified using Protein A affinity chromatography. Typically, a 5 mL rProtein A column (HiTrap rProtein A FF from Amersham Pharmacia Biotech) was equilibrated with PBS and the sample was run through the column at 2 mL/min using a FPLC unit (Pharmacia). The resin was washed free of non-specifically bound protein with PBS, followed by 20 mM Tris (pH 8.0)/1 M NaCl, then water. The specifically bound rIgG was eluted with 1 mM glycine (pH 2.4). The eluted peak was collected and held at 4 C for further processing.

Generally, the rIgG fractions were pooled and concentrated using Centricon . ultrafiltration units (Amicon) to a final concentration of 1 to 4 mg/mL (Bradford assay with IgG as standard). The concentrated fraction was then dialyzed into 1 mM glycine (pH 2.4), the final concentration determined by $A_{280}$ using an extinction coefficient of 1.4 for a 1 mg/mL IgG solution, and aliquoted into 100 µl fractions that were stored in the −80° C. freezer. The purified rIgGs were analyzed for structural integrity and purity by SDS gel electrophoresis. The gels were stained with Coomassie blue (Pierce Chemical). In all cases the rIgGs used in the reported experiments displayed their expected molecular weight (reduced and non-reduced) as compared to protein standards and control IgG. Generally, the purified rIgG was greater than 95% pure as determined by visual inspection of the stained bands relative to the bands of known amounts of control IgG run on the same gel.

RNA Segments

The double stranded RNA (dsRNA) or single stranded RNA (ssRNA) segments of the present invention can be made according to the following method (and are available commercially): 1) ssRNA: The polynucleotides (polyA, polyU) are enzymatically prepared, using nucleotides and polynucleotide-phosphorylase, with no animal-sourced material entering into its preparation process. 2) dsRNA: Annealing of polyadenylic acid (polyA or pA) with polyuridylic acid (polyU or pU).

Figures 8A, 8B, 8C, 8D:
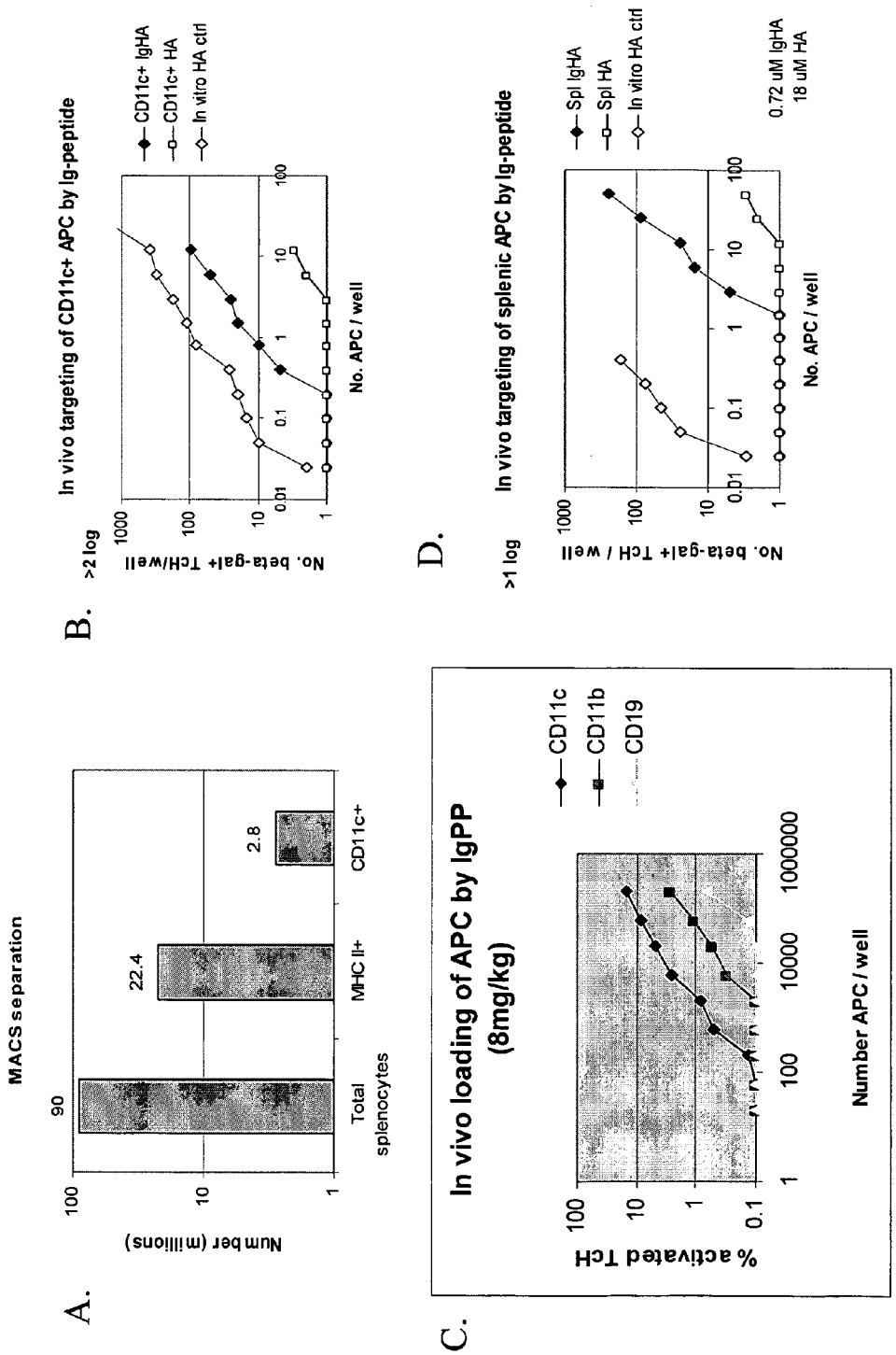
FIGS. 8A-8D show that use of FcγR mediated delivery of peptides results in preferential formation of immunogenic MHC II–peptide complexes on CD11c+ and CD11b+ APC.

In general, the dsRNA and ssRNA of the present invention are homopolymers with, in the case of dsRNA, a single base or nucleotide (e.g., adenine) consistently forming one strand with its complement consistently forming the other strand. In the case of ssRNA, the single strand is consistently made of the same nucleotide. However, it is within the scope of the invention to use dsRNA or ssRNA compositions that are made up of mixed nucleotides (and without or without their complements in the case of dsRNA). For example, a polyA: polyU dsRNA segment with occasional substitution by an a non-complementary nucleotide (e.g., guanine, cytosine or inosine). The dsRNA and ssRNA compositions of the present invention are comprised of the bases/nucleotides adenine (A), guanine (G), cytosine (C), uracil (U) and inosine (I) and could also be comprised of a small percentage of the DNA base thymine (T). The RNA compositions in Table I and FIG. 8A is descriptive of various RNA compositions used in the Examples. The RNA compositions of the present invention were prepared and purified according to Example 30.

The various RNA strands used in the present invention are generally between 100-2000 base pairs in length but may be between 1-20, 20-40, 40-60, 60-80, 80-100, 1-100, 100-200, 200-300, 300-400, 400-500, 500-600, 600-700, 800-900, 1000-1100, 1100-1200, 1200-1300, 1300-1400, 1400-1500, 1500-1600, 1600-1700, 1700-1800, 1800-1900, 1900-2000, 2000-2100, 2100-2200, 2300-2400, 2400-2500, 2500-3000, 3000-4000, 4000-5000, 5000-10,000 base pairs and greater than 10,000 base pairs in length and/or mixtures thereof.

EXAMPLE 1

Shows that a significant factor limiting the activity, of peptides that encompass T cell epitopes is the poor pharmacokinetics resulting in reduced in vivo loading of APC.

Antigen presenting cells ("APCs") from 1 naïve BALB/c mouse were obtained from splenic tissue. Following washing, three million APC were incubated with 13.5 nM HA 110-120 peptide for 3 hours at 37° C., in 1 ml of HL-1 medium. The cells were washed, divided into three equal inoculi and injected (½ subcutaneously+½ intraperitoneally) into 3 naïve BALB/c mice. The mice were sacrificed 2 weeks later and the immune response measured against HA 110-120 peptide, by. ELISPOT analysis as follows: the ELISPOT plates (Millipore, Molsheim, France) were incubated with purified anti-cytokine Abs (4 ug/ml for anti-IL2 and anti-IL4, and 8 µg/mg for anti-IFN gamma, from BD Pharmingen) in sterile PBS (50 µl/well) at 4° C. overnight. The next day, the plates were washed 2 times with DMEM media and blocked with 200µl/well of DMEM complete containing FBS, for an hour at 37° C. Single cell suspension was made from the spleens, red blood cells were lysed, cells washed, counted and incubated at $5 \times 10^5$/well together with 20 µg/ml HA 110-120 peptide or just with media, to assess the background.

Plates were incubated 72 hours at 37° C., 5% CO2. After 3 days, plates were washed 5 times with PBS—tween 20 0.05% (washing buffer), and incubated with 100 µl/well of biotinylated anti-cytokine Abs, 2 µg/ml in PBS—tween 20 0.05% —FBS 0.1% (ELISPOT buffer) overnight at 4° C. The next day, the plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. Plates were then allowed to dry at room temperature for 24 hours. The data were acquired using an automated system (Navitar, Rochester, N.Y.) with ImagePro-Plus) software (Media Cybernetics, Silver Spring, Md.). In parallel, 3 naïve BALB/c mice were each injected with 4.5 nM of HA peptide in sterile PBS, half of it administered subcutaneously and half of it intraperitoneally. The mice were sacrificed 2 weeks later and the T cell response characterized as above, by ELISPOT analysis.

Figure 2A:
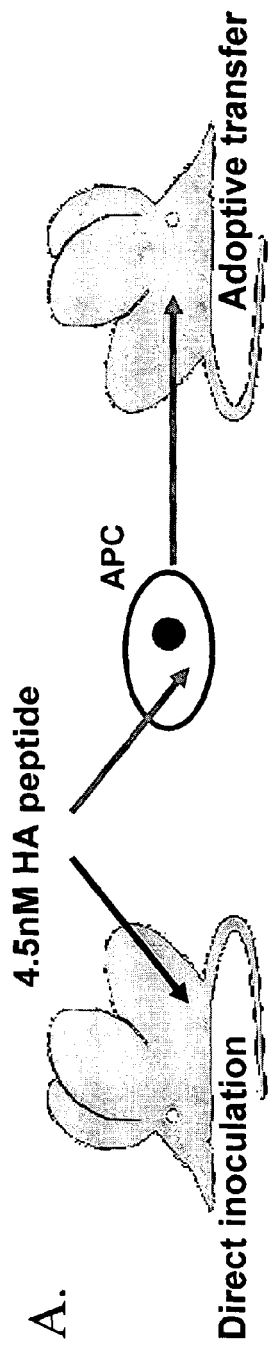
FIGS. 2A-2B show that while the injection of the peptide epitope in saline was not immunogenic, a similar dose of peptide used for ex vivo loading of APC effectively triggered a substantial immune response upon adoptive transfer.
Figure 2B:
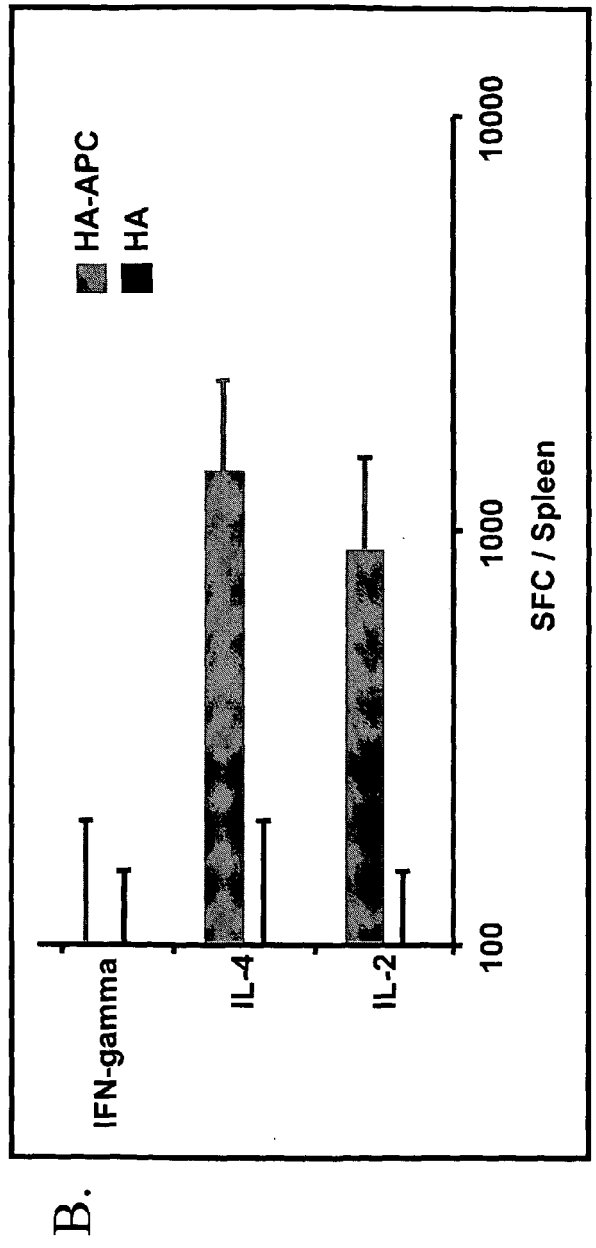

In FIG. 2(A), the experimental protocol is described. In FIG. 2(B), the results of the experiment are shown: they were expressed as number of IFN-γ, IL-2 and IL-4 spot forming colonies/spleen, after the subtraction of the background (mean±SEM). "HA-APC" corresponds to antigen presenting cells (dendritic cells) loaded ex vivo prior to adoptive transfer. "HA" corresponds to peptide directly injected into animals.

The results described in the FIGS. 2A -2B show that while the injection of the peptide epitope in saline was not immunogenic, a similar dose of peptide used for ex vivo loading of APC effectively triggered a substantial immune response upon adoptive transfer. This shows that if directly injected, the peptide does not effectively reach APC, a prerequisite for effective induction of an immune response.

EXAMPLE 2

Demonstrates that incorporation of a peptide epitope within the IgG ameliorated its pharmacokinetics profile.

BALB/c Scid mice (3/group) were injected intravenously with 60 nM of SFERFEIFPKE ("HA") [Seq. I.D. No. 5]

peptide or 2.4 nM of recHA (I-Ed)-IgG ("Ig-HA") and blood was harvested at various intervals. Serum was immediately separated and promptly frozen at −70° C. Later, the serum samples were incubated with $2\times10^4$ cells/well/50 µl HA-specific T cell hybridoma (TcH) and $1\times10^4$ cells/well/50 µl M12 B cell lymphoma APC, in serum free HL-1 medium at 37° C. and 5% $CO_2$ for 24 hours. The next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the $_p$late, cells washed once with PBS 200 ul/well, centrifuging the plate for 3min/4° C./1500 RPM. PBS was flicked off the plate and cells were incubated overnight at 37° C. with 200 µl/well of the X-gal substrate freshly prepared as follows: 200 µl of the X-gal stock solution, (40 mg/ml in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope.

The activation of TcH was represented as function of time post-injection. The epitope could be detected in the blood only in the case of mice injected with recHA(I-Ed)-IgG, for an interval of about one day. In contrast, the HA peptide injected as is, was not detected in the periphery despite being used in large molar excess (25 fold).

Figure 3:
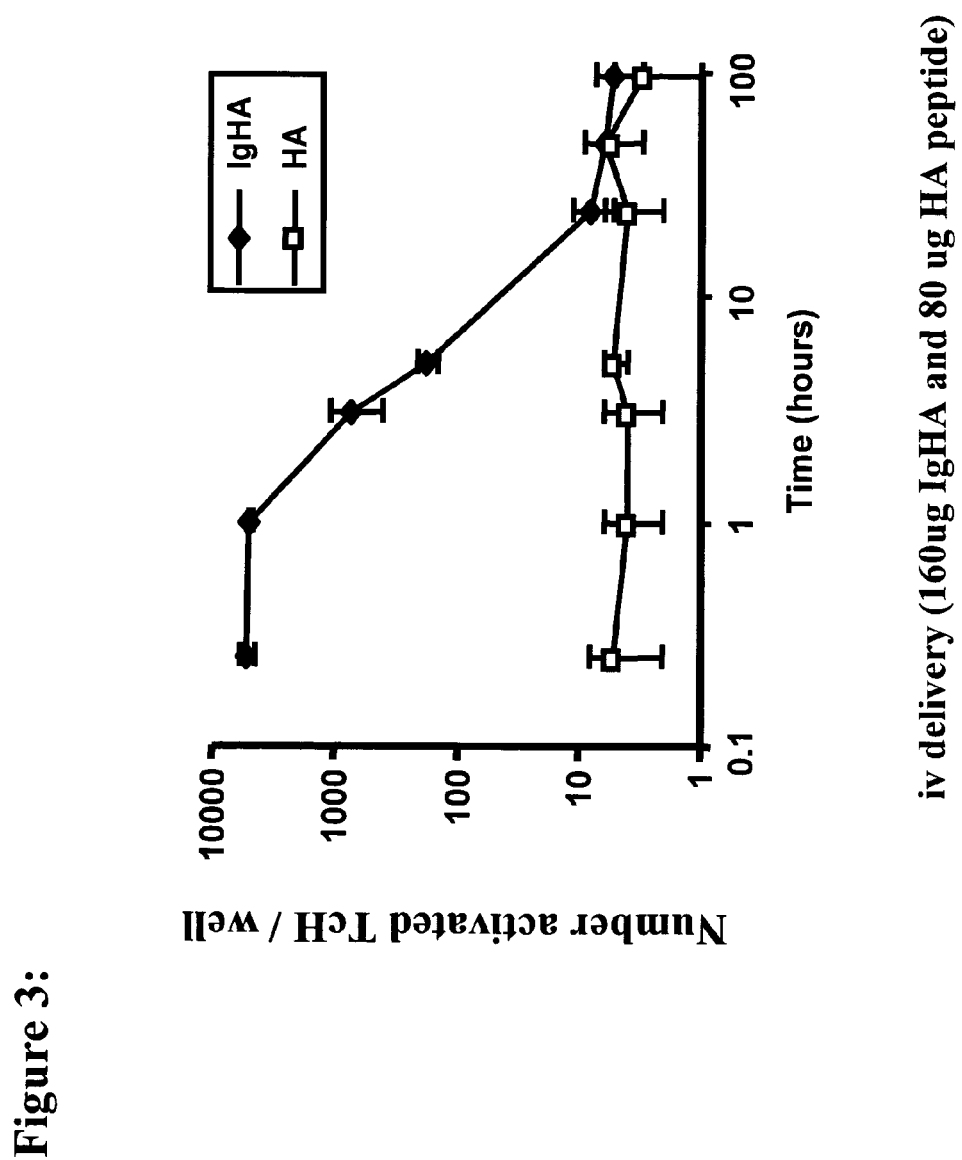
FIG. 3 shows that delivery of epitope within Ig backbone considerably favored its stability in the systemic circulation.
Figure 4A:
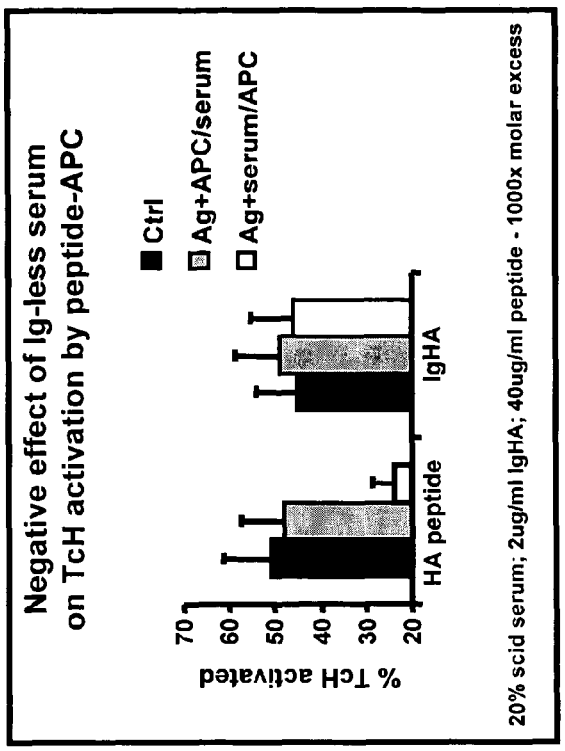
FIGS. 4A-4B show that pre-incubation of peptide with serum resulted in decreased TcH activation.
Figure 4B:
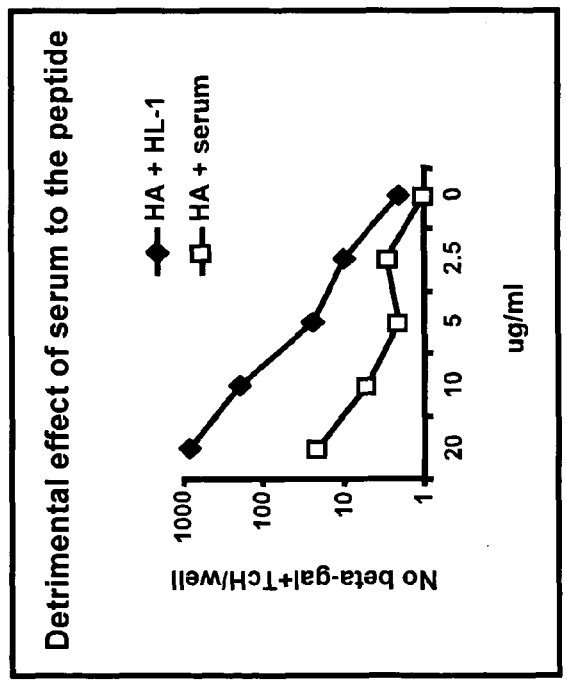

Thus, the results described in the FIG. 3 show that delivery of epitope within Ig backbone considerably favored its stability in the systemic circulation.

EXAMPLE 3

Shows that a peptide encompassing a T cell epitope is ineffectively presented by APC to specific T cells in the presence of serum and this is corrected by incorporation of the peptide epitope within the IgG backbone FIG. 4(A) shows the detrimental effect of serum on the presentation of a T cell epitope peptide: M12 B cell lymphoma APC were incubated with TcH in the presence of various amounts of SFERFEIFPKE (HA) peptide in serum-free HL-1 medium ("HA+HL-1") or HL-1 medium supplemented with 20% mouse serum from BALB/c scid mice ("HA+serum"). The number of cells incubated was $2\times10^4$ M12 and $1\times10^4$ TcH/100 µl of HL-1 medium supplemented or not with serum. The next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 µl/well, centrifuging the plate for 3 min/4° C./1500 RPM. PBS was flicked off the plate and cells were incubated overnight at 37° C. with 200 µl/well of the X-gal substrate freshly prepared as follows: 200 ul of the X-gal stock solution, (40 mg/ml in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope.

The serum negatively interfered with the formation and/or presentation of immunogenic MHC-peptide complexes.

FIG. 4B: the serum negatively interfered with the formation and/or presentation of immunogenic MHC-peptide complexes.

This phenomenon was further studied by sequential incubation of peptide ("HA peptide") or recHA (I-Ed)-IgG ("IgHA") first with APC or serum, followed by addition after 1 hour of TcH and serum, or APC and TcH, respectively. Control corresponds to cells incubated with antigens in the absence of added serum ("Ctrl"). The number of cells incubated was $2\times10^4$ M12 and $1\times10^4$ TcH/100 µl of HL-1 medium supplemented or not with serum. The next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 µl/well, centrifuging the plate for 3 min/4° C./1500 RPM. PBS was flicked off the plate and cells were incubated overnight at 37° C. with 200 µl/well of the X-gal substrate freshly prepared as follows: 200 µl of the X-gal stock solution, (40 mg/ml in DMSO) in 10 ml substrate buffer (5 mM Potassium Ferrocyanide, 5 mM Potassium Ferricyanide, 2 mM MgCl 2 in 1× PBS). The blue activated TcH were scored visually using the microscope.

The results were represented as percentage of activated T cells (beta-gal$^+$ TcH)/well at concentrations of 2 µg/ml of recHA (I-$E^d$)-IgG ("IgHA") or 40 µg/ml of HA peptide (1,000 molar excess relative to the recombinant Ig).

The results described in the FIG. 4 show that pre-incubation of peptide with serum resulted in decreased TcH activation. Addition of serum after APC pulsing did not have an effect on TcH activation. In contrast, the formation of MHC-peptide complexes was not impaired by serum when the recombinant immunoglobulin carrying the peptide was used instead of the peptide alone.

EXAMPLE 4

Shows that incorporation of a T cell peptide epitope within an IgG backbone improves its presentation to specific T cells by APC, with a rate depending on the nature of APC.

As shown in FIG. 5A, ex vivo formation of MHC-peptide complexes on antigen presenting cells (APCs) from spleen was measured as follows: splenic APC were isolated by magnetic sorting using anti-MHC II antibodies. Separation by using magnetic beads coupled with anti-MHC II was carried out using magnetic cell separators and reagents from Miltenyi Biotec, Germany as follows: spleens were processed to single cell suspension, red blood cells lysed, then cells washed, counted and resuspended in MACS buffer (PBS supplemented with 2 mM EDTA and 0.5% BSA). Magnetically labeled cells were passed through a separation column which is placed in the magnetic field of a MACS separator. The magnetically labeled positive fraction is retained in the column while the negative fraction runs through. After removal of the column from the magnetic field, the magnetically retained positive cells are eluted from the column, cells are washed, counted, resuspended in HL1 complete media and they were incubated with specific T cell hybridoma recognizing I-$E^d$+SFERFEIFPKE overnight, in the presence of various amounts of SFERFEIFPKE ("HA") peptide or recHA(I-Ed)-IgG ("IgHA"). Per well, $2\times10^4$ APC were incubated with $1\times10^4$TcH. Next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 µl /well, centrifuging the plate for 3 min/4° C./1500 RPM. PBS was flicked off the plate and cells were incubated overnight at 37° C. with 200 µl/well of the X-gal substrate freshly prepared as follows: 200 µl of the X-gal stock solution, (40 mg/ml in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope. The number of activated TcH was quantified and the results expressed as activation versus molar amount of epitope.

(B) A protocol similar to that described above has been applied to M12 B cell lymphoma APC.

Figures 5A, 5B:
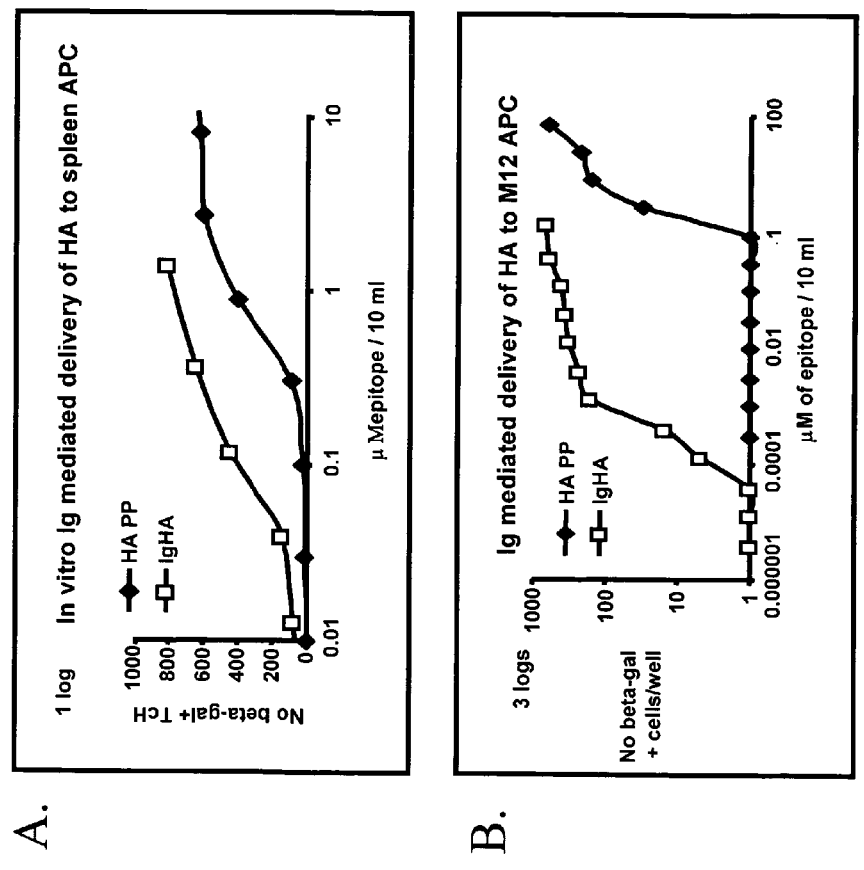
FIGS. 5A-5B show that the relative efficiency of MHC-peptide complex formation greatly varied depending on the nature of antigen and APC.

Thus, the results described in the FIG. 5B show that the relative efficiency of MHC-peptide complex formation greatly varied depending on the nature of antigen and APC. On a molar basis, the peptide epitope within the IgG backbone was 10 times more effectively handled by MHC II+APC from lymphoid organs and 1000 times more effectively handled by transformed B cell lymphoma cells, as compared to the free peptide itself. Thus, the cellular handling of the epitope and formation of MHC-peptide complexes subsequent to delivery within IgG, greatly varies with the nature of APC.

EXAMPLE 5

Shows that FcγR-mediated delivery of a peptide encompassing a T cell epitope results in more effective cellular handling and presentation by cell populations (peripheral blood white Cell) containing reduced numbers of professional APC.

Figures 6A, 6B:
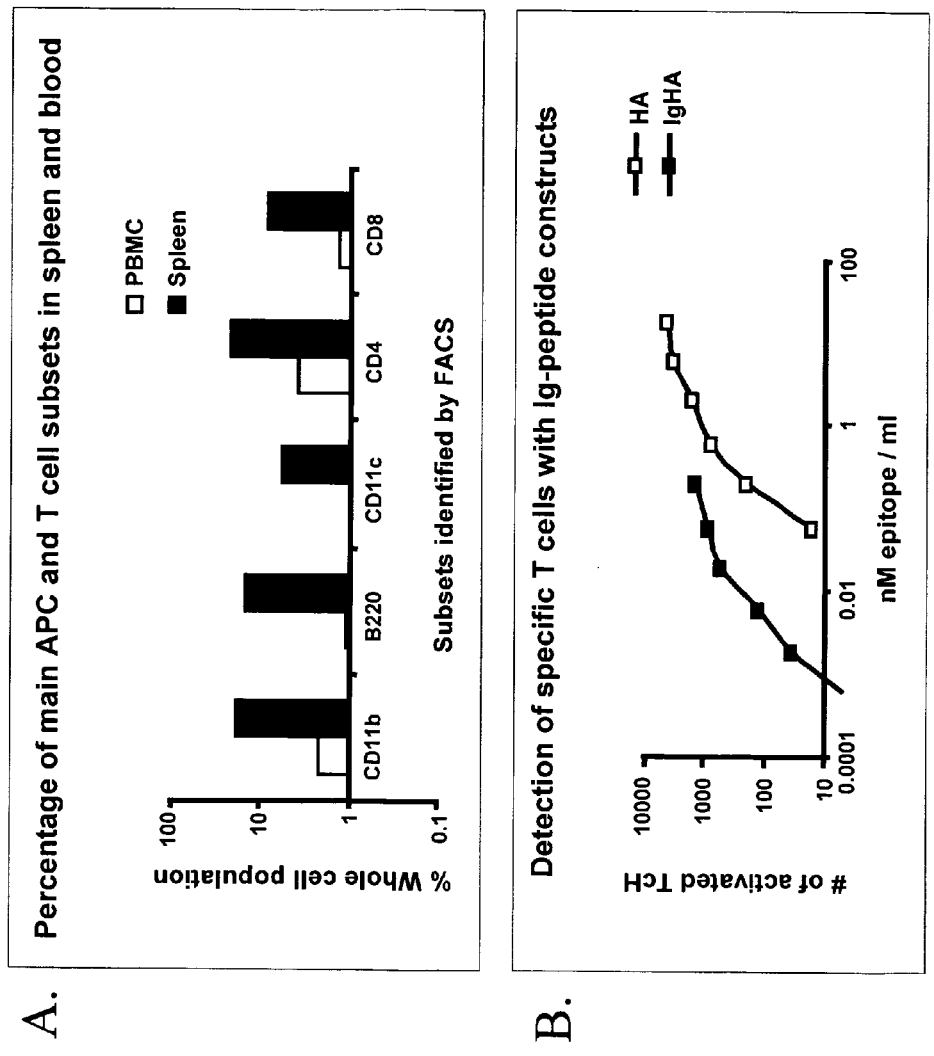
FIGS. 6A-6B show that the peptide epitope within IgG backbone was more effective on a molar basis (1 order of magnitude) than the peptide alone in inducing TcH activation when handled by blood-derived APC.

(A) To quantify the APC, peripheral blood mononuclear cells (PBMC) were separated by Ficoll gradient centrifugation from BALB/c mice and FACS analysis for expression of CD11c, CD11b and B220 was carried out. The results are represented in FIG. 6A as percentage of APC and T cells in blood versus a prototype secondary lymphoid organ (spleen). The number of professional APC such as CD11c+ cells is tremendously (2 logs) decreased in blood as compared to spleen. B220+ and CD11b+ cells were decreased as well (1 order of magnitude). The following materials and methods were used.

Materials:
  Ficoll: Ficoll-hypaque (1.077, Amersham, cat #17-1440-02)
  Antibodies: CD11b cat #01715A, CD11c cat #557401, 13220 cat #01125A, all PE conjugated (BD PharMingen)
  Flow Cytometer: FACSCalibur, Becton Dickinson
  FACS Buffer: PBS, 1% FCS, 0.1% sodium azide.

Methods:
  1. Animal blood was harvested and mononuclear cells were separated by Ficoll gradient separation.
  2. Cells were suspended and labeled with fluorescently-tagged anti-mouse CD-11c, CD11b or B220 at 2 ug/ml for 20 minutes on ice
  3. Cells were washed once and resuspended in 300 ul of FACS buffer
  4. Flow cytometric analysis was carried out to determine fractions of total cell population which labeled with each specific antibody (B) PBMC were used as APC with SFERFEIFPKE (HA)-specific TcH, in the presence of cognate peptide or recHA (I-Ed)-IgG. The cells were co-incubated for 24 hours ($2\times10^4$ APC+$1\times10^4$ TcH). The next day the plate was centrifuged for 15 min/4 C/1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 µl/well, centrifuging the plate for 3 min/4° C./1500 RPM. PBS was flicked off the plate and cells were incubated overnight at 37° C. with 200 µl/well of the X-gal substrate freshly prepared as follows: 200 µl of the X-gal stock solution, (40 mg/ml in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope. The results are expressed as number of activated TcH/well, at different molar concentrations of epitope.

The results described in the FIGS. 6A-6B show that the peptide epitope within IgG backbone was more effective on a molar basis (1 order of magnitude) than the peptide alone in inducing TcH activation when handled by blood-derived APC, suggesting that in suboptimal conditions associated with limiting numbers of professional APC, the Ig backbone greatly facilitates the creation of MHC-peptide complexes.

EXAMPLE 6

Shows that delivery of a T cell epitope within IgG backbone dramatically improves the loading and presentation of epitope by APC in the secondary (draining lymph nodes+spleen) but not central lymphoid organs. The emulsification of the peptide epitope in IFA or increase of dose 100 fold could not reproduce the same degree of loading. Thus, epitope insertion within the IgG backbone removes limiting factors associated with peptide-based strategy, that cannot be otherwise compensated by dose escalation or depot effect.

Assessment of in vivo formation of MHC-peptide complexes and a comparison with peptide in saline or standard oil-in-water emulsion were carried out in I-Ed$^+$ BALB/c mice. BALB/c mice were treated with recHA (I-Ed)-IgG, peptide in saline or peptide emulsified in incomplete Freund's adjuvant (WA), by subcutaneous and intraperitoneal injection (doses depicted in FIG. 7B). At 24 hours, the local (mesenteric) lymphoid nodes (LN), spleen and thymus were harvested, single cell suspensions were made, red blood cells lysed from the spleens, LN and thymus were collagenase digested. All cells were washed, counted and incubated with TcH recognizing I-Ed+SFERFEIFPKE (MHC class II-HA) complexes. The number of TcH was $1\times10^4$/well. The formation of such MHC—peptide complexes was evaluated by titrating the number of APC with constant number of Tell and measuring TcH activation after overnight incubation. The next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 µl/well, centrifuging the plate for 3 min/4° C./1500 RPM. PBS was flicked off the plate and cells were incubated overnight at 37° C. with 200 µl/well of the X-gal substrate freshly prepared as follows: 200 µl of the X-gal stock solution, (40 mg/mg in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope.

The data are expressed as TcH activation versus APC number (FIG. 7A) and as estimated percentage of APC expressing MHC-peptide complexes (FIG. 7B), based on in vitro standard curve obtained as depicted in the previous Examples, 5 and 6.

Figure 7A:
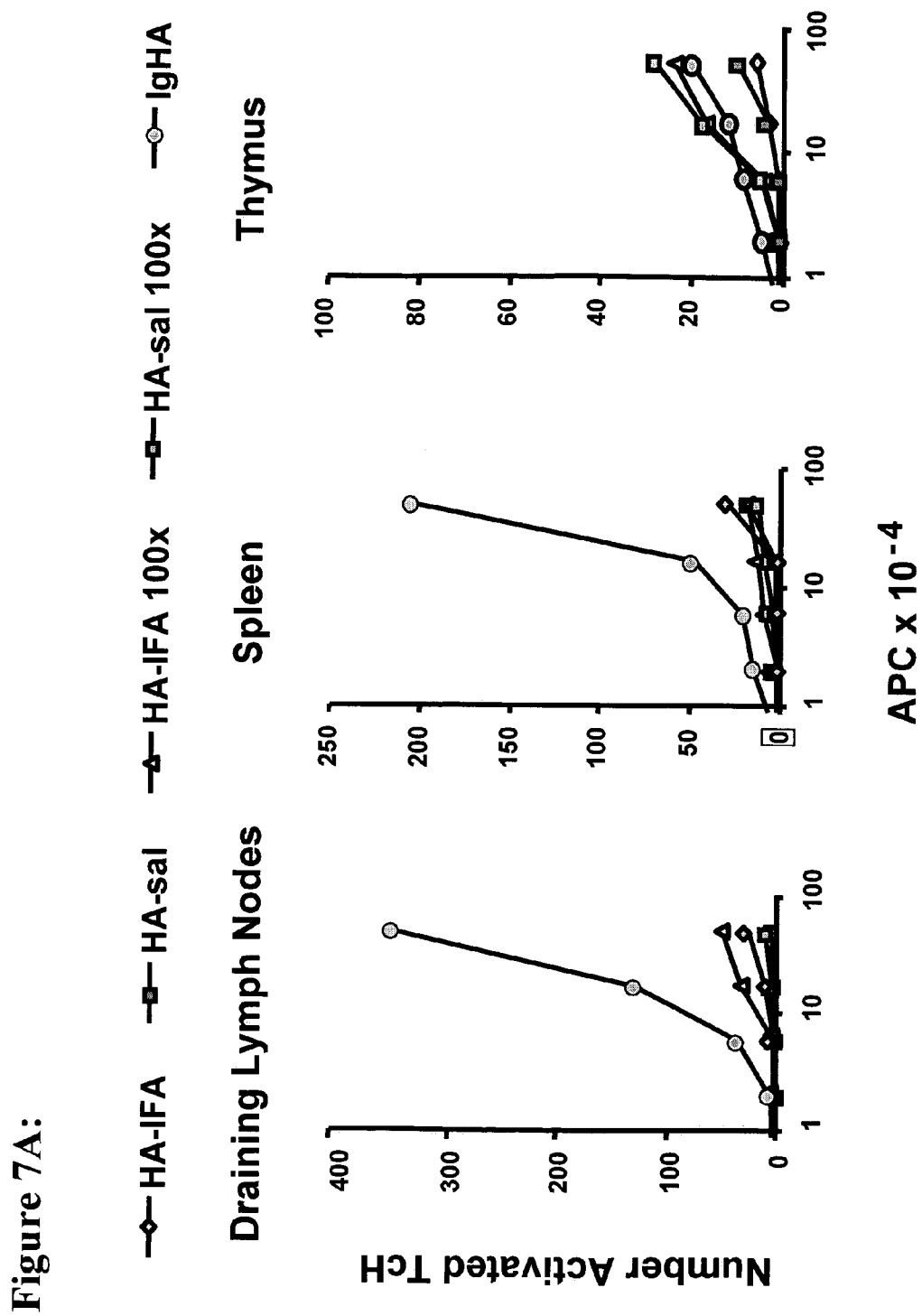

The data presented in the FIGS. 7A-7B show that the use of oil-in-water adjuvant (IFA) modestly enhanced the in vivo formation of MHC-peptide complexes on APC of lymph nodes but not spleen or thymus. Substantial dose escalation of peptide in saline or in emulsion is not paralleled by proportional enhancement in the generation of loaded APC and/or MHC—peptide complexes on APC in vivo. In contrast, use of peptide within Ig backbone enhances the formation of MHC peptide complexes considerably, on APC from secondary lymphoid organs such as lymph nodes and spleen. The formation of MHC II–peptide complexes on APC from thymus remained limited, similar to that conferred by peptide alone. The enhancement factor conferred by incorporation of peptide within the IgG was unexpectedly high (approximately 2-3 orders of magnitude), indicating that other factors, in addition to cellular handling (e.g. the above described pharmacokinetics and protective effects), were involved. Even 100 fold dose escalation of peptide alone, in saline or IFA, could not restore the in vivo loading of APC noted with peptide within IgG backbone.

EXAMPLE 7

Shows that among the three major APC subsets (DC, monocytes/macrophages and B cells) that express FcγR, the CD11c+ (DC) and CD11b+ (mostly monocytes) rather than B cells are the most potent on a per cell basis in presenting the peptide epitope subsequent to in vivo delivery via IgG backbone. The efficiency of APC loading and resulting presentation is substantially higher than that resulting from delivery of free peptide.

In vivo formation of MHC—peptide complexes on APC has been assessed subsequent to the administration of peptide epitope within IgG backbone followed by separation of various subsets of APC.

(A) Separation by using magnetic beads coupled with anti-MHC II or anti-CD11c mAb is carried out using magnetic cell separators and reagents from Miltenyi Biotec, Germany as follows: spleens were processed to single cell suspension, red blood cells lysed, then cells washed, counted and resuspended in MACS buffer (PBS supplemented with 2 mM EDTA and 0.5% BSA). Magnetically labeled cells were passed through a separation column which is placed in the magnetic field of a MACS separator. The magnetically labeled positive fraction is retained in the column while the negative fraction runs through. After removal of the column from the magnetic field, the magnetically retained positive cells are eluted from the column, cells are washed, counted, resuspended in HL1 complete media and incubated in ELISPOT plates. Usually, from the total number of approximately 90 million splenocytes separated/1 BALB/c mouse approximately 20 millions bind to magnetic beads coupled to anti-MHC II antibody and 3 millions interact with anti-CD11c mAb. Thus, less than 20 percent of splenocytes are able to present MHC class II restricted epitopes and approximately 2-3 percent are dendritic cells (see FIG. 8A). These figures were confirmed by FACS analysis using specific antibodies.

(B) The in vivo loading of APC and formation of MHC II–peptide complexes on MHC II+ splenocytes has been assessed comparatively in Balb/c mice injected intravenously with 0.72 uM of recHA (I-Ed)-IgG ("IgHA") or 18 uM of HA peptide. At 24 hours, MHC class II+ APC were isolated from spleen by MACS as above, and incubated with peptide specific TcH ($1 \times 10^4$/well), in dose response manner. The next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 μl/well, centrifuging the plate for 3 min/4° C./1500 RPM. PBS was flicked off the plate and cells were incubated overnight at 37° C. with 200 μl of the X-gal substrate freshly prepared as follows: 200 μl of the X-gal stock solution, (40 mg/ml in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope.

The results are expressed in FIG. 8B as number of activated TcH/well. As a control, MHC II+ APC from naive BALB/c mice were incubated in vitro, overnight, with an optimal concentration of HA peptide (50 ug/ml), extensively washed and incubated in different numbers with TcH as above. The results show that the formation of MHC II– peptide complexes on splenic APC is at least 2 orders of magnitude more effective when the epitope is delivered within IgG backbone.

(C) A comparative assessment of the in vivo loading of various APC subsets after administration of recHA (I-Ed)-IgG has been carried out by magnetic separation of CD11c+, CD11b+ and CD19+ APC using the same protocol as above, using CD11c, CD11b and CD19 microbeads from Miltenyi Biotec. At 24 hours after intravenous injection with 0.72 uM of recombinant immunoglobulin, the APC were isolated and incubated in a dose effect manner with a constant number of peptide specific TcH After additional 24 hours, the assay was developed as above and results expressed as number of activated TcH/well. The results in FIG. 8C show that on a per cell basis, use of peptide within IgG backbone led to predominant formation of immunogenic MHC II– peptide complexes on CD11c+ APC (dendritic cells), followed by CD11b+ monocytes and very ineffectively on CD 19+ B cells.

(D) A comparison between the efficiency of in vivo formation of MHC II– peptide complexes on CD11c+ APC subsequent to peptide versus recombinant Ig delivery has been carried out following treatment of mice as described in the section B above. The CD11c+ splenic DC were isolated by MACS using CD 11c microbeads and incubated in different numbers with $1 \times 10^4$TcH/well. Activated TcH were quantified as above and the results expressed as number of X-gal+T cells/well. As a control, CD11c+ APC from naive mice loaded ex vivo with peptide were used as described in section B. The results in FIG. 8D show that formation of MHC II peptide complexes was at least three orders of magnitude more effective when the peptide epitope was delivered within IgG backbone.

In conclusion, delivery of a peptide epitope within an IgG backbone resulted in more effective formation of MHC II–peptide complexes on CD11c+ DC. In addition, the efficiency of APC loading and formation of MHC II– peptide complexes was substantially higher when the peptide was delivered within IgG backbone. The results in FIGS. 8A-8D show that use of FcgR mediated delivery of peptides results in preferential formation of immunogenic MHC II– peptide complexes on CD11c+ and CD11b+ APC.

EXAMPLE 8

Shows a prolonged persistence in vivo of MHC-peptide complexes on APC (DC and monocytes) following administration via an IgG backbone.

The persistence of MHC II– peptide complexes on specific APC subsets was measured by magnetic separation of CD11c+ DC and CD11b+ monocytes at various intervals subsequent to intravenous injection of 2 uM of recHA (I-Ed)-IgG. In brief, magnetic separation was carried out using magnetic cell separators and reagents from Miltenyi Biotec, Germany as follows: spleens were processed to single cell suspension, red blood cells lysed, then cells washed, counted and resuspended in MACS buffer (PBS supplemented with 2 mM EDTA and 0.5% BSA). Magnetically labeled cells were passed through a separation column which is placed in the magnetic field of a MACS separator. The magnetically labeled positive fraction is retained in the column while the negative fraction runs through. After removal of the column from the magnetic field, the magnetically retained positive cells are eluted from the column, cells are washed, counted, resuspended in HL1 complete media and incubated. Different numbers of separated APC (A—CD11b+ monocytes, B—CD11c+ dendritic cells, C—whole splenocyte population) were incubated overnight with 1×104 TcH specific for the HA peptide.

As a control, APC from naive mice were used that were in vitro loaded with optimal amounts of HA peptide (50 μg/ml), overnight and washed prior to incubation ("ctrl"). The next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 μl/well, centrifuging the plate for 3 min/4° C./1500 RPM. PBS was flicked off the plate and cells were incubated overnight at 37° C. with 200 μl/well of the X-gal substrate freshly prepared as follows: 200 μl of the X-gal stock solution, (40 mg/ml in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope and the number of activated TcH/well was plotted against the number of APC harvested at various intervals after treatment.

The results show long lasting expression of peptide onto endogenous MHC II, on both DC and monocytes. The complexes persisted between 1 and 2 weeks on these two APC subsets, in the conditions employed in this assay (strategy of APC separation and detection of MHC II– peptides).

Figures 9A, 9B, 9C:
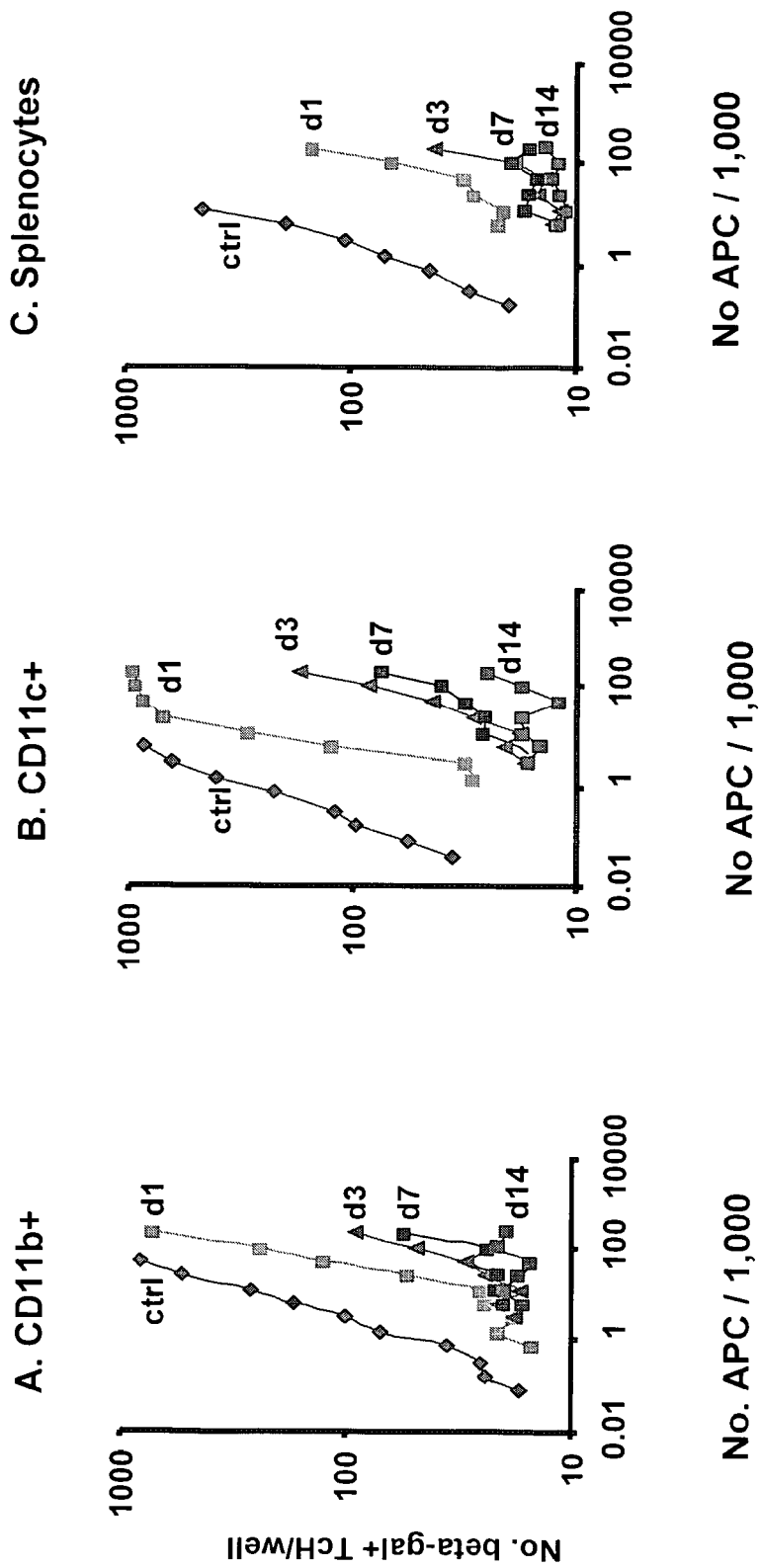
FIGS. 9A-9C show long lasting expression of peptide onto endogenous MHC II, on both DC (dendritic cells) and monocytes.

Thus, the results in FIGS. 9A-9C show that the MHC-peptide complexes on selected APC formed subsequent to in vivo delivery of epitope via Ig are long-lived.

EXAMPLE 9

Shows that the γ chain of the Fc receptors (I and III) is essential for effective in vivo loading and presentation of a T cell epitope delivered within IgG backbone, by DC and monocytes.

The dependency of APC loading on the interaction with FcγR was studied by administration of 2 uM of recHA(I-Ed)-IgG to BALB/c, mice that lack a functional FcR gamma gene. One day after intravenous treatment, the CD 11 c+ and CD 11b+ APC from spleen were separated by MACS. Separation by using magnetic beads coupled with anti-CD11c and anti-CD11b antibodies was carried out using magnetic cell separators and reagents from Miltenyi Biotec, Germany, as follows: spleens were processed to single cell suspension, red blood cells lysed, then cells washed, counted and resuspended in MACS buffer (PBS supplemented with 2 mM EDTA and 0.5% BSA). Magnetically labeled cells were passed through a separation column which is placed in the magnetic field of a MACS separator. The magnetically labeled positive fraction is retained in the column while the negative fraction runs through. After removal of the column from the magnetic field, the magnetically retained positive cells are eluted from the column, cells are washed, counted, resuspended in HL1 complete media and they were incubated in different numbers with 1×10⁴TcH specific for the HA peptide, overnight. As a control, APC from FcR gamma competent BALB/c mice were used. The next day the plate was centrifuged for 15 min/4° C./1500 RPM, then the supernatant was flicked, the cells were fixed with cold freshly made fixing solution (2% Formaldehyde, 0.2% Glutaraldehyde in 1× PBS) and the plate was again centrifuged for 3 min/4° C./1500 RPM. Fixing solution was flicked off the plate, cells washed once with PBS 200 μl/well, centrifuging the plate for 3 min/4° C./1500 RPM. PBS was flicked off the plate and cells Were incubated overnight at 37° C. with 200 μl/well of the X-gal substrate freshly prepared as follows: 200 μl of the X-gal stock solution, (40 mg/mg in DMSO) in 10 ml of substrate buffer (5 mM Potassium Ferrocyanide, 5 mM Potassium Ferricyanide, 2 mM MgCl 2 in 1× PBS). The blue activated TcH were scored visually using the microscope. The results are expressed as number of activated TcH/well for different APC subsets: CD11c+ DC (A) and CD11b+ monocytes (B), or as control, whole splenic population (C).

Figure 10:
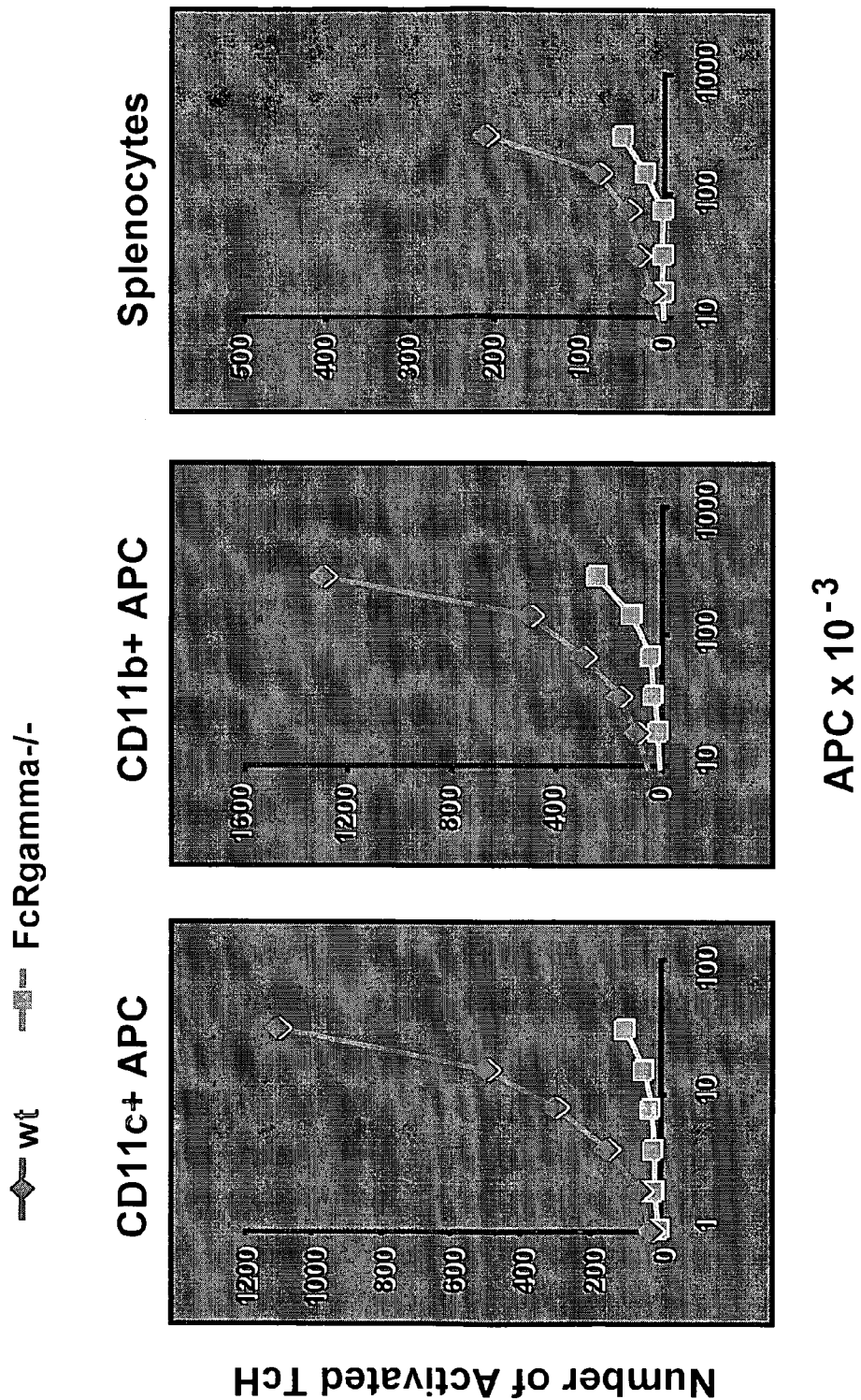
FIG. 10 shows that formation of MHC II–peptide complexes on dendritic cells and monocytes, subsequent to IgG mediated delivery of peptide epitope, is critically dependent on ITAM+ FcγR that encompass the gamma chain.

The results (FIG. 10) clearly show that the formation of MHC II– peptide complexes on DC and monocytes, subsequent to IgG mediated delivery of peptide epitope, is critically dependent on ITAM+ FcgR that encompass the gamma chain. In addition, gamma chain negative FcR isoforms cannot compensate for the absence of gamma chain+ FcR isoforms, in that regard.

EXAMPLE 10

Shows that the efficiency of T cell activation by a peptide delivered within the IgG backbone is dependent on the expression of γ chain+ FcγR (that promote activity) and FcγRIIB (that limit the activity) on APC. In addition, this experiment shows that ITIM-bearing FcγRIIB keeps in check the immune response to a peptide delivered within IgG backbone.

The differential role of FcR gamma+ versus gamma– isoforms to the immune response triggered by peptide epitope within IgG backbone, was studied by ex vivo loading of APC followed by adoptive transfer. Splenocytes from wild type, FcR gamma– or FcRIIB– BALB/c mice were incubated for 3 hours at 370° C. as follows: 10 million cells/1 ml of serum free HL-1 medium were admixed with 50 ug/ml of HA 110-120 peptide or 10 ug/ml of recHA(I-Ed)-IgG. Subsequently, the cells were washed and adoptively transferred into naive BALB/c mice (1 million cells suspended in 200u1 serum free HL-1 and divided into 2 equal inoculi administered subcutaneously and intraperitoneally). After 2 weeks, the recipient mice were sacrificed, spleens harvested and the T cell response to the HA 110-120 peptide measured by ELISPOT analysis as follows: the ELISPOT plates (Millipore, Molsheim, France) were incubated with purified anti-cytokine Abs (4 ug/mg for anti-IL2 and anti-IL4, and 8 μg/mg for anti-IFN gamma, from BD Pharmingen) in sterile PBS (50 μl/well) at 4° C. overnight. The next day, the plates were washed 2 times with DMEM media and blocked with 200 μl/well of DMEM complete containing FBS, for an hour at 37° C. Single cell suspension was made from the spleens, red blood cells were lysed, cells washed, counted and incubated at 5×10⁵/well together with 50 μg/ml HA 110-120 peptide or just with media, to assess the background.

Plates were incubated 72 hours at 37° C., 5% CO2. After 3 days, the plates were washed 5 times with PBS—tween20 0.05% (washing buffer), and incubated with 100 μl/well of biotinylated anti-cytokine Abs, 2 μg/ml in PBS—tween20 0.05%—FBS 0.1% (ELISPOT buffer) overnight at 4° C.

Figure 11:
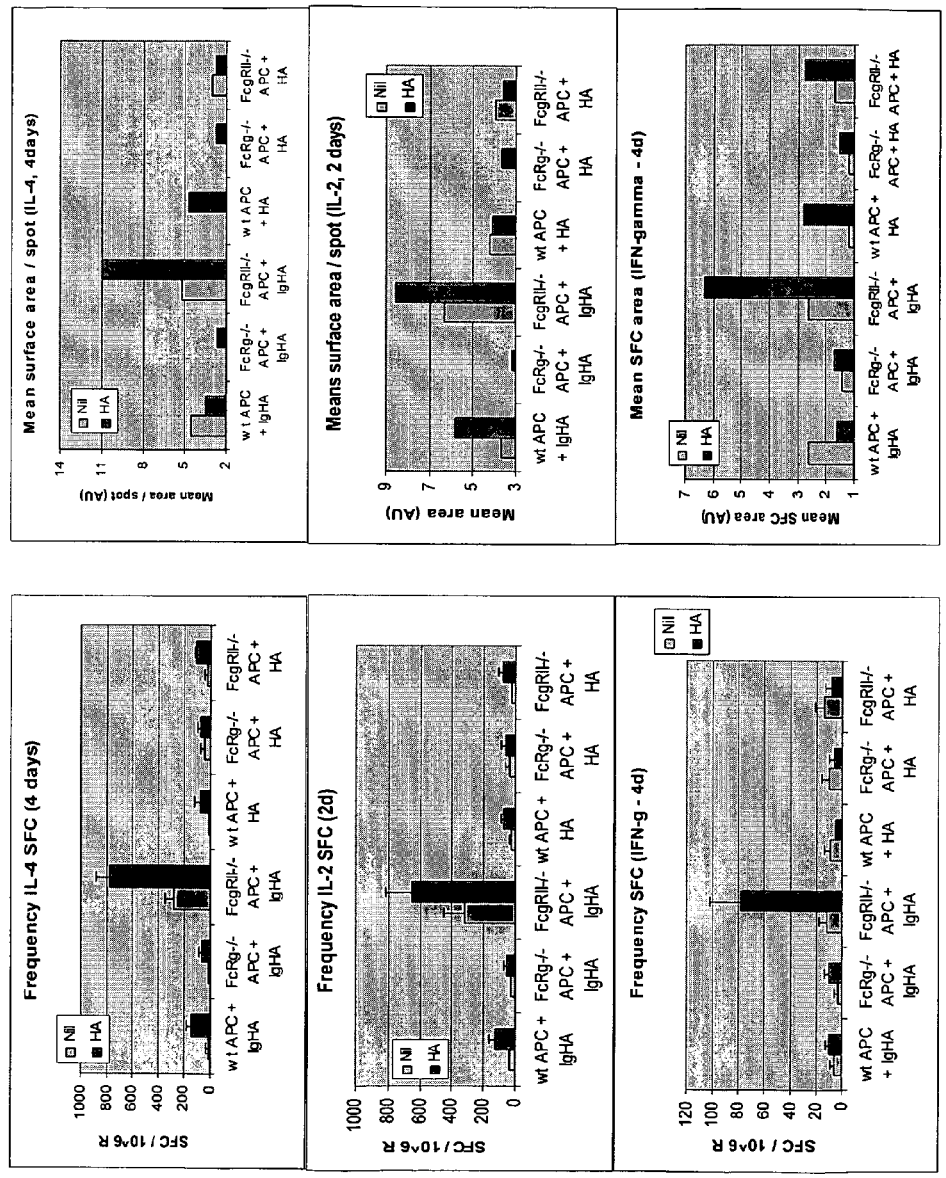
FIG. 11 shows that results show that the expression of the gamma chain of ITAM+ FcγR isoforms is necessary for the induction of T cell response to APC loaded with peptide within the IgG backbone.

The next day plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. Plates were then allowed to dry at room temperature for 24 hours. The data were acquired using an automated system (Navitar, Rochester, N.Y.) with ImagePro-Plus) software (Media Cybernetics, Silver Spring, Md.). The results are expressed in FIG. 11 as frequency of cytokine producing (A: IL-2, B: IL-4, and C: IFN-gamma) spot forming colonies obtained by incubation with medium only, or medium supplemented with HA 110-120 peptide (10 ug/ml) (mean+SEM of triplicates, corresponding to 3 mice/group).

The results (FIG. 11) show that the expression of the gamma chain of ITAM+ FcgR isoforms is necessary for the induction of T cell response to APC loaded with peptide within IgG backbone. This was not necessary for the immunogenic effect of APC pulsed with peptide. Conversely, absence of ITIM+ FcgRII results in profound increase of the T cell response to APC pulsed with recombinant IgG but not HA peptide. Together, these data show that the T cell response to recombinant IgG bearing a peptide epitope is determined by a complex interplay between ITAM+ and ITIM+ Fcgamma receptors on APC.

EXAMPLE 11

Shows that unexpectedly, various subsets of APC in vivo loaded with epitope inserted within IgG backbone, differentially induce distinct regulatory subsets: while monocytes induce Th2 and Tr1 cells more effectively, both dendritic cells and monocytes induce Th3 cells. In addition, on a cell population level, the CD11b+ monocytes are more potent than the dendritic cells in triggering a regulatory response following IgG-mediated delivery of T cell epitope.

Four BALB/c mice were injected intravenously with 2 μM of recHA (I-Ed)-IgG. One day later, the spleens were harvested and APC were isolated by MACS using anti-CD11c, anti-CD11b or anti-CD19 monoclonal antibodies coupled with magnetic beads. Separation by using magnetic beads coupled with anti-CD11b, anti-CD11c and anti-CD19 mAb is carried out using magnetic cell separators and reagents from Miltenyi Biotec, Germany as follows: spleens were processed to single cell suspension, red blood cells lysed, then cells washed, counted and resuspended in MACS buffer (PBS supplemented with 2 mM EDTA and 0.5% BSA). Magnetically labeled cells were passed through a separation column which is placed in the magnetic field of a MACS separator. The magnetically labeled positive fraction is retained in the column while the negative fraction runs through. After removal of the column from the magnetic field, the magnetically retained positive cells are eluted from the column, cells are washed, counted, resuspended in serum free HL-1 medium as follows: $3 \times 10^6$/mg CD11c+ DC, $28 \times 10^6$/ml CD11b+ or $84 \times 10^6$/ml of CD19+ B cells. This numerical distribution respects the proportion of the APC subsets isolated from the splenic tissue. Cells were transferred into naïve BALB/c mice by subcutaneous and intraperitoneal injection (100+100 μl/mouse, n=2 mice/group). At 2 weeks after the adoptive transfer, mice were sacrificed and T cell response measured by ELISPOT (IL-4 and IFN-γ) or measurement of cytokine production in cell culture supernatants, by ELISA TGF-β1 kit (R&D Systems, cat #DY240) and IL-10 kit (Biosource international, cat #KMC0104).

Figures 12A, 12B, 12C, 12D:
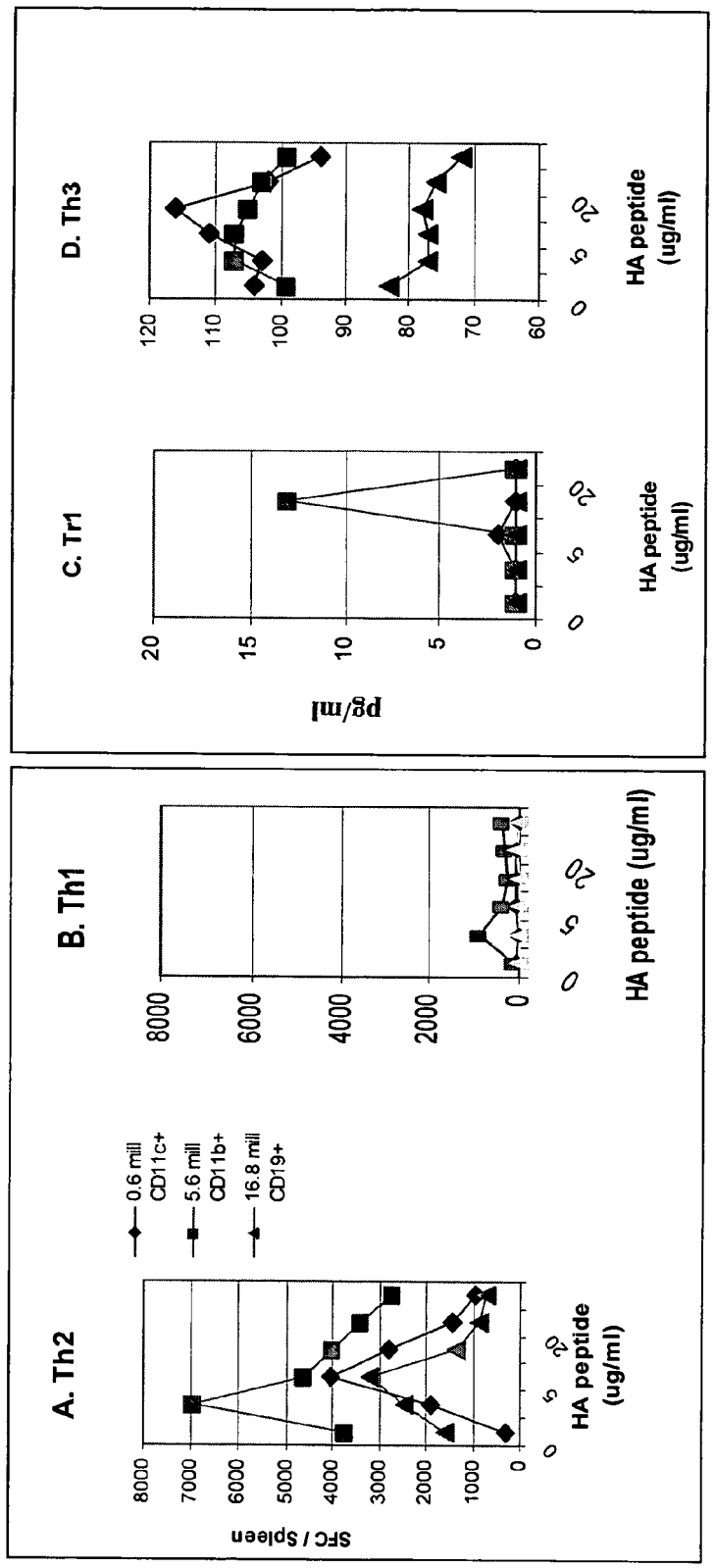
FIGS. 12A-12D show that unexpectedly and in contrast with the potency/cell basis (Example 8), at the organism level, the CD11b+ monocytes have the highest impact on the immune response to a peptide epitope delivered within the IgG backbone.

The results are expressed in FIG. 12 as number of spot forming colonies/spleen (average of duplicates; panels A, B) or amount of cytokine measured in supernatants (pg/ml, average of duplicates; panels C, D) at various concentrations of HA peptide used for restimulation.

The results (FIG. 12, panels A-D) clearly show that unexpectedly, and in contrast with the potency/cell basis (Example 8), at the organism level, the CD 11b+ monocytes have the highest impact on the immune response to a peptide epitope delivered within the IgG backbone. Thus, the CD11b+ APC subset induced both Th2, Tr1 and Th3 cells. In contrast, the CD11c+ DC induced Th3 cells and more reduced Th2 response. Finally, despite their substantial number, the CD19+ B cells were poor inducers of T cell immunity to the peptide epitope within the IgG backbone. No significant Th1 responses were induced by either of the APC subsets tested.

EXAMPLE 12

Shows that the loading of APC in vivo with a peptide delivered within IgG backbone results in induction of Th2 but not Th1 immunity.

BALB/c mice were immunized with 100 μg of recHA. (I-Ed)-IgG ("IgHA"), or a, molar equivalent amount of HA peptide epitope (2 μg), by subcutaneous injection and sacrificed 2 weeks later. The immune response was measured by ELISPOT analysis using splenocytes from treated mice as responders, and mitomycin-treated splenocytes from naïve mice as stimulators, as follows: the ELISPOT plates (Millipore, Molsheim, France) were incubated with purified anti-cytokine Abs (4 ug/ml for anti-IL2 and anti-IL4, and 8 μg/ml for anti-IFN gamma, from BD Pharmingen) in sterile PBS (50 μl/well) at 4° C. overnight. The next day, the plates were washed 2 times with DMEM media and blocked with 200 μl/well of DMEM complete containing FBS, for an hour at 37° C. Single cell suspension was made from the spleens, red blood cells were lysed, cells washed, counted and incubated at $5 \times 10^5$/well together with 20 μg/ml HA 110-120 peptide or just with media, to assess the background.

Stimulator cells were prepared from naive mice as follows: single cell suspension was prepared from spleens, red blood cells were lysed, cells were washed, resuspended in HL1 complete and mitomycin treated for 30 minutes. Afterwards, cells were washed 3 times, counted and resuspended in serum free HL1 media. The plates were incubated 72 hours at 37° C., 5% CO2. After 3 days, the plates were washed 5 times with PBS—tween20 0.05% (washing buffer), and incubated with 100 μl/well of biotinylated. anti-cytokine Abs, 2 μg/ml in PBS—tween20 0.05% —FBS 0.1%(ELISPOT buffer) overnight at 4° C.

The next day, the plates were washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours. The data were acquired using an automated system (Navitar, Rochester, N.Y.) with ImagePro-Plus) software (Media Cybernetics, Silver Spring, Md.).

Figures 13A, 13B:
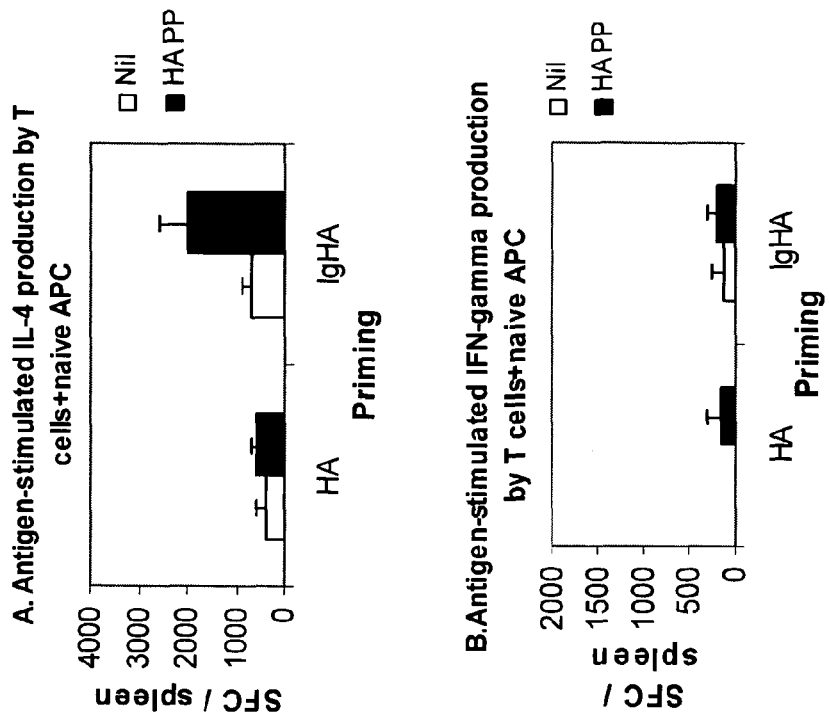
FIGS. 13A-13B shows that FcγR-mediated delivery of a T cell epitope within the recombinant Ig backbone results in Th2 rather than Th1 response.

The results are expressed in FIG. 13 as number of IL-4-producing (A) or IFN-γ producing (B) T cell colonies/spleen (mean±SEM of triplicates) when splenocytes were restimulated with 10 μg/ml of HA peptide or cell culture medium alone. Thus, this Example shows that FcgR-mediated delivery of T cell epitope within recombinant Ig backbone results in Th2 rather than Th1 response.

EXAMPLE 13

Shows that the repeated loading of APC in vivo with a peptide delivered within IgG backbone results in induction of Th3 and Tr1 immunity.

BALB/c mice were immunized with 40 ug of heat aggregated (15 ruins at 63° C.) of recHA (I-Ed)-IgG ("IgHA") administered by intranasal instillation boosted 2 weeks later by subcutaneous injection with 100 ug of recombinant immunoglobulin in saline. As controls, mice primed with heat aggregated IgG2b isotype control were used. After an additional 2 weeks, the mice were sacrificed and T cell response assessed by in vitro restimulation of splenocytes with HA peptide by ELISPOT analysis as follows: the ELISPOT plates (Millipore, Molsheim, France) were incubated with purified anti-cytokine Abs (4 ug/ml for anti-IL2 and anti-IL4, and 8 µg/ml for anti-IFN gamma, from ED Pharmingen) in sterile PBS (50 µl/well) at 4° C. overnight. The next day, the plates were washed 2 times with DMEM media and blocked with 200 µl/well of DMEM complete containing FBS, for an hour at 37° C.

Single cell suspension was made from the spleens, red blood cells were lysed, cells washed, counted and incubated at $5\times10^5$/well together with 20 µg/ml HA 110-120 peptide or just with media, to assess the background. Plates were incubated 72 hours at 37° C., 5% CO2. After 3 days, plates were washed 5 times with PBS—tween20 0.05% (washing buffer), and incubated with 100 µl/well of biotinylated anti-cytokine Abs, 2 µg/ml in PBS—tween20 0.05%—FBS 0.1% (ELISPOT buffer) overnight at 4° C.

The next day, plates were washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. Plates were then allowed to dry at room temperature for 24 hours.

The data were acquired using an automated system (Navitar, Rochester, N.Y.) with ImagePro-Plus) software (Media Cybernetics, Silver Spring, Md.). The TGF-beta and IL-10 production were measured by ELISA TGF-β1 kit (R&D Systems, cat #DY240) and IL-10 kit (Biosource international, cat #KMC0104). The results are expressed as cytokine concentration (average of triplicates) after subtraction of background.

Figure 14:
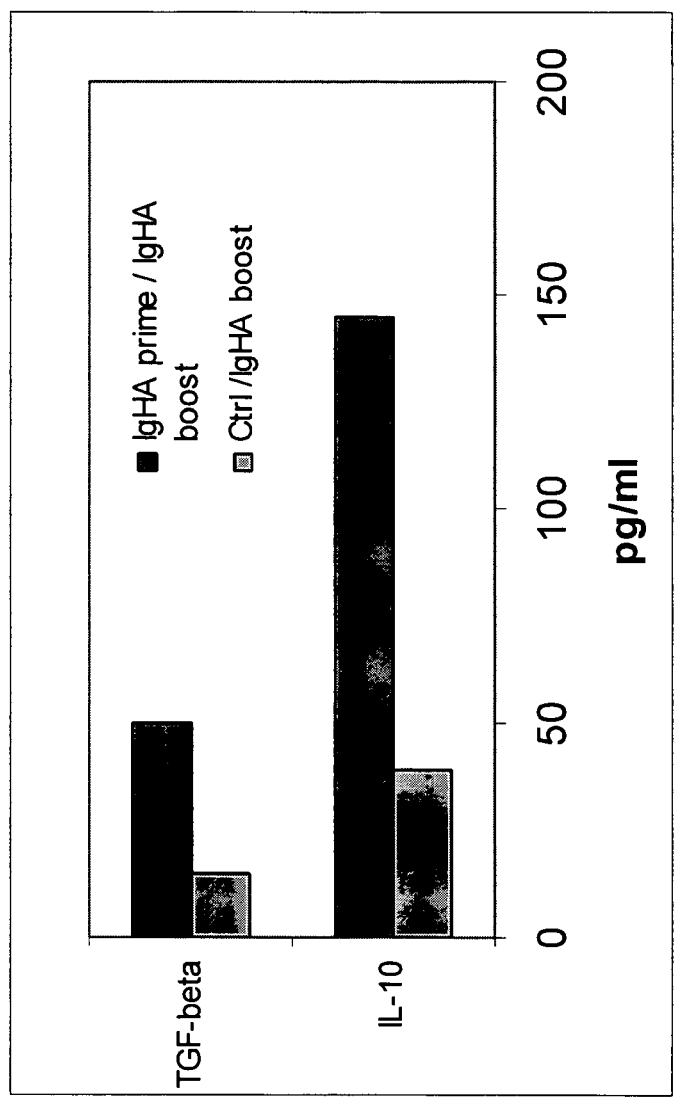
FIG. 14 shows that FcγR-mediated delivery of T cell epitope within recombinant Ig backbone results in Th2 rather than Th1 response.

The data, as shown in FIG. 14, show that mucosal priming with epitope bearing recombinant immunoglobulin resulted in differentiation of Th3 and Tr1 cells that were expanded subsequently by systemic boosting.

EXAMPLE 14

Shows that only a virus, but not the conventional adjuvant CFA, was able to trigger significant Th1 response to a peptide epitope inserted within the IgG backbone.

BALB/c mice were immunized intraperitoneally with 100 ug of recHA (I-Ed)-IgG in saline, emulsified in Complete Freund's Adjuvant ("CFA") or with 105 TCID50 of influenza virus strain WSN, that bears the HA epitope. At 2 weeks after immunization, the mice (n=3/group) were sacrificed and the T cell response to HA peptide measured by ELISPOT analysis as follows: the ELISPOT plates (Millipore, Molsheim, France) were incubated with purified anti-cytokine Abs (4 ug/ml for anti-IL2 and anti-IL4, and 8 µg/ml for anti-IFN gamma, from BD Pharmingen) in sterile PBS (50 µl/well) at 4° C. overnight. The next day, the plates were washed 2 times with DMEM media,and blocked with 200 µl/well of DMEM complete containing FBS, for an hour at 37° C.

Single cell suspension was made from the spleens, red blood cells were lysed, cells washed, counted and incubated at $5\times10^5$/well together with 20 µg/ml HA 110-120 peptide or just with media, to assess the background.

Plates were incubated 72 hours at 37° C., 5% CO2. After 3 days, the plates were washed 5 times with PBS—tween20 0.05% (washing buffer), and incubated with 100 µl/well of biotinylated anti-cytokine Abs, 2 µg/ml in PBS—tween20 0.05%—FBS 0.1% (ELISPOT buffer) overnight at 4° C. The next day; plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus) software (Media Cybernetics, Silver Spring, Md.). The results are represented as mean±SEM of frequency of cytokine producing colonies in the spleen.

Figure 15:
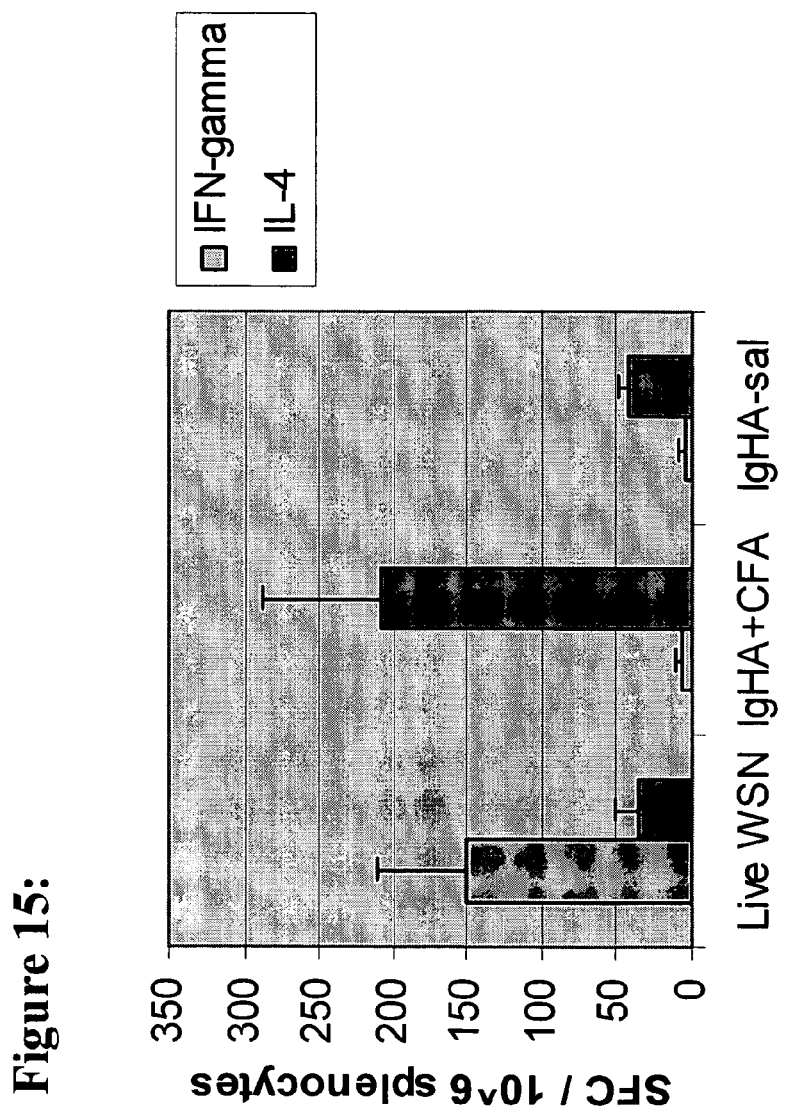
FIG. 15 shows that a peptide epitope within the IgG backbone triggers a cellular response of Th2 profile that is enhanced but not switched by a conventional adjuvant (CFA)

The results in FIG. 15 show that a peptide epitope within the IgG backbone triggers a cellular response of Th2 profile that is enhanced but not switched by a conventional adjuvant (CFA). In contrast, the profile afforded by live virus immunization was Th1 biased.

EXAMPLE 15

Shows that the presentation of peptide epitope subsequent to IgG mediated delivery results in a T cell response that could be further manipulated by increasing co-stimulation with anti-CD40mAb, recombinant IL-12 or synthetic dsRNA.

Dendritic cells from naive BALB/c mice were harvested by MACS from splenic cell suspensions as follows: Separation by using magnetic beads coupled with anti-CD11c was carried out using magnetic cell separators and reagents from Miltenyi Biotec, Germany as follows: spleens were processed to single cell suspension, red blood cells lysed, the cells washed, counted and resuspended in MACS buffer (PBS supplemented with 2 mM EDTA and 0.5% BSA). Magnetically labeled cells were passed through a separation column which is placed in the magnetic field of a MACS separator. The magnetically labeled positive fraction is retained in the column while the negative fraction runs through. After removal of the column from the magnetic field, the magnetically retained positive cells are eluted from the column, cells are washed, counted, resuspended in HL1 complete media and were pulsed ex vivo in serum free HL-1 medium for 2 hours, at a concentration of 3 million/ml, with 50 ug/ml of recHA(I-Ed)-IgG alone or supplemented with 5 ng/ml of recIL-12, 50 ug/ml of double stranded RNAs (pA:pU or pI:pC). Alternatively, the cells were incubated with recombinant Ig and wells precoated with 10 ug/ml of anti-CD40 mAb. The cells were harvested, washed and adoptively transferred to naive BALB/c mice (300,000 delivered half subcutaneously and half intraperitoneally) in serum free HL-1 medium.

At 2 weeks, the mice were sacrificed and T cell responses measured against HA by ELISPOT analysis as follows: the ELISPOT plates (Millipore, Molsheim, France) were incubated with purified anti-cytokine Abs (4 ug/mg for anti-IL2 and anti-IL4, and 8 µg/ml for anti-IFN gamma, from BD Pharmingen) in sterile PBS (50 µl/well) at 4° C. overnight. The next day, the plates were washed 2 times with DMEM media and blocked with 200 µl/well of DMEM complete containing FBS, for an hour at 37° C.

Single cell suspension was made from the spleens, red blood cells were lysed, cells washed, counted and incubated at $5\times10^5$/well together with 50 µg/ml HA 110-120 peptide or just with media, to assess the background. Plates were incubated 72 hours at 37° C., 5% CO2. After 3 days, plates were washed 5 times with PBS—tween20 0.05% (washing buffer) and incubated with 100 μl/well of biotinylated anti-cytokine Abs, 2 μg/ml in PBS—tween20 0.05%—FBS 0.1% (ELISPOT buffer) overnight at 4° C. The next day plates were washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus) software (Media Cybernetics, Silver Spring, Md.). The results are shown as mean+SEM (n=3) of the frequency of spot forming colonies associated with IL-2 or IL-4 production, after subtraction of the background, for each ex vivo stimulatory combination.

Figure 16:
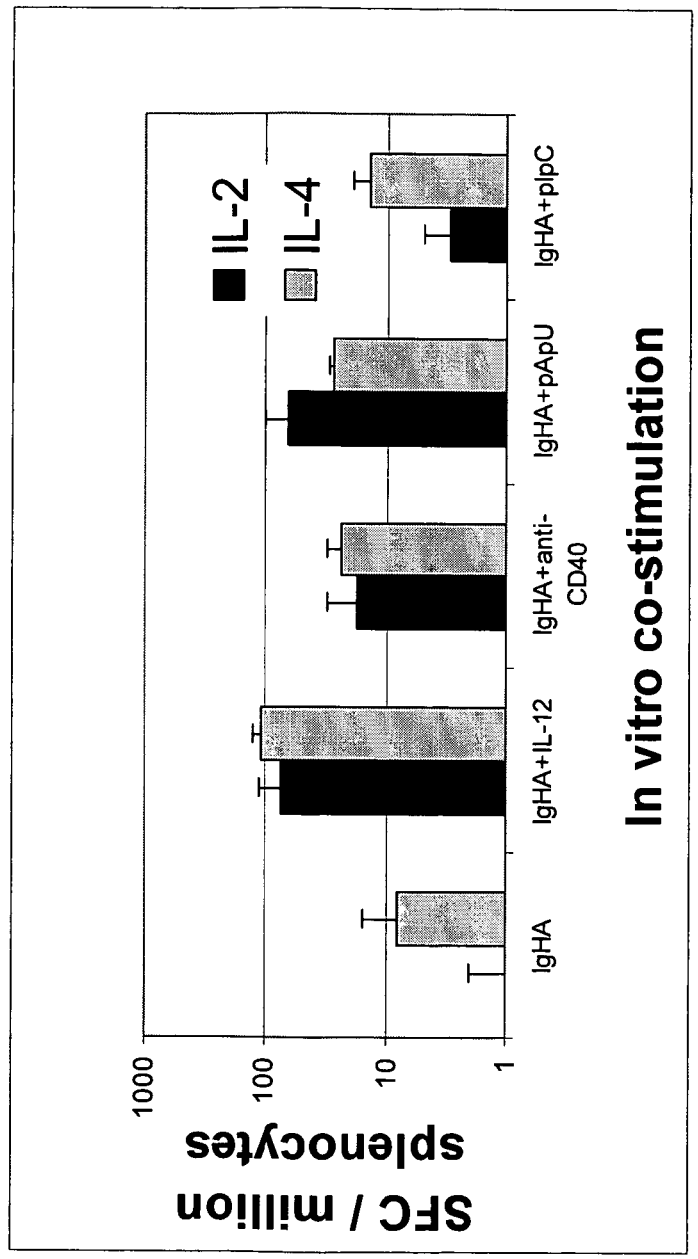
FIG. 16 shows that peptide presentation by APC, subsequent to loading with antigen by using recombinant IgG as delivery platform, occurs in context of limited co-stimulation.

The results in FIG. 16 show that peptide presentation by APC, subsequent to loading with antigen by using recombinant IgG as delivery platform, occurs in context of limited co-stimulation. IL-12, anti-CD40 or synthetic dsRNA can all enable APC loaded with antigen via FcgR, to prime IL-2 and enhanced IL-4 producing T cell immunity against the cognate (HA) peptide.

EXAMPLE 16

The activity of the long-lived IL-4 producing Th2 cells triggered by in vivo loading of APC with IgG-peptide is dependent on the continuous interaction with endogenous APC and requires competent CD4.

BALB/c mice were immunized with 100 ug of recHA (I-Ed)-IgG or HA peptide subcutaneously, sacrificed at 2 weeks and the T cell response measured by ELISPOT analysis as follows: the ELISPOT plates (Millipore, Molsheim, France) were incubated with purified anti-cytokine Abs (4 ug/ml anti-IL4, from BD Pharmingen) in sterile PBS (50 μl/well) at 4° C. overnight. The next day, the plate was washed 2 times with DMEM media and blocked with 200 μl/well of DMEM complete containing FBS, for an hour at 37° C.

Single cell suspension was made from the spleens, red blood cells were lysed, cells washed, counted and incubated at $5 \times 10^5$/well together with 20 μg/ml HA 110-120 peptide or just with media, to assess the background. The plate was incubated 72 hours at 37° C., 5% CO2. After 3 days, the plate was washed 5 times with PBS—tween20 0.05% (washing buffer) and incubated with 100 μl/well of biotinylated anti-cytokine Abs, 2 μg/ml in PBS-tween20 0.05%-FBS 0.1% (ELISPOT buffer) overnight at 4° C.

The next day, the plate was washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plate was then allowed to dry at room temperature for 24 hours. The data were acquired using an automated system (Navitar, Rochester, N.Y.) with ImagePro-Plus) software (Media Cybernetics, Silver Spring, Md.).

(A) During the HA stimulation phase, blocking anti-CD4 or anti-CD8 mAb was added at 10 ug/mg in selected wells. The results are expressed in FIG. 17A as mean+SEM of number of HA-stimulated IL-4 producing colonies per spleen, after subtraction of background (n=3 mice/group).
(B) Splenocytes from mice immunized with recombinant Ig as above, were incubated in elispot plate as is or after magnetic depletion of endogenous MHC II+ APC with MHC II+ from naive BALB/c mice, with medium alone or in the presence of 10 ug/ml of HA peptide. Separation by using magnetic beads coupled with anti-MHC II was carried out using magnetic cell separators and reagents from Miltenyi Biotec, Germany as follows: spleens were processed to single cell suspension, red blood cells lysed, then cells washed, counted and resuspended in MACS buffer (PBS supplemented with 2 mM EDTA and 0.5% BSA). Magnetically labeled cells were passed through a separation column which is placed in the magnetic field of a MACS separator. The magnetically labeled positive fraction is retained in the column while the negative fraction runs through. After removal of the column from the magnetic field, the magnetically retained positive cells are eluted from the column, cells are washed, counted, resuspended in HL I complete media and were incubated in the ELISPOT assay, protocol to follow. The ELISPOT plates (Millipore, Molsheim, France) were incubated with purified anti-cytokine Abs (4 ug/ml for anti-IL2 and anti-IL4, and 8 μg/ml for anti-IFN gamma, from BD Pharmingen) in sterile PBS (50 μl/well) at 4° C. overnight. The next day, the plates were washed 2 times with DMEM media and blocked with 200 μl/well of DMEM complete containing FBS, for an hour at 37° C. Single cell suspension was made from the spleens, red blood cells were lysed, cells washed, counted and incubated at $5 \times 10^5$/well together with 50 μg/ml HA 110-120 peptide or just with media, to assess the background.

Plates were incubated 72 hours at 37° C., 5% CO2. After 3 days, the plates were washed 5 times with PBS—tween 20 0.05% (washing buffer) and incubated with 100 μl/well well of biotinylated anti-cytokine Abs, 2 μg/ml in PBS—tween 20 0.05%—FBS 0.1% (ELISPOT buffer) overnight at 4° C.

The next day, plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. Plates were then allowed to dry at room temperature for 24 hours.

Figure 17A:
FIGS. 17A-17B show that the activity of HA (110-120 hemagglutinin peptide) specific IL-4 producing T cells triggered by administration of recHA(I-Ed)-IgG is dependent on CD4 rather than CD8.
Figure 17B:
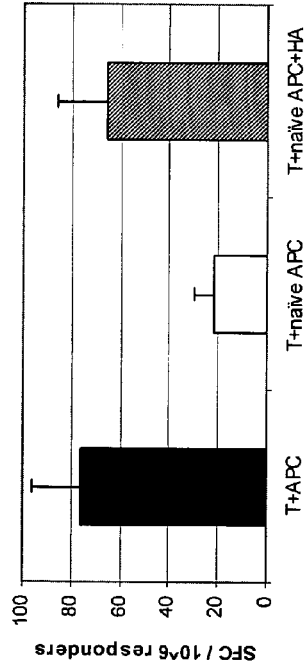

The data were acquired using an automated system (Navitar, Rochester, N.Y.) with ImagePro-Plus) software (Media Cybernetics, Silver Spring, Md.) and the results expressed as mean±SEM of the frequency of IL-4 producing T cells. The results in FIGS. 17A-17B show that the activity of HA specific IL-4 producing T cells triggered by administration of recHA(I-Ed)-IgG is dependent on CD4 rather CD8. In addition, the long lived IL-4 production by primed T cells depends on stable interaction with endogenous APC.

EXAMPLE 17

Shows that FcγR-mediated delivery of a T cell epitope is more effective than the peptide in differentially affecting the phenotype of activated, specific T cells: dose-dependent down regulation of IL-2, IFN-γ, and IL-4, with up-regulation of IL-10 and TGF-β.

Activated SFERFEIFPKE-specific T cells were separated from BALB/c mice immunized 2 weeks previously with 100 μg peptide in CFA. They were incubated with mitomycin treated splenocytes in the presence of various amounts of recHA(I-Ed)-IgG or corresponding peptide. The expansion and cytokine production (IFN-γ, IL-4, IL-2) was estimated by ELISPOT analysis as follows: the ELISPOT plates (Millipore, Molsheim, France) were incubated with purified anti-cytokine Abs (4 ug/ml for anti-IL2 and anti-IL4, and 8 μg/ml for anti-IFN gamma, from BD Pharmingen) in sterile PBS (50 μl/well) at 4° C. overnight. The next day, the plates were washed 2 times with DMEM media and blocked with 200

μl/well of DMEM complete containing FBS, for an hour, at 37° C. Single cell suspension was made from the spleens, red blood cells were lysed, cells washed, counted and incubated at $5\times10^5$/well together with 20 μs/ml HA 110-120 peptide or just with media, to assess the background.

The plates were incubated 72 hours at 37° C., 5% CO2. After 3 days, the plates were washed 5 times with PBS—tween 20 0.05% (washing buffer) and incubated with 100 μl/well of biotinylated anti-cytokine Abs, 2 μg/ml in PBS—tween 20 0.05%—FBS 0.1% (ELISPOT buffer) overnight at 4° C. The next day, the plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus) software (Media Cybernetics, Silver Spring, Md.). In addition, TGF-β and IL-10 production were measured by ELISA at 48 hours after incubation using TGF-β1 kit (R&D Systems, cat #DY240) and IL-10 kit (Biosource international, cat #KMC0104).The results are expressed as frequency of spot forming cells (SFC) or concentration of cytokine versus amount of antigen added in vitro.

Figure 18:
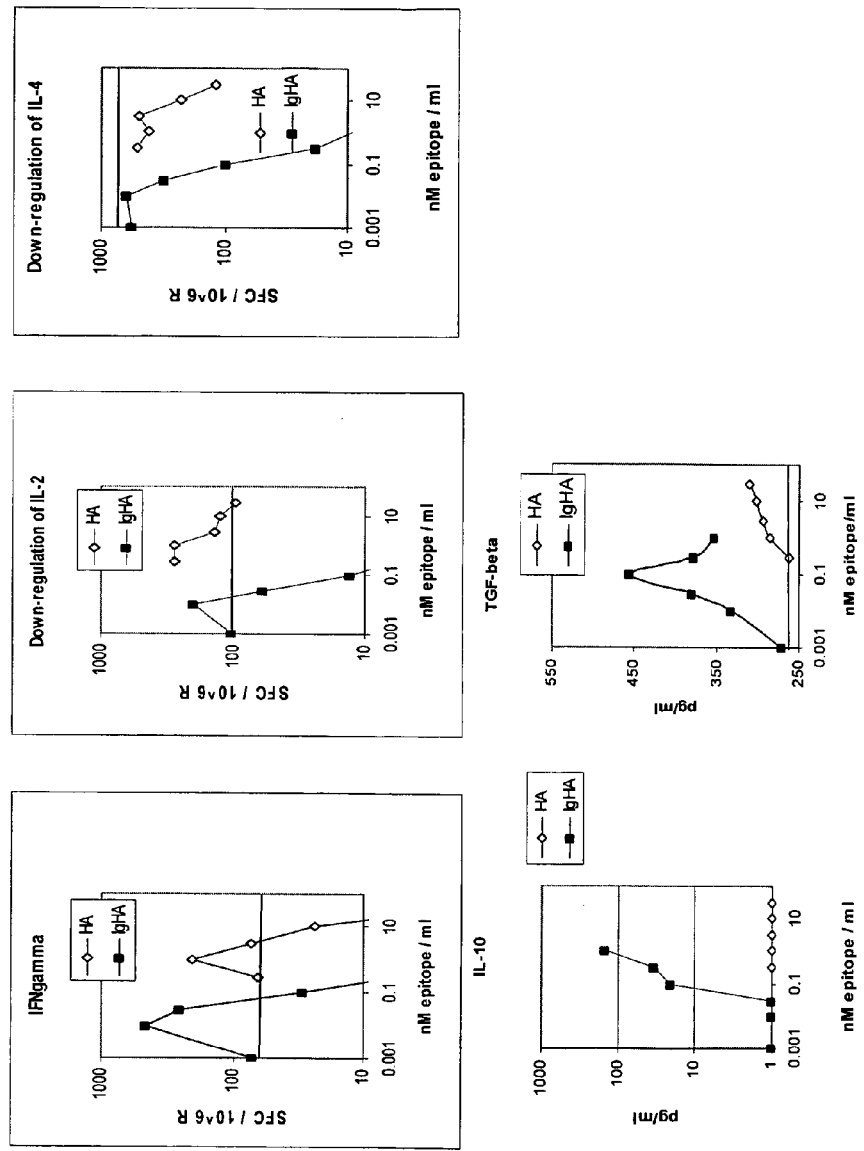
FIG. 18 shows that the IgG mediated delivery of T cell epitope has a profound and differential effect on the expansion and cytokine production by activated T cells: IL-2, IFN-γ and surprisingly IL-4, were down-regulated in a dose-related manner.

The results in FIG. 18 show that the IgG mediated delivery of a T cell epitope has a profound and differential effect on the expansion and cytokine production by activated T cells: IL-2, IFN-γ and surprisingly EL-4, were down-regulated in a dose-related manner. The Ig-peptide was substantially more effective in modulating the cytokine production, as compared to the peptide itself. In contrast, only the Ig-peptide turned on effectively the production of IL-10 and TGF-beta in a dose-dependent manner. Thus, the T cell epitope in context of Ig backbone, but not separately, differentially modulated the function of activated cells.

EXAMPLE 18

Shows that surprisingly, a peptide delivered within the IgG backbone, that is not an immune complex nor is a receptor cross-linking antibody, results in induction of a class I restricted immune response. This response had a different profile from that triggered by live virus (Tc2 type consisting in IL-4 but not IFN-γ production).

BALB/c mice were injected with 50 μg of recNP(Kd)-IgG encompassing the MHC class I-restricted peptide TYTQ-TRALV (Seq. I.D. No. 6) by subcutaneous injection. The mice were sacrificed 2 weeks later and peptide-specific cytokine production was measured by ELISPOT analysis as follows: the ELISPOT plates (Millipore, Molsheim, France) were incubated with purified anti-cytokine Abs (4 ug/ml for anti-IL2 and anti-IL4, and 8 μg/ml for anti-IFN gamma, from BD Pharmingen) in sterile PBS (50 μl/well) at 4° C. overnight. The next day, the plates were washed 2 times with DMEM media and blocked with 200 μl/well of DMEM complete containing PBS, for an hour at 37° C.

Single cell suspension was made from the spleens, red blood cells were lysed, cells washed, counted and incubated at $5\times10^5$/well together with various concentrations of NP peptide. Plates were incubated 72 hours at 37° C., 5% CO2. After 3 days, the plates were washed 5 times with PBS—tween 20 0.05% (washing buffer) and incubated with 100 μl/well of biotinylated anti-cytokine Abs, 2 μg/ml in PBS—tween 20 0.05%—FBS 0.1% (ELISPOT buffer) overnight at 4° C. The next day the plates were washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus) software (Media Cybernetics, Silver Spring, Md.). The results are expressed in FIG. 19A as total number of spot forming colonies (SFC)/spleen (mean of n=3). As controls, naïve mice or mice injected intraperitoneally with $10^5$ $TCID_{50}$ of live WSN influenza virus were used.

Figure 19B:
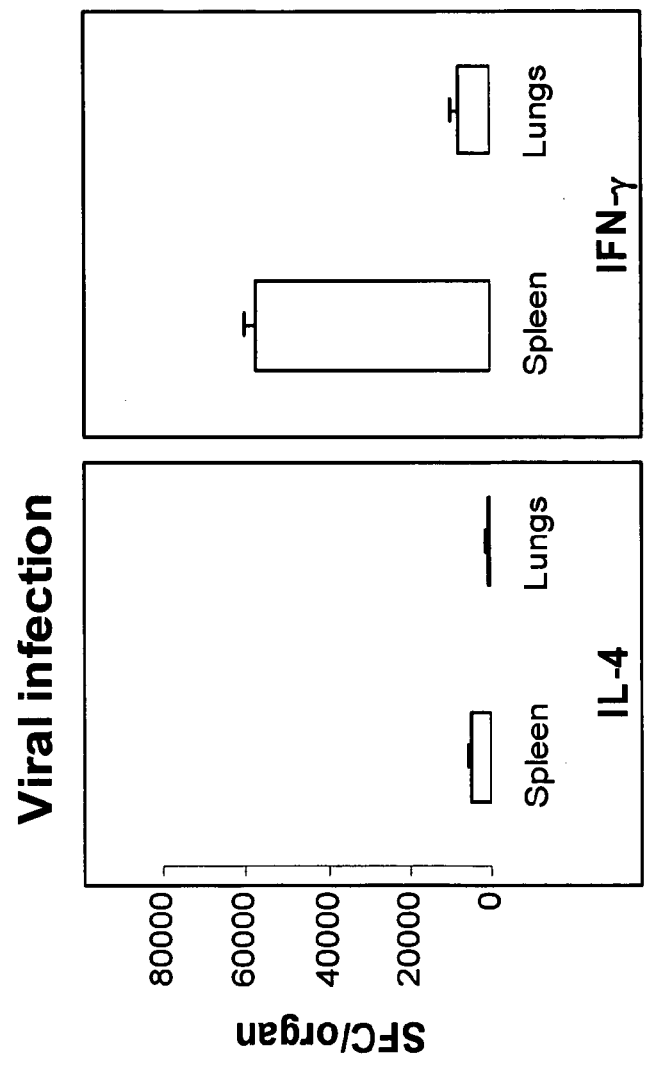

The results in FIG. 19A-19B show that in contrast to viral immunization with an influenza virus strain bearing the cognate peptide, Ig-mediated peptide delivery was ineffective in triggering IFN-γ producing Tc1 cells. However, Ig-peptide administration still resulted in formation of MHC class I-peptide complexes and induced significant NP-specific MHC class I-restricted T cell immunity consisting in IL-4 producing Tc2 cells.

EXAMPLE 19

Shows that in vivo loading of selected APC with disease associated epitopes suppressed an aggravated form of autoimmunity by expanding rather than ablating, epitope-specific autoreactive T.

SJL mice were injected subcutaneously with 200 μl of rat brain homogenate emulsified in Complete Freund's Adjuvant and boosted with 50 ng of pertussis toxin at 6 hours and 2 days. The mice developed an aggravated, progressive form of paralytic disease. Half of the mice received via subcutaneous injection a combination of recombinant immunoglobulins bearing the MBP and the PLP epitopes (recMBP(I-As)-IgG; recPLP(I-As)-IgG), respectively (150 μg/molecule, on day 8, 12, 18 after induction of disease). In panel A, the mean clinical score for treated and non-treated mice is represented, respectively (n=8).

After a period of observation of 70 days, the mice were sacrificed, spleens harvested and elispot analysis carried out as follows: the ELISPOT plates (Millipore, Molsheim, France) were incubated with purified anti-cytokine Abs (4 ug/ml for and anti-IL4, and 8 μg/mg for anti-IFN gamma, from BD Pharmingen) in sterile PBS (50 μl/well) at 4° C. overnight. The next day, the plates were washed 2 times with DMEM media and blocked with 200 μl/well of DMEM complete containing FBS, for an hour at 37° C. Single cell suspension was made from the spleens, red blood cells were lysed, cells washed, counted and incubated at $1\times10^6$/well together with 20 μg/ml of peptides (PLP or MBP) or just with media, to assess the background.

Plates were incubated 72 hours at 37° C., 5% CO2. After 3 days, the plates were Washed 5 times with PBS—tween 20 0.05% (washing buffer) and incubated with 100 μl/well of biotinylated anti-cytokine Abs, 2 μg/ml in PBS—tween 20 0.05% FBS 0.1% (ELISPOT buffer) overnight at 4° C. The next day, the plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. Plates were then allowed to dry at room temperature for 24 hours.

Figures 20A, 20B:
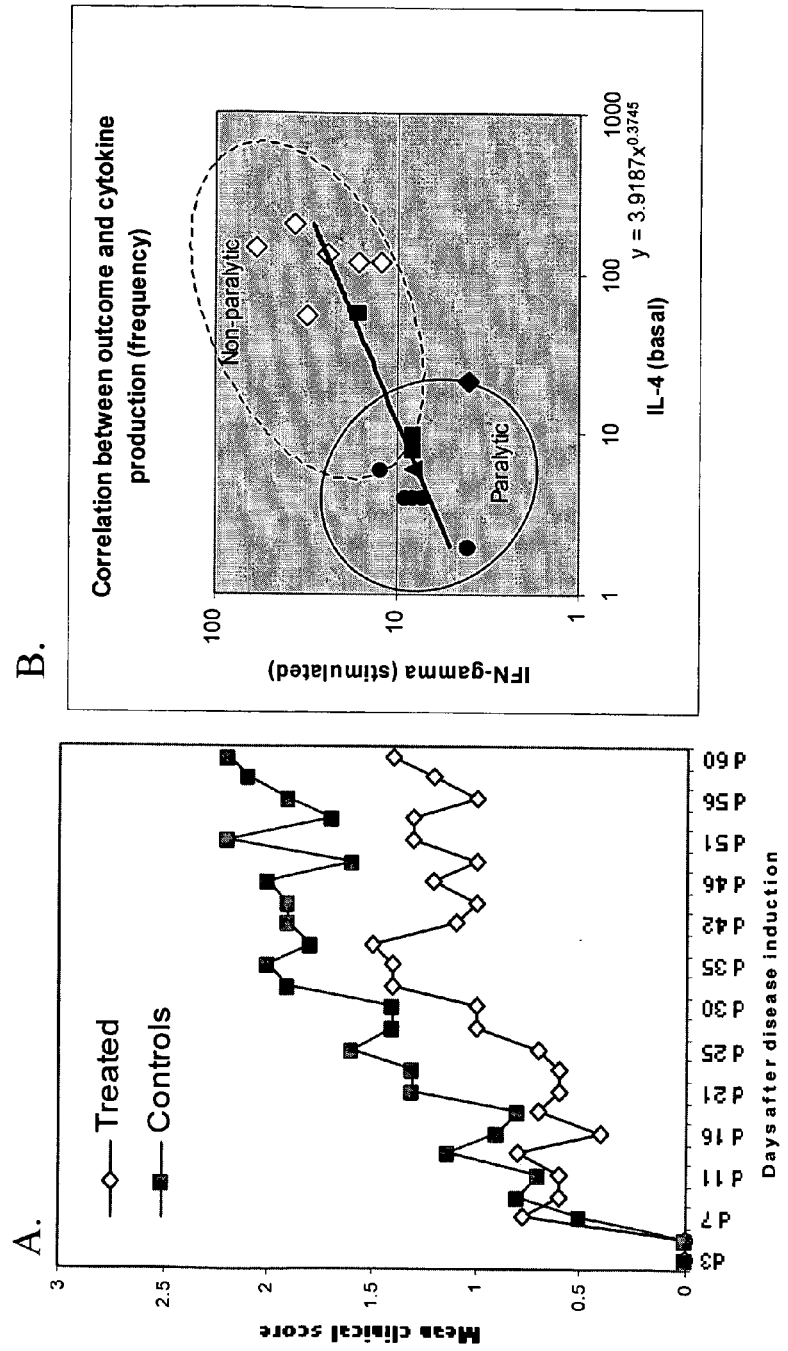
FIGS. 20A-20D show that co-administration of MBP and PLP epitopes by using recombinant IgG curbed the chronic progression of disease.
Figure 20C:
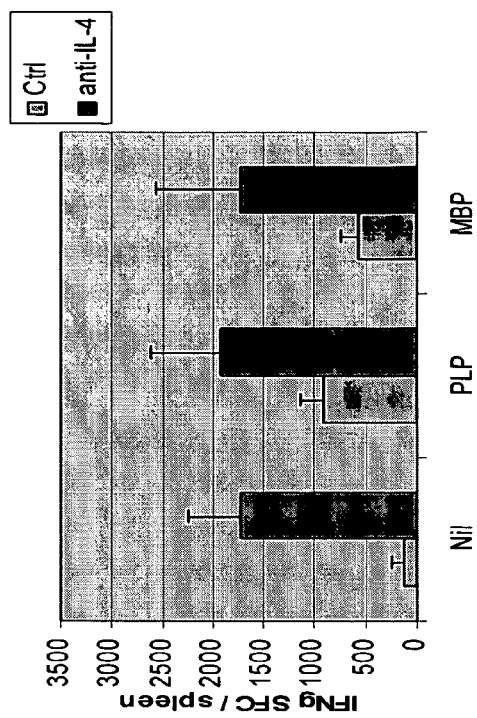
Figure 20D:
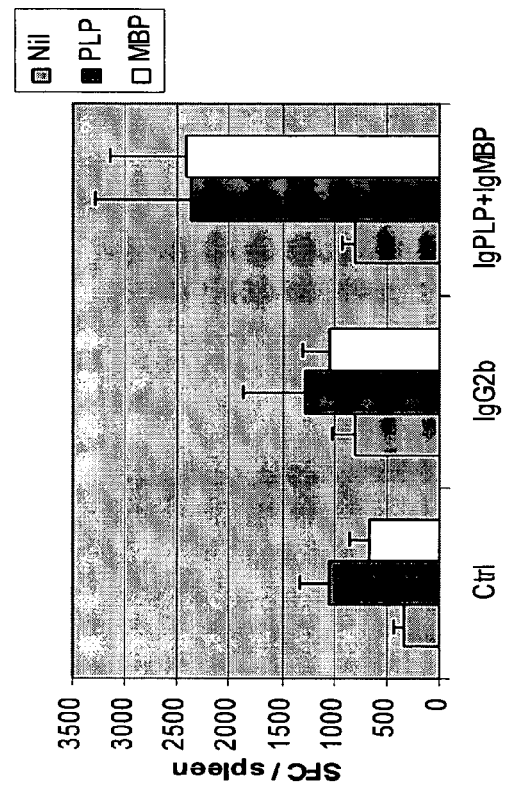

The data were acquired using an automated system (Navitar, Rochester, N.Y.) with ImagePro-Plus) software (Media Cybernetics, Silver Spring, Md.). The results (FIG. 20B)

were expressed as frequency of IL-4 producing T cell colonies in the absence of added PLP peptide plotted against the frequency of IFN-γ-producing T cells in condition of peptide stimulation. Mice progressing to full-blown limb paralysis (score equal to or higher than 1.5) were represented with closed symbols. Mice that did not progress to limb paralysis were represented with open symbols. In FIG. 20C, the total number of IL-4 spot forming colonies/spleen (mean±SEM) in condition of in vitro stimulation was represented with nil, MBP or PLP peptide. An additional control; consisting of splenocytes from mice treated with IgG2b isotype control, has been included. In parallel, in vitro culture was carried out in the presence of neutralizing anti-IL-4 mAb (40 μg/ml) and the number of IFN-γ-producing T cells was represented in the panel D.

The results in FIGS. 20A-D show that co-administration of MBP and PLP epitopes by using recombinant IgG significantly curbed the chronic progression of disease. The mice protected from paralysis developed unexpectedly, an enhanced reactivity to self-epitopes MBP and PLP, manifested by increased basal and peptide-stimulated IL-4 or IFN-γ production, respectively. Finally, the reactivity of IFN-γ-producing T cells is kept in check by IL-4 suggesting a complex immunomodulatory mechanism triggered by IgG-mediated delivery of epitopes.

EXAMPLE 20

Summarizes the impact of IgG/FcγR-mediated delivery of epitopes on the T cell response, based on data provided in the Examples 1-19.

First, the loading of APC T cell response to IgG-mediated delivery of T cell epitopes is controlled by two functionally opposing receptors: ITIM and ITAM Fc (gamma$^+$)-bearing receptors on APC. ITIM$^+$ FcγRIIB limits the degree of activation of T cells and gamma$^+$ FcRs are required for effective formation of MHC-peptide complexes when epitopes are delivered via the IgG backbone. Such in vivo delivery of epitope results in effective formation of MHC—peptide complexes on peripheral CD11c$^+$ and CD11b$^+$ APC, but not thymic APC. However, the interplay between ITIM$^+$ and ITAM$^+$ FcγRs makes the nature and magnitude of resulting T cell response difficult to predict without experimentation.

Figure 21:
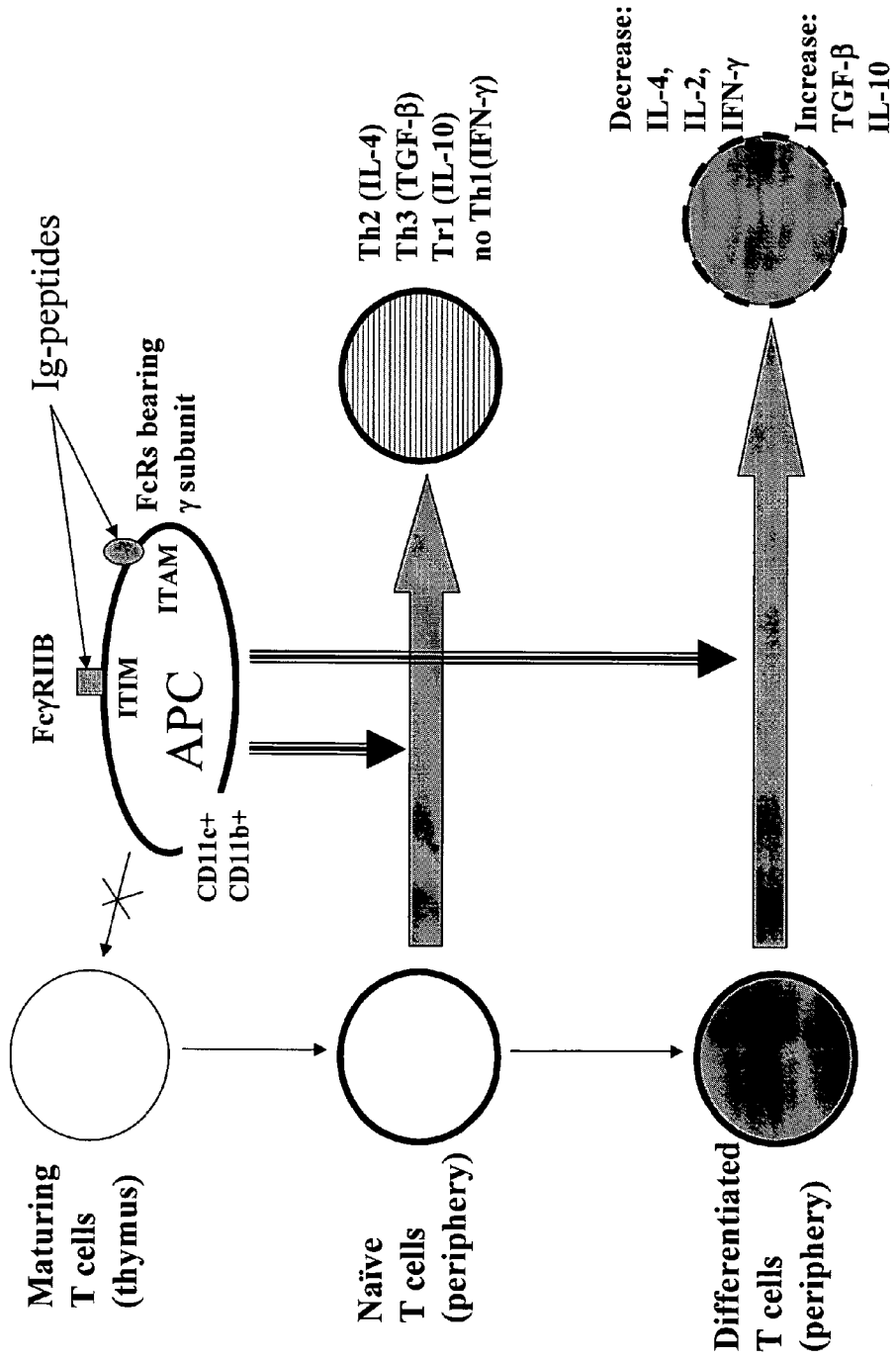
FIG. 21 summarizes the impact of IgG/FcγR-mediated delivery of epitopes on the T cell response, based on data provided in Examples 2-20.

The data in FIG. 21 show that IgG-delivery of peptide epitope results in exposure of T cells to peptide-loaded APC in context of limited co-stimulation, having a differential effect on naive versus activated T cells: 1) de novo induction of Th2, Tc2, Th3, Tr1 cells and, 2) downregulation of activated Th1; Th2 cells with stimulation of activated Tr1 and Th3 cells. The overall effect is immunomodulatory, rather than pro-inflammatory (associated with Th1 and Tc1 immunity).

EXAMPLE 21

Naturally occurring dsRNA bridges the innate with adaptive immune response. Example 21 shows that natural, non-infectious double stranded RNA produced during infection with influenza virus, has substantial effects on the specific immune response to a protein antigen.

Permissive MDCK cells were infected with WSN influenza virus ($10^8$TCID$_{50}$/1×$10^9$ cells) and after 24 hours, the cells were harvested, washed and the total RNA extracted using an RNA separation kit (Qiagen, Valencia, Calif.). The RNA was further purified by treatment with RNAse-free DNAseI (Stratagene, San Diego, Calif.). The single stranded RNA in the samples was then removed by 30 minutes incubation at 37° C. with 5U of S1 nuclease (Ambion, Inc., Austin-Tex.)/μg of RNA. The RNA was analyzed prior to and subsequent to the digestion by gel electrophoresis. The absence of infectious properties of the purified dsRNA was confirmed by standard influenza virus titration. As a control, material purified and treated similarly, from $10^9$ non-infected MDCK cells was used. The concentration of nucleic acid was measured by spectrophotometry ($A_{260\ nm}$) and the absence of endotoxin confirmed by Limulus assay. The purified dsRNA and control RNA were used individually, or as a mixture with gp140 recombinant antigen (25 μg of RNA and 2 μg of antigen in 25 ml of sterile PBS).

After demonstrating lack of infectivity, 40 μg of dsRNA or control RNA were admixed with 40 μg of recombinant truncated antigen (gp140 of HIV envelope) and were administered to BALB/c mice by intranasal instillation (n=3/group). Additional controls were animals immunized with 40 μg of gp140 protein in saline (n=3/group). The mice were boosted once, at 2 weeks after priming. Blood was harvested 2 weeks after the boost, sera prepared and the antibody response against gp140 measured by ELISA. In brief, wells,were coated with antigen (2 μg/ml of gp140) and blocked with SeaBlock (Pierce, Rockford-Ill., catalog #37527). Serial dilutions of serum and bronchoalveolar lavage fluid were incubated for at least 2 hours at room temperature. After washing, the assay was developed with anti-mouse IgG antibody coupled with alkaline phosphatase (Sigma, cat #A7434) followed by addition of substrate (pNPP, Sigma, cat #N2765) and measurement by using an automatic microtiter plate reader (Molecular Devices, ThermoMax) equipped with SoftMax software.

Figure 22:
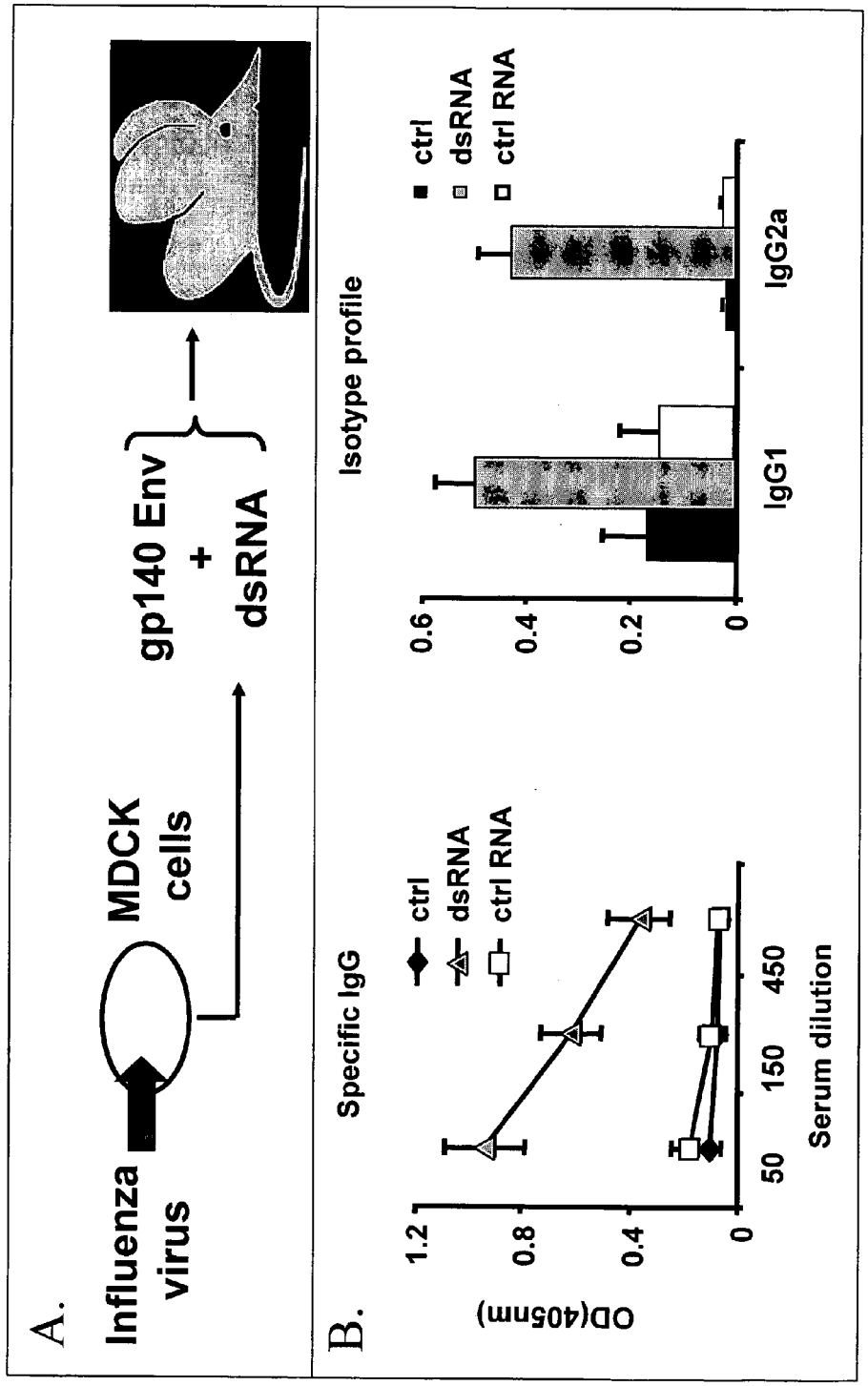
FIG. 22 shows that shows that natural, non-infectious double stranded RNA produced during infection with influenza virus, has substantial effects on the specific immune response to a protein antigen.

In FIG. 22A, the general principle of the experiment is illustrated. In FIG. 22B, the absorption after assay development is represented, corresponding to various serum dilutions, in case of whole IgG. In FIG. 22B, the absorption at 1/50 serum dilution, in case of IgG2a and IgG1 antibody isotypes, is represented.

Overall, the data in FIGS. 22A-B show that natural, non-infectious dsRNA from influenza virus-infected MDCK cells, has an unexpected enhancing effect on the adaptive response to a prototype antigen. Both IgG1 and IgG2a antibody responses were increased showing that a strong T helper1 and T helper 2 response was induced.

EXAMPLE 22

Effects of selected RNA motifs on the innate immune response: heterogeneous motifs. This Example shows, unexpectedly, that different synthetic RNA motifs have a distinct effect on the adaptive specific immune response to a protein antigen.

FIG. 23A shows an extensive library of synthetic RNA motifs, that was grouped in pools and used for a two-tier screening process as follows:
(A) The mice were immunized intratracheally with RNA pools, followed by 2 boosts two weeks apart, carried out by intranasal instillation. The antibody response measured (FIG. 23 B) by ELISA was expressed as mean±SEM of IgG endpoint titers (n=4/group). As controls, dose-matched OVA in sterile PBS was used, OVA with cholera toxin subunit B (CTB) and PBS alone, respectively. In brief, wells were coated with antigen (10 μg/mg of OVA) and blocked with SeaBlock (Pierce, Rockford-Ill., catalog #37527). Serial dilutions of serum and bronchoalveolar lavage fluid were incubated for at least 2 hours at room temperature. After washing, the assay was developed with anti-mouse IgG antibody coupled with alkaline phosphatase (Sigma, cat #A7434) followed by addition of substrate (pNPP, Sigma, cat #N2765) and measurement by using an automatic microtiter plate reader (Molecular Devices, ThermoMax) equipped with SoftMax software.

Figures 23B, 23C, 23D:
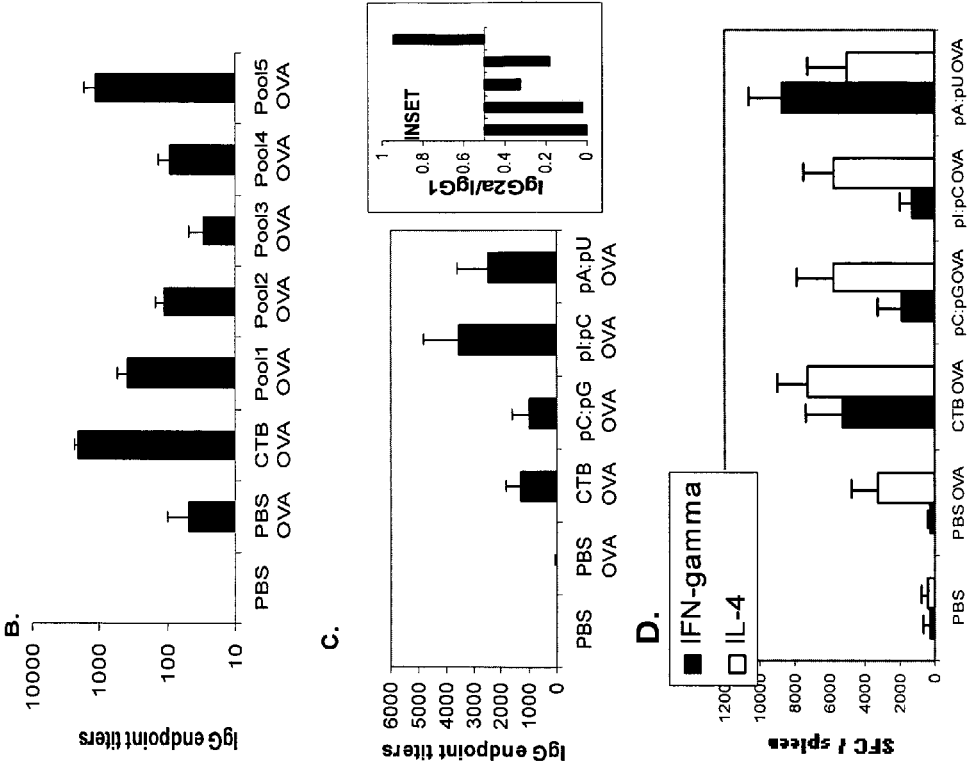
FIGS. 23B-23D show that different synthetic RNAs have an enhancing effect on the B and T cell response to a prototype protein antigen.

(B) The effect of various dsRNA motifs on the induction of antibody response to OVA: the results are expressed as in FIG. 23 C. The data are representative for two independent experiments. INSET: the ratio between mean IgG2a and IgG1 titers to OVA. For this purpose, biotin-conjugated anti-mouse IgG1 and IgG2a antibodies were used followed by incubation with streptavidin-AKP conjugate. The order from left to right is similar as in the main panel in FIG. 23C: PBS OVA, CTB OVA, pC:pG OVA, pI:pC OVA and pA:pU OVA.

(C) The magnitude and profile of T cell response induced by OVA together with various dsRNA motifs, in female C57BL/6 mice. For the measurement of cellular response, splenic cell suspensions were obtained by passing the organ through 70 micron nylon Falcon strainers (Becton Dickinson, cat #352350) followed by lysis of red blood cells with red blood cell lysis buffer (Sigma, cat #R7757). The lymphocytes from the pulmonary associated lymphoid tissue were isolated by collagenase (Sigma, cat #C9891) digestion of lung tissue followed by Ficoll-Paque (Amersham Pharmacia, cat #17-1440-02) gradient centrifugation. The T cell response was measured by ELISPOT analysis as follows: 96-well 45 micron mixed cellulose ester plates (Millipore, cat #MAHA S4510) were coated with 4 µg/ml of rat anti-mouse anti-IFNγ, IL-2 or IL-4 monoclonal antibodies (BD-PharMingen, cat #554430, cat #18161D, cat #554387 respectively). After blocking with 10% FCS in sterile saline for 1 hour at 37° C., spleen cell suspensions were added at $5\times10^5$ cells/well, with or without antigens/peptides. For stimulation, graded amounts of antigen (OVA) were used. At 72 hours after stimulation, the assay was developed with biotinylated rat anti-mouse cytokine antibodies (BD-PharMingen) followed by streptavidin-HRP (BioSource Int., Camarillo, Calif.) and insoluble AEC substrate. The results were measured using an automatic imaging system (Navitar/Micromate) equipped with multiparametric-analysis software (Image Pro, Media Cybernetics). The results are expressed in FIG. 23 D as mean±SEM of the number of IFN-γ and IL-4 spot-forming-colonies (SFC) per spleen (n=4/group). The results are representative for two independent experiments.

The results in FIGS. 23B-D show that different synthetic RNAs have an enhancing effect on the B and T cell response to a prototype protein antigen. In addition, different motifs, comprising specific nucleotide combinations, have specific effects in terms of T1 versus T2 induction and subsequently, immunoglobulin isotype switching.

EXAMPLE 23

Use of selected synthetic RNA motifs facilitates the induction of MHC class I-restricted Tc1 cells, producing IFN-γ.

(A) Cross-priming stimulated by dsRNA motifs was studied in BALB/c mice treated (priming plus 2 boosts) with 10 µg of recombinant-engineered HIV gp140 antigen together with pA:pU. The response was measured by ELISPOT analysis as described in Example 22, using in vitro stimulation with the MHC class I-restricted cognate peptide R10K derived from the V3 domain. As a control, dose-matched gp140 antigen was used. The results are expressed in FIG. 24A as mean±SEM of the number of IFN-γ and IL-4 SFC/spleen (n=4/group).

(B) Cross-priming stimulated by dsRNA motifs was studied in C57BL/6 mice treated with 100 µg of whole OVA together with pA:pU by ELISPOT analysis as described in Example 22, using in vitro stimulation with the MHC class I-restricted peptide SIINFEKL (Seq. 1D No.). As a control, dose-matched OVA antigen in saline or sterile PBS was used. The results are expressed in FIG. 24B as mean±SEM of the number of IFN-γ and IL-4 SFC/spleen (n=4/group).

Figures 24A, 24B:
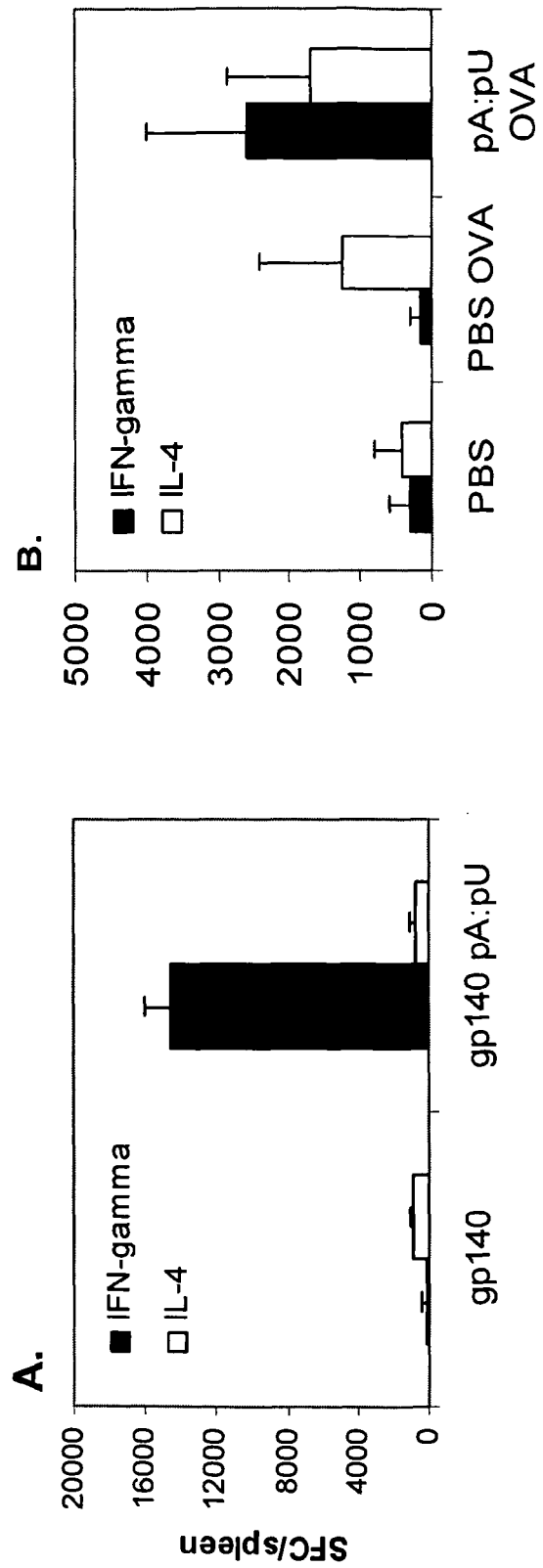
FIGS. 24A-24B show effects of selected RNA motifs on the innate immune response.

The results in FIGS. 24A-B show that a selected synthetic RNA motif was able to promote increased T cell immunity to different MHC class I-restricted peptides encompassed within larger antigens (polypeptides). This immune response comprised a Tc1 component, consisting in IFN-γ-producing MHC class I-restricted T cells.

EXAMPLE 24

Shows that unexpectedly, different synthetic RNA motifs bind to different receptors; in other words, there are multiple receptors that discriminate among RNA motifs.

In vitro binding of CD 11b$^+$ APC by fluorescently-tagged pA:pU was measured by FACS analysis. The MACS-separated APC were incubated at 4° C. for 30 minutes with 10 µg/mg of tagged pA:pU ([pA:pU]-F), washed and analyzed. Alternatively, APC were preincubated for 10 minutes with 20 or 100 µg/mg of non-tagged pA:pU, pA or pI:pC respectively, before staining with tagged pA:pU and FACS analysis. The profiles of stained (open area), non-stained (filled area) cells and the percentage of highly stained APC were represented in each panel, with logarithmic x axis. The data are representative of two independent measurements with 10,000 events acquired for each sample.

Materials:
1. Mouse CD11b, CD11c Magnetic Separation Beads: Miltenyi Biotec, cat #130-049-601, cat #130-052-001 respectively;
2. ULYSIS Nucleic Acid Labeling Kit: Alexa 488, Molecular Probes cat #U21650;
3. RNA Motifs:
   pA:pU, (Sigma, Lot #22K4068);
   pI:pC, (Sigma, Lot#52K4047);
   pA, (Sigma, Lot#22K4022);
4. FACS Buffer: PBS, 1% FCS, 0.1% sodium azide;
5. MACs buffer: PBS, 2 mM EDTA, 0.5% BSA;
6. Collagenase Buffer: 0.225 mg BSA, 0.0062 mg collagenase in 50 ml RPMI; and,
7. 70 um cell strainer: (Falcon/Becton Dickinson, cat #352350.

Methods:
I. Labeling of RNA Motifs:
   1. In the following protocol, each RNA motif was tagged with the ULYSIS Alexa 488 label.

II. Splenocyte Preparation:
   1. Isolate splenocytes and lung cells from 4 female C57 BL/6 mice;
   Lung cells, in contrast to splenocytes, must be minced and incubated in collagenase buffer for 30 minutes at 37° C. prior to the following step;
   Pass through 70 um falcon cell strainer;
   Wash and resuspend in MACS buffer:
   2. Label with either CD11b or CD 11c specific MACS beads following suggested protocol;

3. Cells were then treated with:
   Non-tagged pA, pA:pU, or pI:pC (20 or 100 ug/ml) for 10 minutes at room temperature;
   ULYSIS tagged pA or pA:pU was added at 1.5 ug/tube and 10 ug/tube, respectively, to match dye:dsRNA ratio of each motif.
4. Mix and incubate 30 minutes on ice.
5. Wash once and resuspend in FACS buffer III. Flow Cytometry:
   Run flow cytometric analysis to determine/compare competitive inhibition of tagged versus non-tagged RNA motifs and cell receptor binding.

Figure 25:
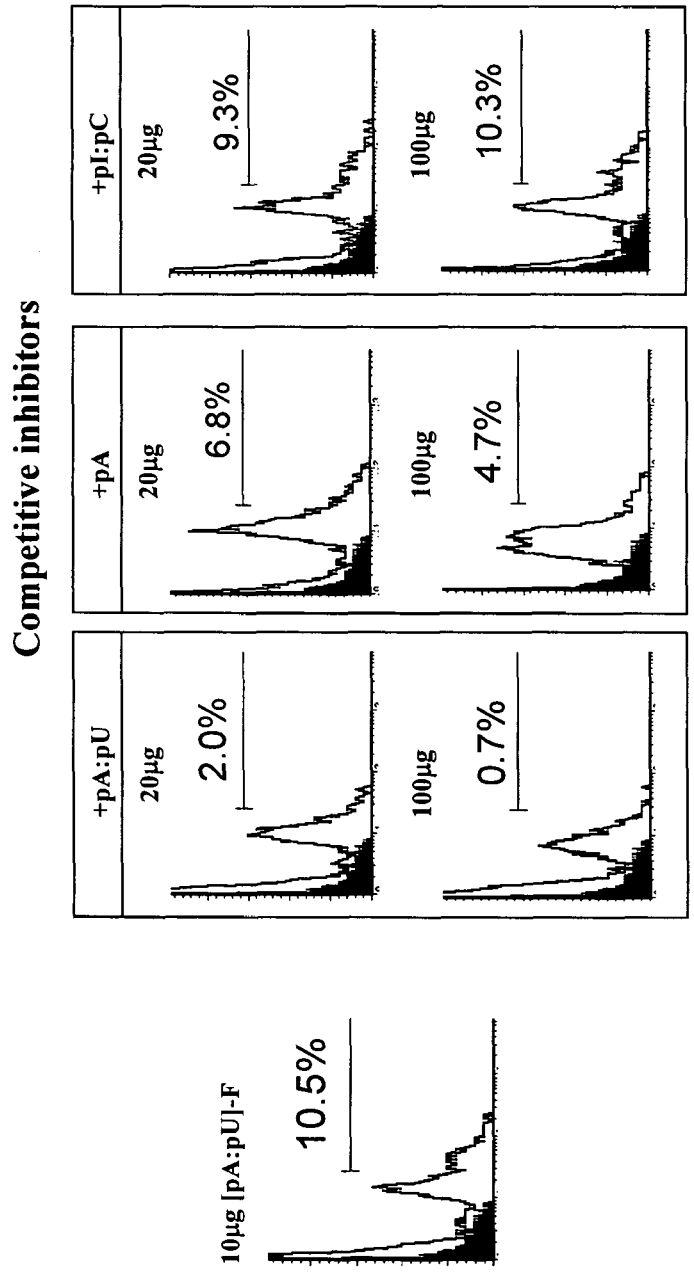
FIG. 25 shows that distinct RNA motifs bind to different receptors on antigen presenting cells.

The results in FIG. 25 show that pA:pU and pI:pC bind to different cellular receptors. Since pI:pC binds to TLR3, it results that additional receptors distinct from TLR3 are involved in RNA recognition immune function.

EXAMPLE 25

Shows that selected synthetic RNA motifs trigger in vivo expression of chemokine genes, of importance for immunological activity.

Local up-regulation of chemokine gene-expression by dsRNA motifs was measured by DNA array technique using RNA from the pulmonary tissue, extracted one day after the administration via the respiratory tract. Total RNA was isolated from lungs using an RNeasy kit (Qiagen, Valencia, Calif.). The RNAs were further purified by treatment with RNase-free DNase I (Stratagene, San Diego, Calif.). DNA array was performed by using the Nonrad-GEArray kit from SuperArray Inc. (Bethesda, Md.). Briefly, cDNA probes were synthesized using MMLV reverse transcriptase with dNTP mix containing biotin-16-dUTP. The GEArray membranes were prehybridized at 68° C. for 1-2 hours. The hybridization was carried out by incubation of the membranes with biotin-labeled cDNA. The hybridized membranes were washed in 2×SSC-1% SDS twice and 0.1×SSC-0.5% SDS twice. The membranes were further incubated with alkaline phosphatase-conjugated streptavidin (BioSource Int., Camarillo, Calif.) and finally developed with CDP-Star chemiluminescent substrate. The intensity of signal was measured with Image-Pro analysis system equipped with Gel-Pro software (Media Cybernetics, Silver Springs, Md.).

The results are expressed as fold-increase of gene expression, over expression levels measured in the pulmonary tissue of non-treated mice. The pattern of chemokine expression triggered by dsRNAs (50 μg of pA:pU and pI:pC, respectively) was compared to that induced by 1 μg of LPS. The chemokines that selectively bind to receptors on Th1 and Th2 cells were indicated with continuous and interrupted contours, respectively.

Figure 26:
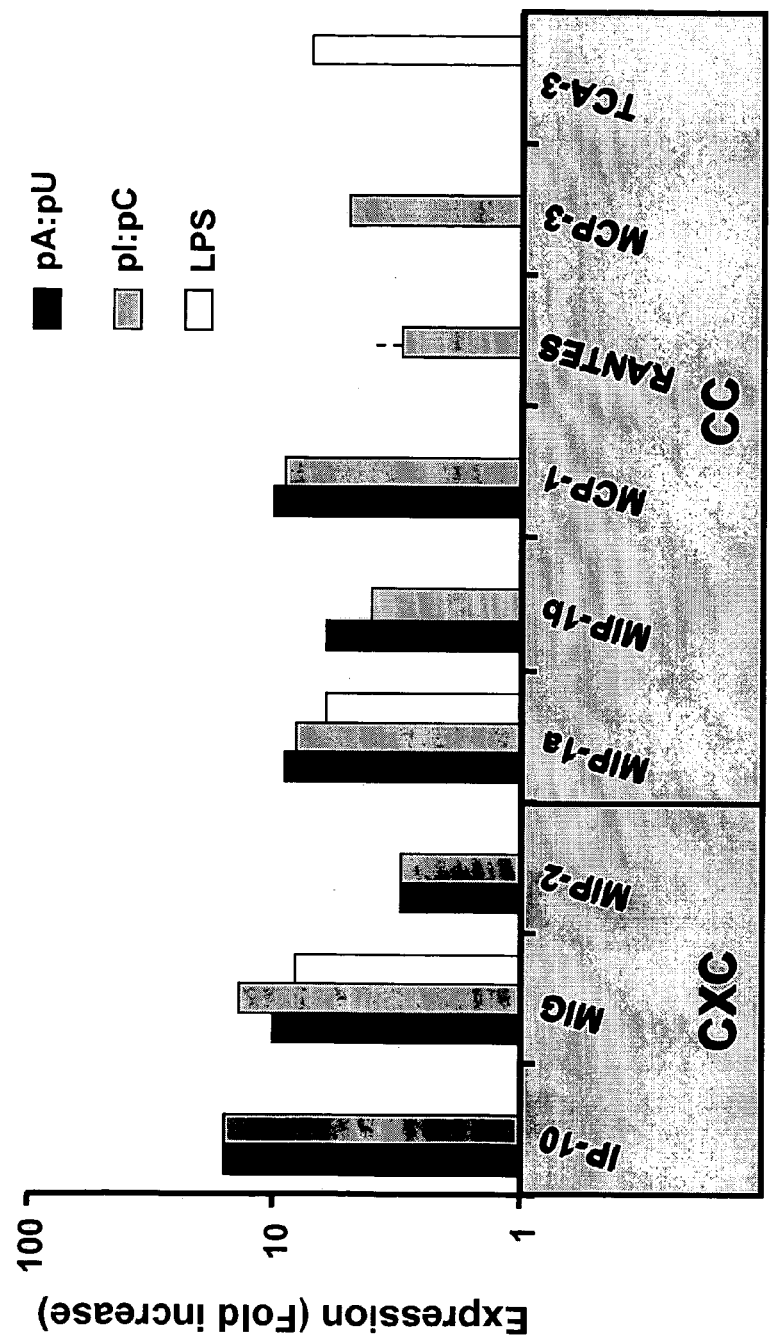
FIG. 26 shows that distinct RNA motifs induce differential upregulation of chemokines.

The results in FIG. 26 show that pA:pU and pI:pC trigger expression of a wide range of chemokines and that the expression pattern is motif-dependent and different from that elicited by LPS (endotoxin).

EXAMPLE 26

Shows that selected synthetic RNA motifs mobilize an immune defense that is capable to control infection with a pulmonary virus.

dsRNA motifs display differential ability to mobilize immune defense against influenza virus infection. C3H/HeJ mice were treated via the respiratory route with 50 μg of pI:pC, pA:pU or 50 μl of saline one day before and after pulmonary infection with a sublethal dose of influenza virus. For virus challenge, C57BL/6 and TLR4−/− $C_3H$/HeJ mice under Metofane anesthesia were infected with sublethal doses ($10^4$ tissue culture infective doses 50%—$TCID_{50}$) of live WSN virus, via the nasal route. On day 5 after infection, the mice were sacrificed, lungs retrieved, homogenized and stored at −70° C. The virus titers were measured by 48-hour incubation of serial dilutions of samples with permissive MDCK cells, followed by standard hemagglutination with chicken red blood cells (From Animal Technologies). The endpoint titers were estimated in triplicate measurements by interpolation and expressed as $TCID_{50}$/organ (means±SEM; n=6/group; results are representative of two independent studies in $C_3H$/HeJ TLR-4−/− and competent mice). Similar results were obtained in TLR4 competent, C57BL/6 mice.

Figure 27:
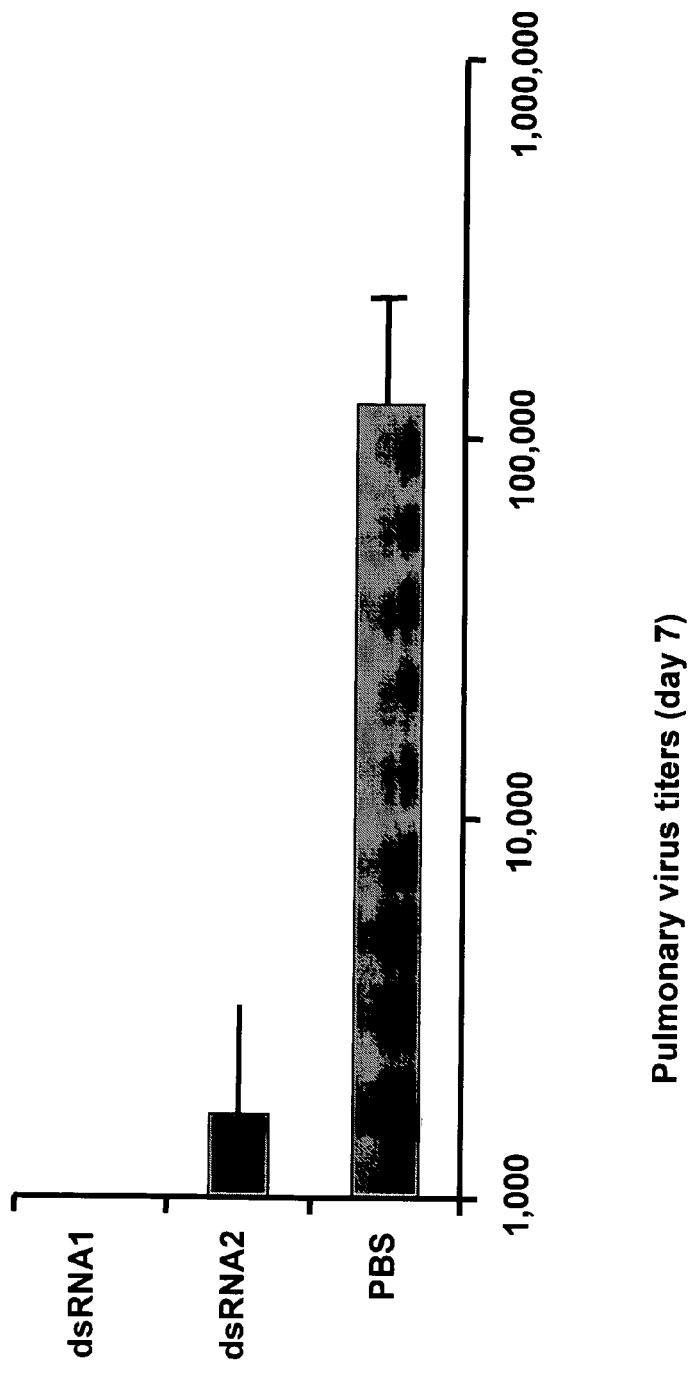
FIG. 27 shows that the control of replication of influenza virus can be achieved by using selected synthetic RNA motifs.

Thus, the results depicted in FIG. 27 show that the control of replication of influenza virus can be achieved by using selected synthetic RNA motifs (dsRNA1 is pA:pU and dsRNA2 is pI:pC).

EXAMPLE 27

Shows that co-administration of selected synthetic RNA motifs breaks tolerance to high dose standard antigen.

dsRNA motifs prevent high-zone tolerance in mice injected with human IgG. The mice (C57BL/6) were initially injected intravenously with a toleragenic dose of 200 μg of hIgG alone (closed symbols) or together with 100 μg of pI:pC or pA:pU (open symbols) and subsequently boosted subcutaneously with an immunogenic dose of 100 μg of hIgG emulsified in CFA. The titer of antibodies against hIgG was measured by ELISA (as detailed in the Example 23, with the difference consisting in use of 10 μg/ml of hIgG for coating) at various intervals after the first injection. As a control, mice immunized with 100 μg of hIgG emulsified in CFA were included and represented the maximal titer on the graph (interrupted line).

Figure 28:
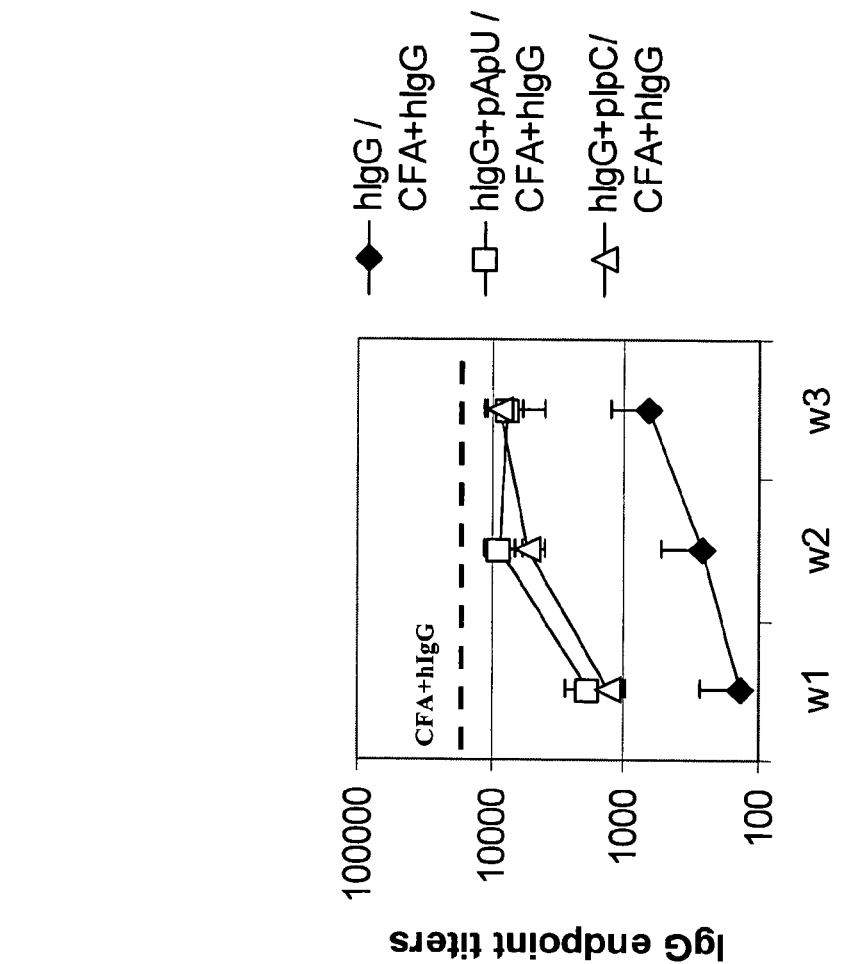
FIG. 28 shows that selected synthetic RNA motifs pI:pC and pA:pU largely prevent high zone tolerance that is usually associated with administration of large amounts of purified protein.

The results are represented in FIG. 28 as means±SEM of endpoint titers (n=5/group). Similar results were obtained in TLR4 deficient (C3H/HeJ) and LPS-responsive C3H/SnJ mice. Thus, the results in FIG. 28 show that selected synthetic RNA motifs pI:pC and pA:pU largely prevent high zone tolerance that is usually associated with administration of large amounts of purified protein.

EXAMPLE 28

Shows that selected RNA motifs induce differential cytokine production by human APC.

Human THP-1 monocytic cells, following differentiation, .Were incubated with different concentrations of synthetic RNA (pA:pU, pI:pC or pA) for 24 hours, and the cell supernatants collected. The concentration of IL-12 and TNF-α were measured by ELISA. The results are expressed in FIG. 29 as pg/ml (concentration) for each cytokine and culture condition.

Materials:
1. THP-1 Human monocytic cell line: ATCC, cat #TIB-202;
2. IL-12 Cytokine: Human ELISA, IL-12 ultra sensitive (US) cat #KHC0123;
3. TNF alpha Cytokine: Human ELISA, TNF alpha cat #KHC3012;
4. RNA Motifs:
   pA:pU, (Sigma, Lot #22K4068);
   pI:pC, (Sigma, Lot #52K4047); and,
   pA, (Sigma, Lot #22K4022).

Method:
1. The THP-1 cells were allowed to differentiate following addition of 10 ng/ml PMA in media containing 10% FCS.
2. After gently washing cells and adding non-FCS containing Media (HL-1), treatments (RNA motifs and controls) were added at concentrations of from 3 to 100 μg/mg on top of adherent THP-1 cells.
3. After 24 hours incubation, cell supernatants were harvested and IL-12 and TNF alpha concentrations were measured by ELISA.

Figure 29:
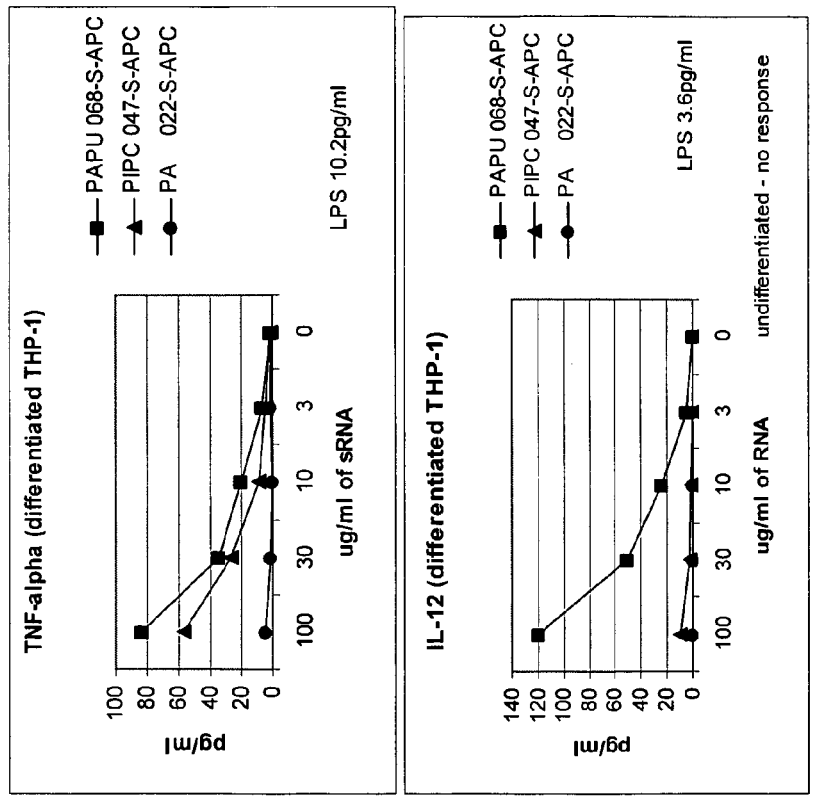
FIG. 29 shows that selected synthetic RNA motifs effect on human monocytic cells.

The results in FIG. 29 show selected synthetic RNA motifs effect on human monocytic cells; in addition, this effect is heterogeneous, depending on the chemical structure of the motifs (nucleotide composition). Selected but not all synthetic RNA motifs are able to trigger IL-12 production, an important T1 regulatory cytokine, by human monocytic cells.

EXAMPLE 29

Shows that two distinct synthetic RNA motifs bind to human THP-1 monocytic cells in a manner demonstrating interaction with different receptors.

THP-1 cells were incubated at for 15 minutes at room temperature with different amounts of non-labeled synthetic RNA. Subsequently, tagged pA:pU was added for 30 minutes at 4° C., cells washed and the fluorescence quantified by FACS analysis. The results are expressed in FIGS. 30A-30B as histograms corresponding to the large cell subset (A) and total cell population (B). Percentages of stained cells were represented on each Figure.

Materials:
1. ULYSIS: Nucleic acid fluorescent label (Molecular Probes, cat #U-21650).
2. RNA Motifs:
   pA:pU, (Sigma, Lot #22K4068);
   pI:pC, (Sigma, Lot # 52K4047);
3. Detoxi-Gel column: (Pierce, cat #20344).

Method:
Labeling of Polyadenylic-Polyuridylic Acid (pA:pU):
1. Following removal of endotoxin using a Detoxi-Gel column, pA:pU was labeled with the Alexa Fluor 488 fluorescent dye using the ULYSIS nucleic acid labeling system.
2. Briefly:
   The pA:pU was precipitated using sodium acetate and ethanol at 70° C.;
   The pA:pU was heat denatured and labeled with the Alexa Fluor 488 reagent at 90° C.; and,
   The reaction was stopped and the labeled pA:pU was ethanol precipitated.

Cell Treatment:
1. THP-1 cells were suspended at $2 \times 10^6$ cells/ml;
2. 50 μl of above suspension ($5 \times 10^4$ cells) were placed in 12×75 mm tubes;
3. Non-tagged pA:pU or pI:pC were added to the THP-1 cells at a concentration of either 20 or 100 μg/mg and incubated 15 minutes;
ULYSIS labeled pA:pU was added at a concentration of 100 ug/ml for 30 minutes on ice.
4. The THP-1 cells were washed once and suspended in FACS buffer followed by flowcytometric analysis to determine relative fluorescent differences between different treatment populations.

The results in FIGS. 30A-30B show that non-tagged pA:pU but not non-tagged pI:pC was able to compete out the binding of tagged pA:pU to human THP-1 monocytic cells, both at the level of large cell subset and whole population.

EXAMPLE 30

Shows how the adjuvant synthetic RNA should be prepared and purified prior to use in its most effective format.

The bulk synthetic RNA material is obtained by standard methods of organic synthesis. Afterwards, the material is dissolved in sterile endotoxin-free saline, passed through endotoxin removal columns until the concentration of LPS is below 0.005EU/μg. The measurement of LPS is carried out by standard Limulus assay. Subsequently, the material is fractionated by a series of centrifugation steps through filters of defined porosity (see FIG. 31).

A useful fraction comprises synthetic RNA of less than 20 to maximum 100 bp size, however, larger RNA fragments may be used. After purification, the material is measured and Validated on standard assays: spectrophotometry (OD260 nm); gel electrophoresis; endotoxin quantitation by Limulus assay; bioactivity on human THP-1 cells (as in Example 28).

EXAMPLE 31

Shows that unexpectedly, different fractions of a selected synthetic RNA compound are endowed with different biological activity, based on size.

Differentiated human THP-1 monocytic cells were incubated with different concentrations of synthetic RNA (pA:pU, fractionated as described in the Example 30) for 24 hours, and the supernatants collected. The concentration of TNF-α was measured by ELISA using BioSource International kits (Camarillo, Calif.). The results are expressed in FIG. 32 as pg/ml (concentration) for each culture condition.

The results depicted in FIG. 32 show that lower molecular weight fractions of a selected synthetic RNA compound are endowed with higher biological activity, in terms of cytokine production, by human monocytic THP-1 cells.

EXAMPLE 32

Selected synthetic RNA motifs have, unexpectedly, a different immune profile in regard to generation of anti-RNA antibodies.

BALB/c mice were immunized intraperitoneally and subcutaneously with 50 μg+50 μg of hIgG and synthetic RNA (pI:pC or pA:pU) and serum samples were prepared 1 week later. As a control, mice injected with hIgG in saline were used. The anti-hIgG, and dsRNA IgG antibody titers against pA:pU, pI:pC, pA and hIgG were measured by ELISA. In brief, wells were coated with antigen (10 μg/mg of hIgG or synthetic RNAs) and blocked with SeaBlock (Pierce, Rockford, Ill., catalog #37527). Serial dilutions of serum and bronchoalveolar lavage fluid were incubated for at least 2 hours at room temperature. After washing, the assay was developed with anti-mouse IgG antibody coupled with alkaline phosphatase (Sigma, cat #A7434) followed by addition of substrate (pNPP, Sigma, cat #N2765) and measurement by using an automatic microtiter plate reader (Molecular Devices, ThermoMax) equipped with SoftMax software.

The results are expressed in FIG. 33 as mean±SEM of endpoint titers (n=3/group). The results in FIG. 33 show that pI:pC but not pA:pU induced antibody response against itself, with a cross-reactive component against another RNA motif.

EXAMPLE 33

In vivo loading of APC by recombinant IgG results in generation of Tc1 type of MHC class I responses only when additional conditions are satisfied.

BALB/c mice were immunized with 50 ug of recIgG-NP (Kd) subcutaneously, admixed with 50 ug of selected synthetic RNA (pA:pU or pI:pC). As a control, naive mice or mice immunized with recombinant IgG only were used. At 3 weeks after immunization, the T cell response was measured by ELISPOT analysis as follows: the ELISPOT plates (Millipore, Molsheim, France) were incubated with purified anti-cytokine Abs (4 ug/ml for anti-IL4, and 8 μg/mg for anti-IFN gamma, from BD Pharmingen) in sterile PBS (50 μl/well) at 4° C. overnight. The next day, the plates were washed 2 times with DMEM media and blocked with 200 μl/well of DMEM complete containing FBS, for an hour at 37° C. Single cell suspension was made from the spleens, red blood cells were lysed, cells washed, counted and incubated at $5 \times 10^5$/well together with NP 147-155 peptide or just with media, to assess the background. Plates were incubated 72 hours at 37° C., 5% CO2. After 3 days, the plates were washed 5 times with PBS—tween 20 0.05% (washing buffer) and incubated with 100 μl/well of biotinylated anti-cytokine Abs, 2 μg/ml in PBS—tween 20 0.05%—FBS 0.1%(ELISPOT buffer) overnight at 4° C.

The next day, the plates were washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus software (Media Cybernetics, Silver Spring, Md.). The frequency of cytokine producing T cells reacting to NP peptide was measured and expressed against the amount of peptide used for stimulation. The results are expressed as means±SEM of triplicates (n=3 mice/group).

Figures 34A, 34B:
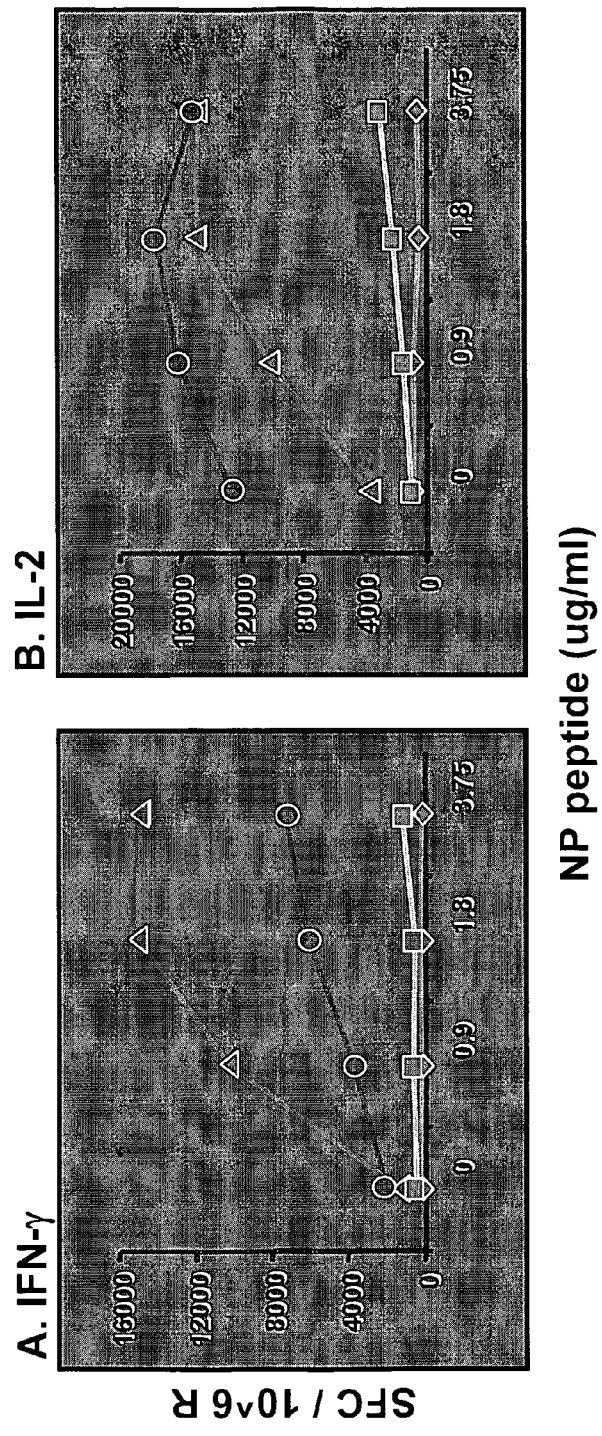
FIGS. 34A-34B show that co-use of selected synthetic RNAs promote effective induction of IL-2 and IFN-gamma subsequent to IgG mediated delivery of an MHC class I-restricted epitope.

As shown previously in FIG. 19, the administration of recombinant IgG bearing the NP MHC class I-restricted epitope resulted in generation of Tc2 immunity but not Tc1 response, implying in vivo formation of class I-peptide complexes with a specific co-stimulation profile. The results in FIGS. 34A and 34B show that co-use of selected synthetic RNAs promoted effective induction of IL-2 and IFN-gamma subsequent to IgG mediated delivery of an MHC class I-restricted epitope (dsRNA1 is pA:pU and dsRNA2 is pI:pC).

EXAMPLE 34

Effective formation of MHC class I-peptides and instruction of the resulting T cell response by simultaneous manipulation of APC loading via FcgammaR and activation via RNA receptors.

Splenic APC were isolated from naive BALBc mice and pulsed ex vivo overnight with 1 ug NP peptide, or 50 μg recIgG-NP (Kd) with or without 50 μg/mg selected synthetic dsRNA (pA: pU). The cells were washed and $5 \times 10^6$ cells were administered by s.c. and i.p. injection equal amount, to naive BALB/c mice. The response was measured 3 weeks later by ELISPOT analysis as follows: the ELISPOT plates (Millipore, Molsheim, France) were incubated with purified anti-cytokine Abs (4 μg/mg for anti-IL4, and 8 μg/mg for anti-IFN gamma, from BD Pharmingen) in sterile PBS (50 μl/well) at 4° C. overnight. The next day, the plates were washed 2 times with DMEM media and blocked with 200 μl/well of DMEM complete containing FBS, for an hour at 37° C. Single cell suspension was made from the spleens, red blood cells were lysed, cells washed, counted and incubated at $5 \times 10^5$/well together with 30 μg/ml, 10 μg/ml, or 3 μg/ml NP peptide. or just with media, to assess the background. Plates were incubated 72 hours at 37° C., 5% CO2. After 3 days the plates were washed 5 times with PBS—tween 20 0.05% (washing buffer) and incubated with 100 μl/well of biotinylated anti-cytokine Abs, 2 μg/ml in PBS—tween 20 0.05%—FBS 0.1%(ELISPOT buffer) overnight at 4° C. The next day the plates were washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus) software (Media Cybernetics, Silver Spring, Md.). The results are expressed in FIG. 35 as frequency of cytokine producing spot forming colonies against the concentration of peptide used for ex vivo stimulation (mean±SEM, n=3 mice/group). In addition, the mean area/colony versus the concentration of peptide used for stimulation is plotted, for both IFN-gamma and IL-4 (arbitrary units).

Figure 35:
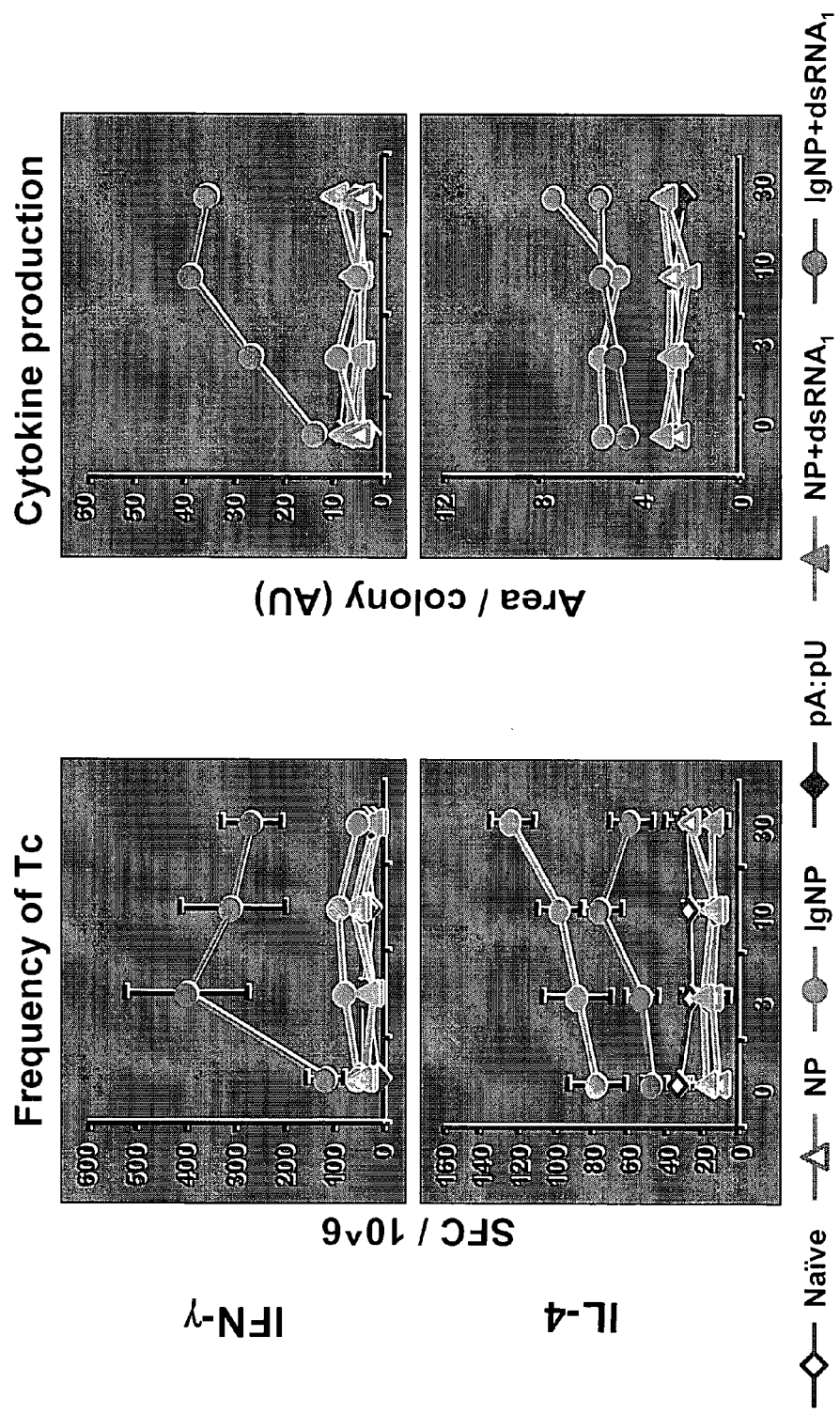
FIG. 35 shows that ex vivo APC loading by recombinant IgG is more effective in formation of MHC class I-peptide complexes and generation of Tc response, compared to use of free peptide itself.

The results in FIG. 35 show that ex vivo APC loading by recombinant IgG is significantly more effective in formation of MHC class I-peptide complexes and generation of Tc response, compared to use of peptide itself. In addition, the mere formation of MHC class I-peptide complexes subsequent to epitope delivery via IgG/FcgammaR results in differentiation of Tc2 cells producing IL-4 but not MN-gamma. Simultaneous treatment of APC with selected synthetic RNA results in broadening of the T cell profile, to IFN-gamma producing Tc1 cells.

EXAMPLE 35

Shows that co-priming with IgG-peptide together with a selected co-stimulatory motif resulted in more effective secondary expansion of MHC class I-restricted T cells subsequent of virus infection.

BALB/c mice were injected with recIgG-NP(Kd), pA:pU separately, or in combination (50 ug/injection). As a control, naive mice were used; Three weeks after treatment, the mice were infected with 104 TCID50 of A/WSN/32 H1N1 influenza virus, via the respiratory tract. Four days after infection, the T cell profile in the spleen was measured by ELISPOT analysis subsequent to ex vivo stimulation with NP peptide as follows: the ELISPOT plates (Millipore, Molsheim, France) were incubated with purified anti-cytokine Abs (4 ug/ml for anti-IL2 and anti-IL4, and 8 μg/mg for anti-IFN gamma, from BD Pharmingen) in sterile PBS (50 μl/well) at 4° C. overnight. The next day, the plates were washed 2 times with DMEM media and blocked with 200 μl/well of DMEM complete containing FBS, for an hour at 37° C. Single cell suspension was made from the spleens, red blood cells were lysed, cells washed, counted and incubated at $5 \times 10^5$/well together with 20 μg/ml NP peptide or just with media, to assess the background. Plates were incubated 72 hours at 37° C., 5% CO2. After 3 days, the plates were washed 5 times with PBS—tween 20 0.05% (washing buffer) and incubated with 100 μl/well of biotinylated anti-cytokine Abs, 2 μg/ml in PBS—tween 20 0.05%—FBS 0.1% (ELISPOT buffer) overnight at 4° C. The next day the plates were, washed five times with washing buffer and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus) software (Media Cybernetics, Silver Spring, Md.). The results are expressed in FIG. 36 as frequency of NP-specific MHC class I-restricted T cells forming cytokine producing colonies (means±SEM, n=4 mice/group).

Figure 36:
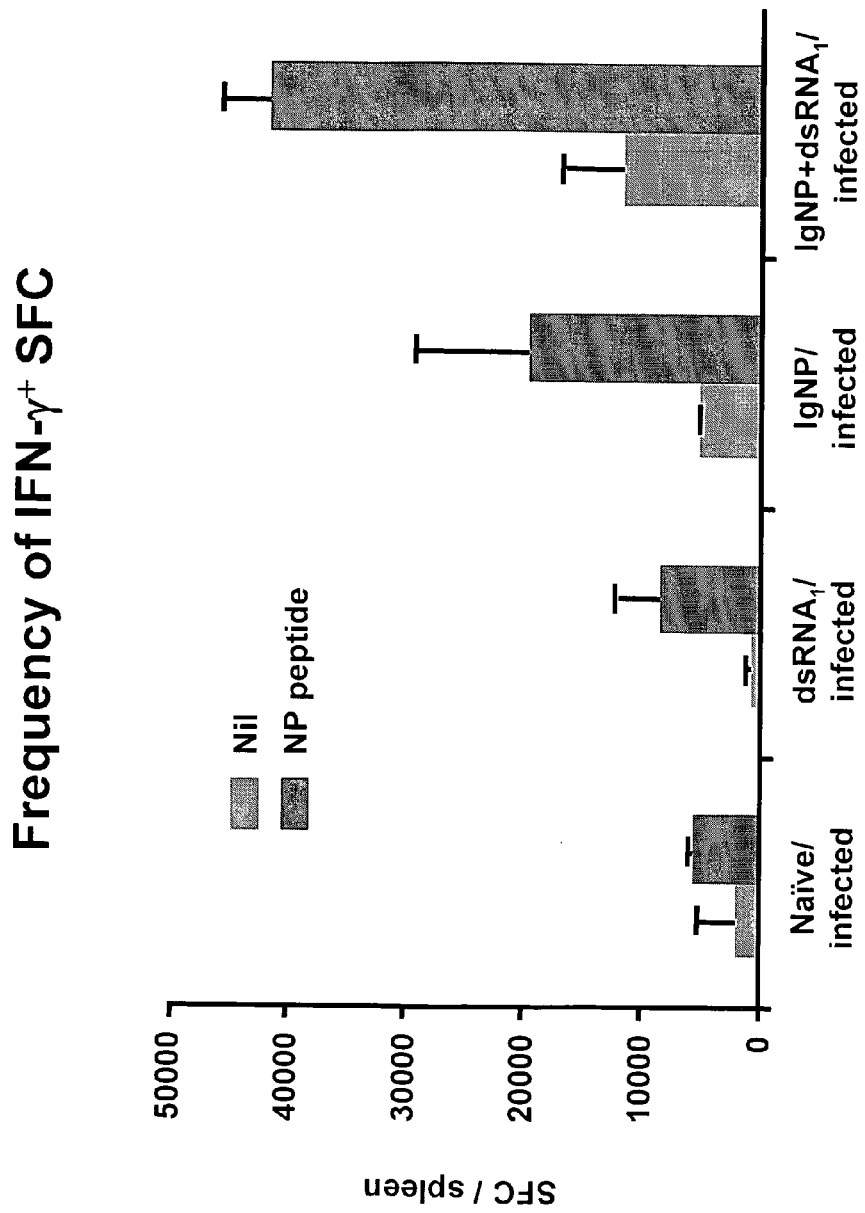
FIG. 36 show that IgG mediated delivery of a class I restricted epitope is most effective in priming class I restricted Tc1 responses when co-administration of selected synthetic RNA was carried out.

The results in FIG. 36 show that IgG mediated delivery of a class I restricted epitope is most effective in priming class I restricted Tc1 responses when co-administration of selected synthetic RNA was carried out. Such primed precursors were rapidly expanded subsequent to infection with influenza virus.

EXAMPLE 36

Shows that the most effective priming of cytotoxic lymphocytes recognizing an MHC class I-restricted epitope occurs by co-administration of selected RNA motif together with peptide epitope inserted within the IgG backbone.

BALBc mice were immunized and challenged with recIgG-NP (Kd) as in the previous Example and sacrificed 4 days after influenza virus infection. The splenocytes were prepared, suspended in HL-1 medium at 5 million/ml and co-incubated for 5 days with 10 µg/mg of NP 147-155 peptide and in presence of 5U/mg of recombinant IL-2. Splenocytes from 4 mice/group were pooled and incubated in flasks.

After expansion, viable cells were recovered by Ficoll gradient centrifugation, washed and incubated for 5 hours in V-bottom plates, in various numbers, with a fixed number of sp20 target cells with or without NP peptide (20 µg/ml). The supernatants were harvested after plate centrifugation, and the concentration of LDH measured by using a Promega kit (cat #G1780). The results are expressed as percent specific lysis at different E: T ratios (Effector to Target ratio).

Figure 37:
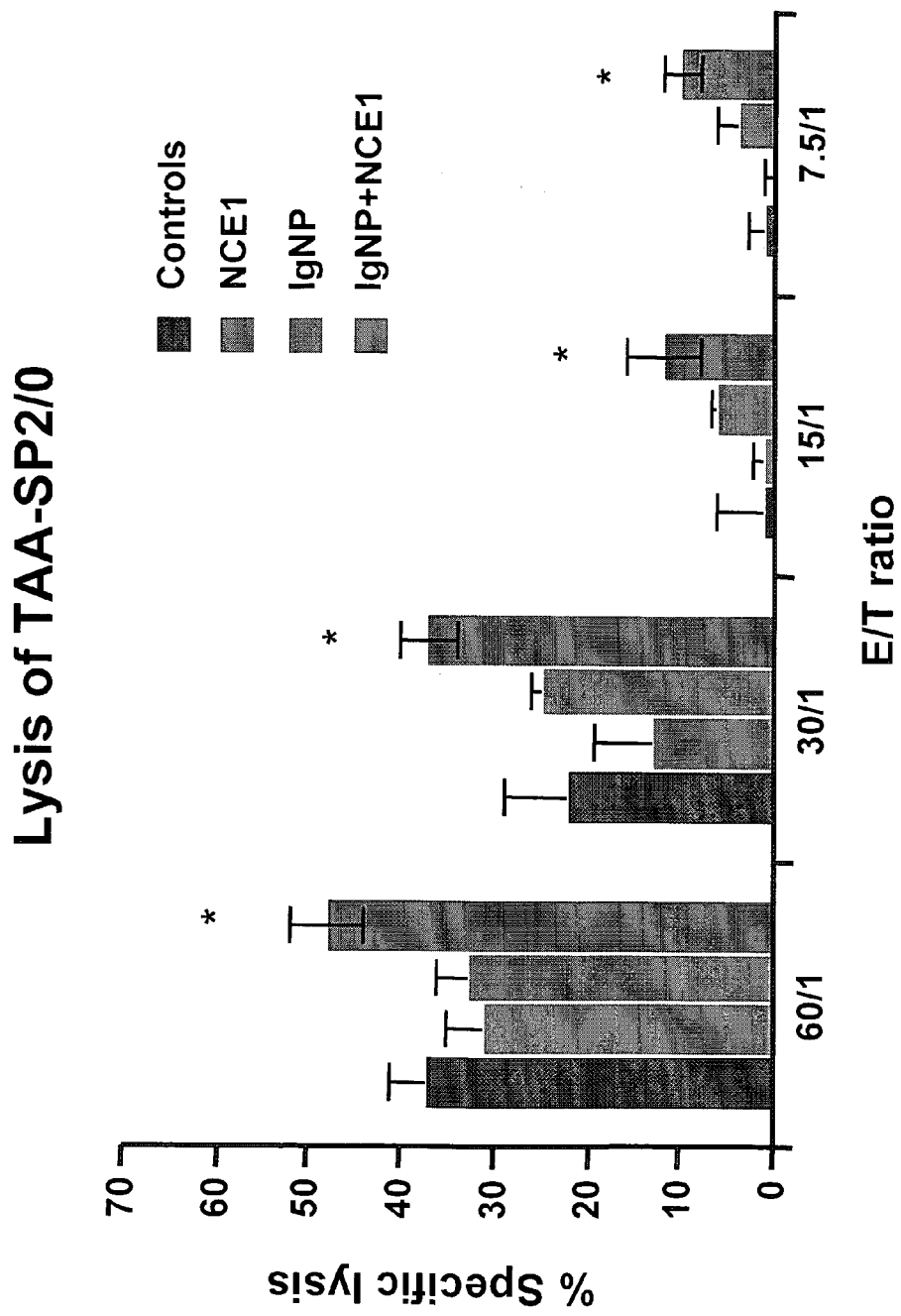
FIG. 37 shows that effective priming of anti-viral cytotoxic T cells requires both effective in vivo loading of APC with class I restricted epitope delivered via IgG, together with appropriate instruction by selected synthetic RNA motif.

The results in FIG. 37 show that effective priming of antiviral cytotoxic T cells requires both effective in vivo loading of APC with class. I restricted epitope delivered via IgG, together with appropriate instruction by selected synthetic RNA motif, namely pA:pU.

EXAMPLE 37

Shows that vaccination with an IgG bearing a viral MHC class I-restricted epitope, together with selected synthetic RNA motif, provided protection against infectious challenge with a prototype virus.

BALB/c mice were immunized with 50 ug of recIgG-NP (Kd) together with 50 ug of selected synthetic RNA (pA: pU), by subcutaneous injection. Three weeks after immunization, the mice were challenged with $10^4$ TCID 50 of infectious WSN influenza virus and sacrificed 5 days later. The pulmonary virus was titrated in lung homogenates by standard MDCK hemagglutination assay as follows: on day one MDCK cells were plated in 96 well plates at $2\times10^4$/well/200 ul and incubated for 24 hours at 37° C., 5$CO_2$. The next day, 25 µl of the 10 fold dilutions in DMEM media of the lung homogenates were incubates in briefly tripsinized MDCK plates (1 minute) in triplicates and incubated at 37° C. After one hour, 175 ul of the DMEM complete media was added and plates were incubated for 48 hours at 37° C., 5% $CO_2$. After two days, the hemagglutination-inhibition was done with chicken red blood cells incubated with the cell culture supernatants from the MDCK plate for 30 minutes at room temperature and the results were expressed as means±SEM'of total pulmonary virus (n=4 mice/group). As a control, non-immunized mice were used.

Figure 38:
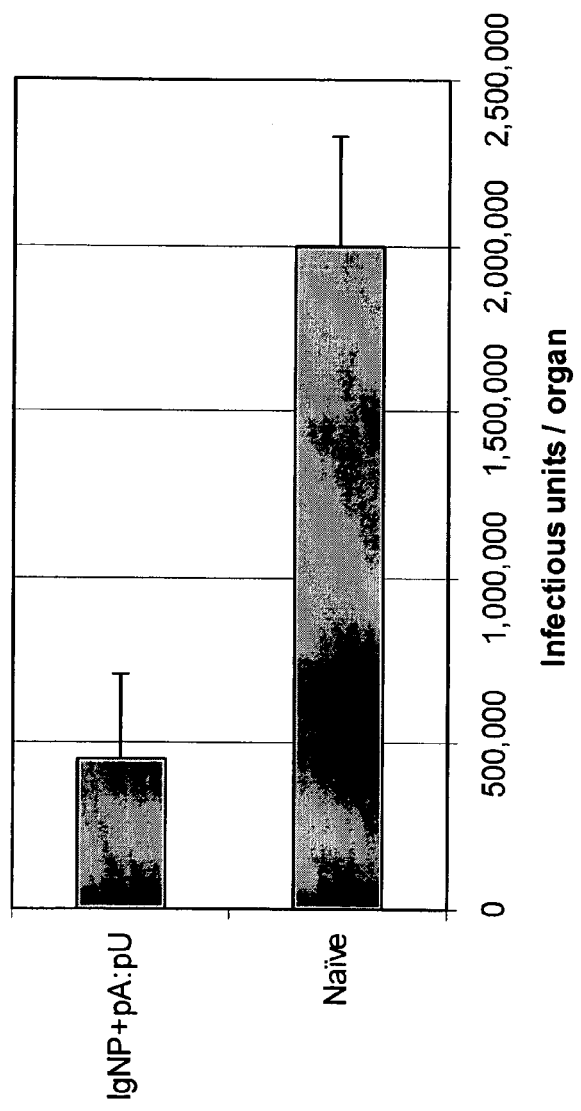
FIG. 38 shows that immunization with a recombinant IgG bearing a viral class I restricted epitope together with selected synthetic dsRNA, resulted in priming of an immune response capable of limiting the replication of a virus subsequent to infectious challenge.

The results in FIG. 38 show that immunization with a recombinant IgG bearing a viral class I restricted epitope together with selected synthetic dsRNA (pA:pU) resulted in priming of an immune response capable to limit the replication of a virus subsequent to infectious challenge.

EXAMPLE 38

Figure 39:
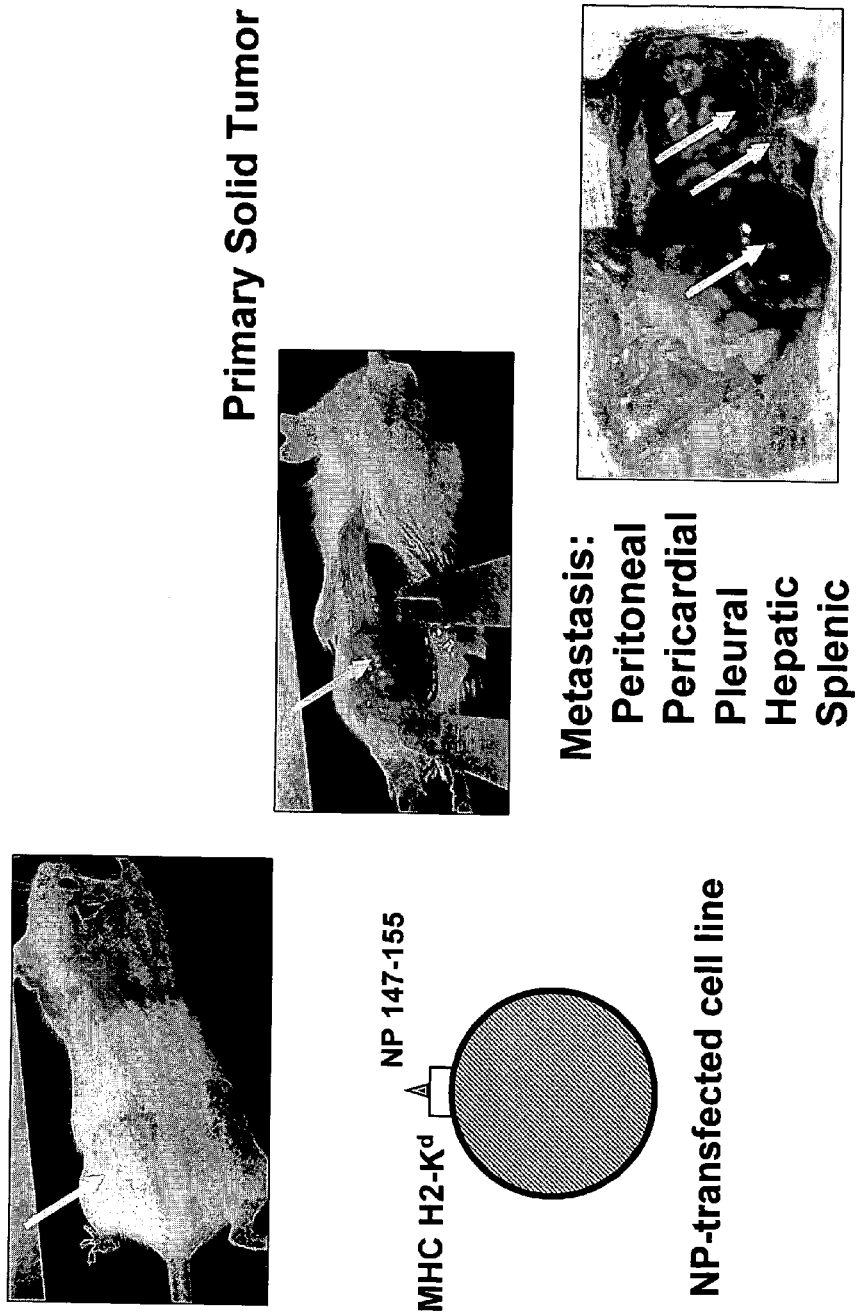
FIG. 39 describes the tumor models used for testing the efficiency of Ig-peptide-based molecules.

FIG. 39 describes the tumor models used for testing the efficiency of a Ig-peptide-based molecules.

Balb-c mice ($K^d$ restricted) have been used to establish a tumor model. Tumor cells (1 to 15 million in 100 µL) were typically injected in the flank to the mouse (see arrow in upper photo in FIG. 39). Primary tumors (i.e. those at the sight of injection) were first detected by palpating the area and then quantitated by measuring the tumor size with a caliper (see FIG. 39). In one series of experiments, the mouse myeloma cell line (SP2/0), either untransfected cells or cells stable transfected expressing heterologous protein (recombinant IgG expressing different epitope peptides in the CDR3 region of the heavy chain or the complete NP protein), was used to induce tumors in the mice. Expression of heterologous proteins in the SP2/0 cells provided specific tumor associated antigens (TAA) for testing various anti-tumor strategies in the immunocompetent mice. Typically, untreated mice developed palpable solid primary tumors 1 week post injection that led to morbidity and death over the next 4 weeks. Postmortem examination of the injected mice revealed metastatic lesions (see FIG. 39). Sp2/0 cells were cultured from primary tumor tissue as well as spleen taken from tumor-bearing mice (data not shown). SP2/0 cells were stably transfected with a recombinant IgG-expressing plasmids that were all identical except for the specific epitope sequence introduced into the CDR3 region of the heavy chain, for example, the MHC I restricted NP epitope (amino acids 147-155, see FIG. 39). SP2/0 cells were also stably transfected with a plasmid containing the coding sequence for the entire NP protein of WSN virus under control of the CMV promoter. All transfected cell lines produced primary tumors over the same frame as wild type SP2/0 cells.

This tumor model was extended to include an adenocarcinoma cell line (4T1, ATCC CRL-2539, $K^d$ restricted), previously shown to induce metastatic tumors in Balb-c mice. The 4T-1 cell line was similar to that described above for the SP/0 line. Injection of 1 to 15 million 4T-1 cells into the flank of Balb-c mice produced a palpable primary tumor over a time frame similar to injections of SP2/0 cells eventually leading to death. Postmortem collection of tissue from various organs showed that 4T-1 could be recovered from spleen, lungs as well as the primary tumor (not shown). 4T-1 cells were stably transfected with a NP-expressing plasmid described above. As with SP2/0 cells, transfection of the 4T-1 cell did not affect the course of tumor growth and lethality of disease.

EXAMPLE 39

Demonstrates successful control and treatment of a tumor after clinical diagnosis, by using a tumor associate T cell epitope within a recombinant IgG together with a selected co-stimulatory RNA motif.

Balb/c mice were injected with SP2/0 cells (15 million in 100 µL) stably expressing recombinant IgG carrying the MHC I (Kd) NP epitope peptide in the CDR3 region of the heavy chain (IgNP). At day 7 post injection all mice had palpable tumors and the mice were randomized into 3 groups:

co-stimulatory motif (i.e. dsRNA comprised of polymeric pApU) alone; purified IgTAA protein (IgNP); and both dsRNA pA:pU and purified IgTAA protein. The time of treatment is indicated by the arrows in FIG. 40, and each injection contained 50 µg of the indicated compound. The mice that developed metastatic disease and died are represented with a "D" in the figure.

The data show that the combination of dsRNA (co-stimulatory motif) and IgTAA (IgNP) produced a dramatic protective response in mice that all had primary tumors at the start of therapy. While all mice treated with either the dsRNA or IgTAA compound alone succumbed to disease, 100% of the mice treated with both were still alive 3 weeks after initiation of treatment and were in good clinical condition at the time of sacrifice for measurement of T cell response. These data show that in vivo loading of APC with TAA (accomplished by uptake of IgNP via the Fc receptor of APC) is not sufficient for a potent anti-tumor response. The tumor rejection and survival displayed by, mice treated with IgNP in combination with pApU dsRNA highlights the important role co-stimulation plays in treatment of tumors with tumor-associated antigens.

Figure 40:
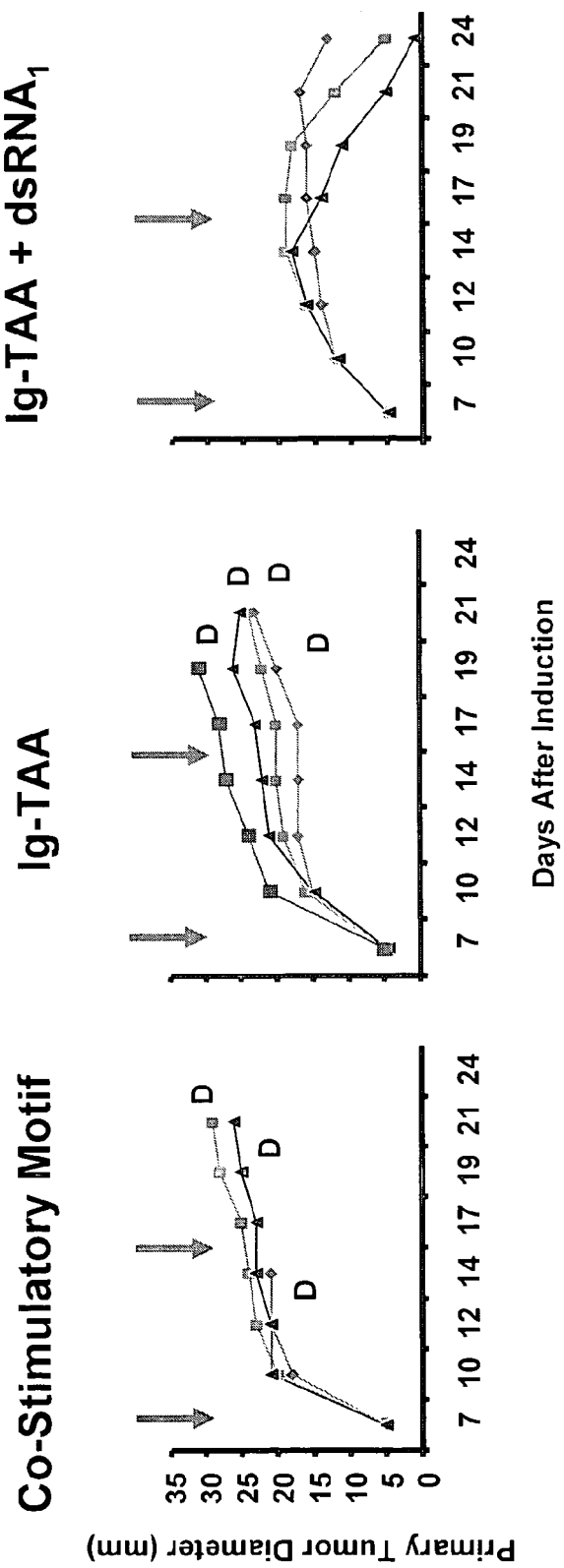
FIG. 40 shows that both effective in vivo loading of APC with tumor associated antigen, together with simultaneous activation by selected synthetic RNA motifs, are necessary and sufficient for effective control of tumor growth and induction of tumor rejection.

In conclusion, the results in FIG. 40 show that both effective in vivo loading of APC with tumor associated antigen, together with simultaneous activation by selected synthetic RNA motifs, are necessary and sufficient for effective control of tumor growth and induction of tumor rejection.

EXAMPLE 40

This Example, in context of sublethal inoculation of tumor cells, shows that the suboptimal response to tumor antigens could be corrected by therapy with peptide epitope within an IgG backbone, together with co-stimulatory motif.

Balb/c mice were injected with SP2/0 cells stably expressing recombinant IgG (IgNP) that contains the MHC I ($K^d$) epitope (amino acids 147-155) of WSN virus nucleoprotein in the CDR3 of the heavy chain. The cell inoculum was 1 million cells (in 100 µL) per mouse. The mice were observed until such time as palpable tumors were detected at the site of injection. At this point the tumors were measured and 8 mice were left untreated (control) while 6 were injected intratumorally with purified IgTAA (i.e. purified IgNP, 2 mg/kg) and dsRNA (pApU, 4 mg/kg) weekly. Weekly measurements of the tumors were taken.

Figures 41A, 41B:
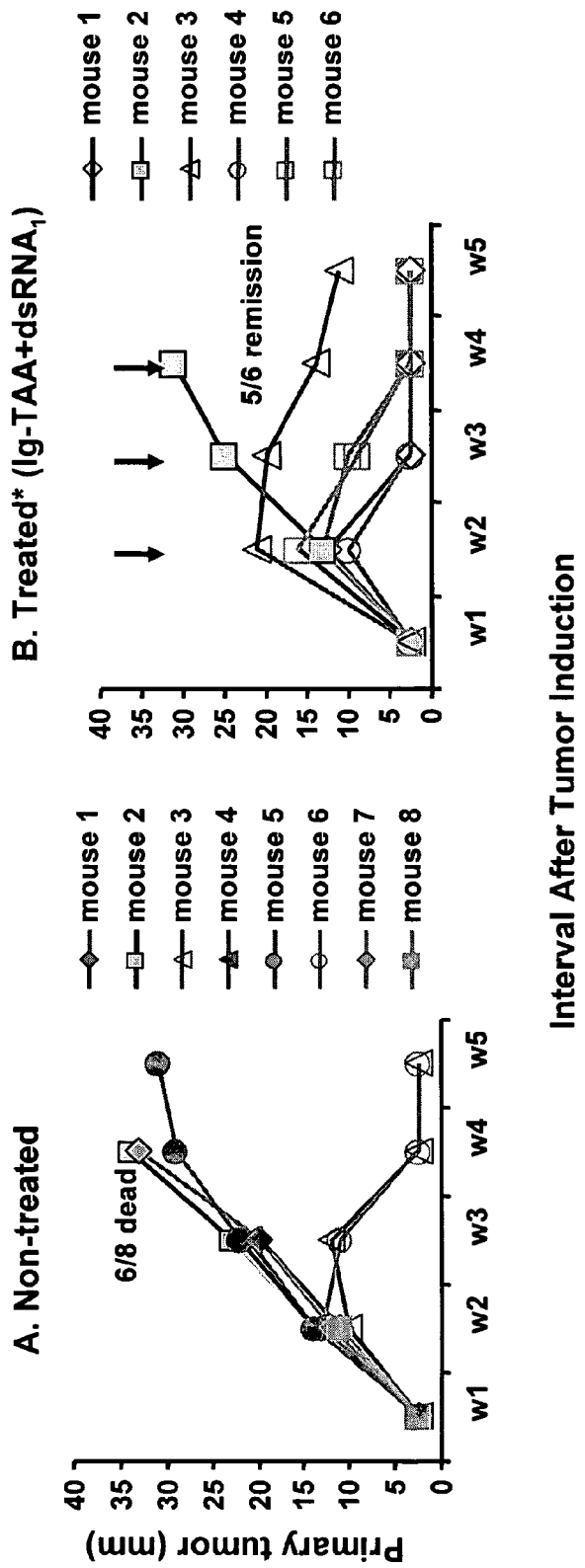
FIG. 41 shows that both effective in vivo loading of APC with tumor associated antigen, together with simultaneous activation by selected synthetic RNA, can trigger an effective immune response to tumor-associated antigens.

Panel A of FIG. 41 shows that in 6 of 8 of the control mice the induced tumor was progressive and ultimately lethal whereas 2 of the mice completely rejected the tumor spontaneously. Panel B of FIG. 41 shows that the 3 weekly treatments with IgNP/dsRNA (indicated by the arrows) stimulated complete tumor rejection in 4 of the 6 mice and significant remission in another.

The results in FIG. 41 shows that both effective in vivo loading of APC with tumor associated antigen, together with simultaneous activation by selected synthetic RNA, can trigger an effective immune response to tumor-associated antigens.

EXAMPLE 41

Shows that therapy of tumor-bearing mice with a tumor epitope within an IgG backbone together with co-stimulatory synthetic dsRNA results in the restoration of the activatory status of tumor infiltrating lymphocytes.

Two BALB/c mice were injected with 10 million sp20 transfectoma expressing the NP-$K^d$ epitope. After tumors developed, one mouse was injected intratumorally with 50 µg of selected dsRNA motif (pApU) plus 50 µg of "IgNP"— recIgG-NP(10 in saline. The mice were sacrificed 24 hours later, tumors excised, digested with collagenase, filtered through 70 um filter and viable cells isolated on Ficoll gradient. Cells were stained with mAbs against TCRβ, CD25 or isotype control and assessed by FACS analysis. The results were expressed as histograms, with percentage stained cells indicated.

Materials:
1. SP20 cell line (ATCC);
BALB/c mice (Harland Sprague Dawley);
2. Falcon 70 micron filter(Becton Dickinson, cat #352350);
3. Collagenase (Sigma, cat #C-9891);
4. BSA, fraction V (Sigma, cat #A-4503);
5. Collagenase buffer: 0.225 gm BSA +0.00625 gm in 50 ml RPMI;
6. Ficoll-hypaque (1.077, Amersham, cat #17-1440-02);
7. FACS Buffer:1% fetal calf serum+0.1% azide in PBS;
8. Antibodies: All from BD Pharmingen; and,
9. Flow Cytometer: FACSCalibur (Becton Dickinson).

Method: Tumor Cell Isolation and FACS Analysis:
1. Tumor was induced as stated above 6 weeks prior;
2. Tumor was isolated from BALB/c mouse;
3. Tumor was minced with sterile scissors and 10 ml of collagenase buffer added;
4. Incubate 40 minutes, 37° C.;
5. Force tumor through a 70 µm Falcon filler with a 3 ml syringe plunger into a 50 ml tube while washing with RPMI;
6. Wash 1× and resuspend in 4 mls warm RPMI buffer;
7. With equal volume of cell suspension layered over Ficoll, centrifuge at RT, 2000 RPM, for 15 minutes;
8. Isolate layer and wash once in HL-1 buffer and resuspend in FACS buffer to $2 \times 10^6$/ml and run flow cytometry analysis;
9. Remaining cells were used for ELISPOT analysis;
10. Cells were placed in 12×75mm tubes, 50 µl/tube and stained with FITC labeled anti-mouse antibody, 2 µg/tube plus 1 µl/tube mouse serum:
Isotypic Control;
Anti -CD40;
Anti -CD8;
Anti -CD4;
Anti -CD25;
Anti -TCR gamma delta;
Anti -TCR Beta;
11. Incubate 30 minutes on ice; and,
12. Wash once with FACS buffer and resuspend in 300 µl FACS buffer.

Figure 42:
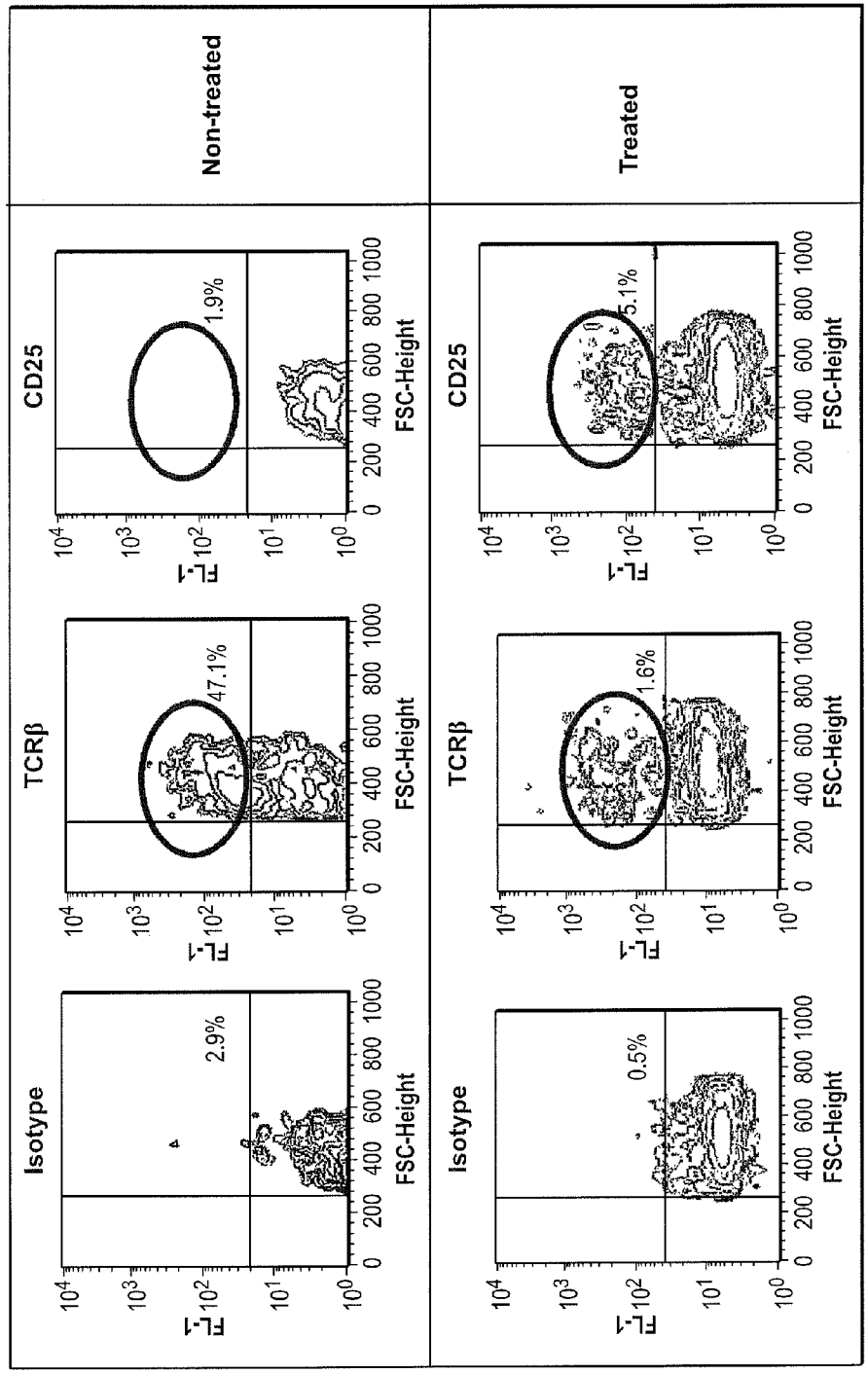
FIG. 42 shows that tumor infiltrating lymphocytes displaying the T cell receptor marker TCRβ acquired expression of the activation marker CD25 upon treatment with recombinant immunoglobulin bearing tumor associated epitope, together with selected synthetic dsRNA motif.

The results in FIG. 42 show that tumor infiltrating lymphocytes displaying the T cell receptor marker TCRβ acquired expression of the activation marker CD25 upon treatment with recombinant immunoglobulin bearing tumor associated epitope, together with selected synthetic dsRNA motif.

EXAMPLE 42

Shows that successful therapy of tumor bearing mice with a peptide epitope within the IgG backbone together with a selected co-stimulatory molecule is associated with a specific differentiation pattern of Tc, comprising Tc1 in addition to Tc2.

Mice that successfully rejected the tumor following treatment with recombinant Ig carrying a tumor associated epitope together with selected synthetic dsRNA motif as explained in Example 40, were sacrificed and the T cell response against tumor associated epitope measured by ELISPOT analysis. The ELISPOT plates (Millipore, Molsheim, France) were incubated with purified anti-cytokine Abs (4 ug/mg for anti-IL2 and anti-IL4, and 8 µg/ml for anti-IFN gamma, from BD Pharmingen) in sterile PBS (50 µl/well) at 4° C. overnight. The next day, the plates were washed 2 times with DMEM media and blocked with 200 µl/well of DMEM complete containing FBS, for an hour at 37° C.

Single cell suspension was made from the spleens, red blood cells were lysed, cells washed, counted and incubated at 5×10$^5$/well together with various concentrations of NP peptide. Plates were incubated 72 hours at 37° C., 5% CO2. After 3 days, plates were washed 5 times with PBS—tween 20 0.05% (washing buffer), and incubated with 100 µl/well of biotinylated anti-cytokine Abs, 2 µg/ml in PBS—tween 20 0.05%—FBS 0.1% (ELISPOT buffer) overnight at 4° C. The next day the plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. Plates were then allowed to dry at room temperature for 24 hours.

The data were acquired using an automated system (Navitar, Rochester, N.Y.) with ImagePro-Plus) software (Media Cybernetics, Silver Spring, Md.). The results were expressed as number (mean±SEM) of spot forming colonies corresponding to IL-4, IL-2 and IFN-γ. As a control, non-treated mice were used, which failed to reject tumor (n=4/group).

Figure 43:
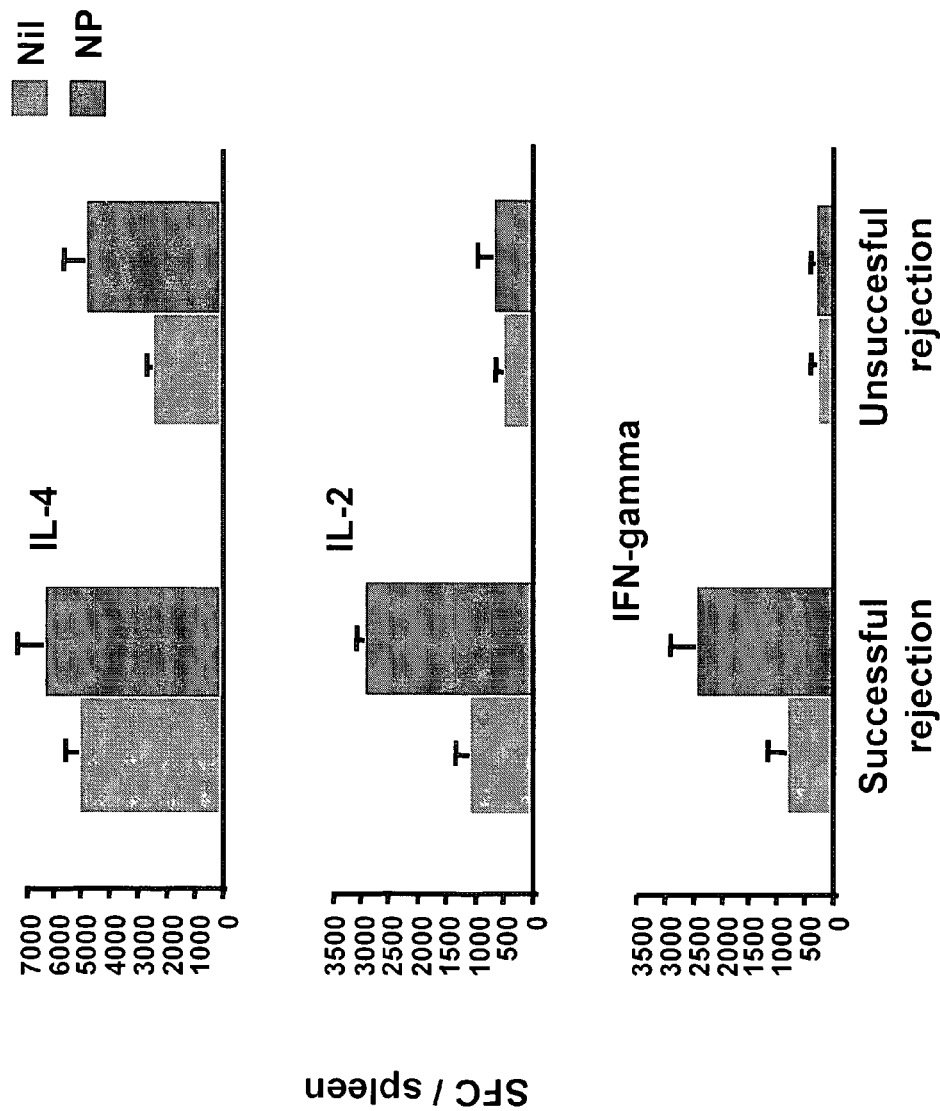
FIG. 43 shows that the treated mice that successfully rejected the tumor developed Tc1 responses against the tumor-associated epitopeon the therapeutic Ig, along with Tc2 immunity.

The results in FIG. 43 show that the treated mice that successfully rejected the tumor, developed Tc1 responses against the tumor associated epitope on the therapeutic Ig, along with Tc2 immunity. In contrast, the mice that failed to reject the tumor developed only Tc2 immunity.

EXAMPLE 43

Shows induction of effective memory response subsequent to specific treatment of tumor bearing mice with a T cell epitope within the IgG backbone, together with a selected co-stimulatory motif.

Mice bearing sp2/0 tumors expressing the NP-K$^d$ TAA were treated as described in the Example 40, by injection with recombinant Ig bearing TAA together with selected synthetic RNA motifs. After tumor rejection, the mice were challenged by subcutaneous injection administered contralaterally, with 15 million SP2/0 cells expressing NP-Kd epitope. In parallel, 4 control naïve mice were similarly injected with a tumorigenic/lethal dose of same type of cells. The development and size of the tumors was monitored and represented as diameter (mm) versus time since challenge.

Figure 44:
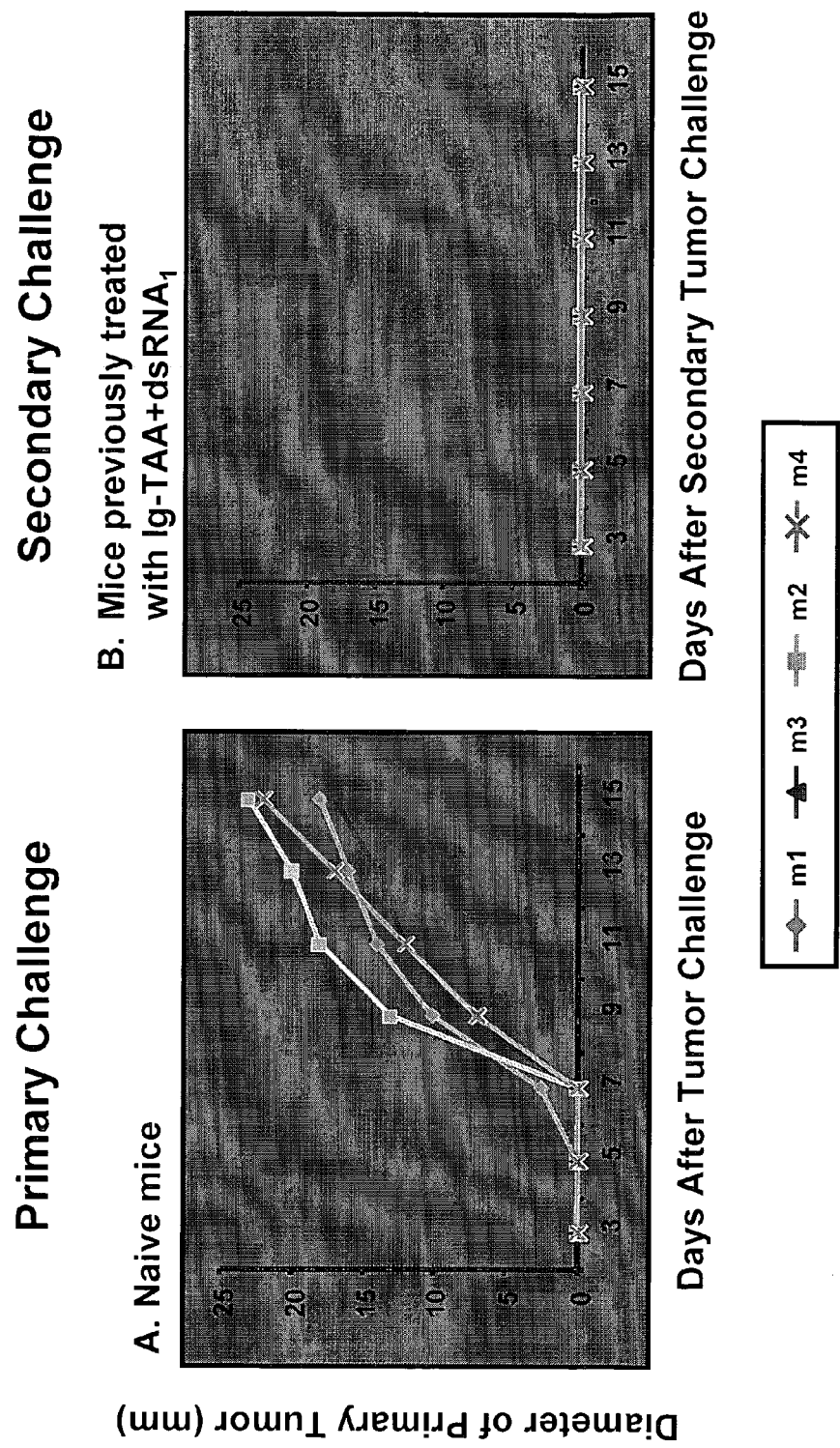
FIG. 44 shows that successful rejection of tumor induced by indicated treatment is followed by effective protection against subsequent challenge with the same tumor, indicating development of effective immune memory; and, FIGS. 45A-45B show that the emerging immunity, subsequent to the indicated treatment that results in tumor rejection, protects against challenge with loss of antigen variants and is associated with overall expansion of cytokine producing cells.

The results in FIG. 44 show that successful rejection of the tumor induced by indicated treatment is followed by effective protection against subsequent challenge with the same tumor, indicating development of effective immune memory.

EXAMPLE 44

Shows that surprisingly, the induction of tumor rejection by an IgG bearing a TAA together with a costimulator dsRNA motif, results in cross-protection against a range of tumor cell variants lacking the TAA or displaying variants of TAA.

The mice protected against homologous challenge as described in Example 43, were subjected to sequential challenge with 15 million tumor cells representing the same tumor cells devoid of TAA (loss of antigen mutants) or bearing variants of TAA lacking the NP-K$^d$ epitope. In addition, mice were challenged with a different type of tumor cell line (4T-1 adenocarcinoma) as a control, displayed in the table attached to FIG. 45A. In every case, naïve controls were included.

The status of T cell immunity of mice protected against multiple challenges with tumor variants, has been assessed by ELISPOT analysis using splenic cell suspensions stimulated with TAA (NP-Kd peptide), HA (MHC class II-restricted peptide), or protein extracts from cell lysates. The ELISPOT plates (Millipore, Molsheim, France) were incubated with purified anti-cytokine Abs (4 ug/ml for anti-IL2 and anti-IL4, and 8 µg/mg for anti-IFN gamma, from BD Pharmingen) in sterile PBS (50 µl/well) at 4° C. overnight. The next day, the plates were washed 2 times with DMEM media and blocked with 200 µl/well of DMEM complete containing FBS, for an hour at 37° C.

Single cell suspension was made from the spleens, red blood cells were lysed, cells washed, counted and incubated at 5×10$^5$/well together with various concentrations of antigen. Plates were incubated 72 hours at 37° C., 5% CO2. After 3 days, the plates were washed 5 times with PBS—tween 20 0.05% (washing buffer) and incubated with 100 µl/well of biotinylated anti-cytokine Abs, 2 µg/ml in PBS—tween 20 0.05%—FBS 0.1% (ELISPOT buffer) overnight at 4° C. The next day the plates were washed five times with washing buffer, and incubated for an hour with 1:1000 Streptavidin-HRP diluted in ELISPOT buffer. The reaction was developed with 3-amino-9-ethylcarbazole substrate (Sigma, St. Luis, Mo.) and stopped by washing the plate twice with tap water. The plates were then allowed to dry at room temperature for 24 hours.

The data were acquired using an automated system (Navitar, Rochester, N.Y.) with ImagePro-Plus) software (Media Cybernetics, Silver Spring, Md.). The results were expressed as number (mean±SEM) of spot forming colonies corresponding to IL-4, IL-2 and IFN-γ. As a control, non-treated mice that failed to reject tumor (n=4/group) were used. As a control, naïve mice were included. The data are expressed as number (mean±SEM) of cytokine producing cells/organ (n=3/group).

Figure 45B:
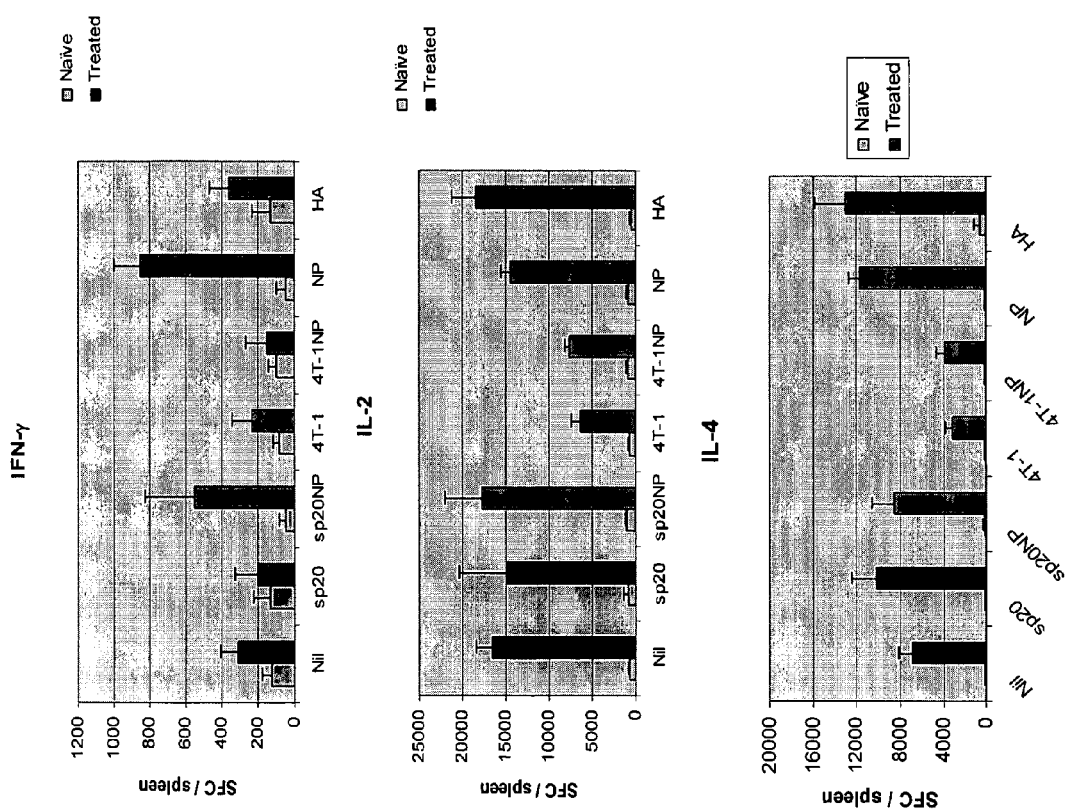

The results in FIG. 45A-45B (including the table in FIG. 45 A) show that the emerging immunity, subsequent to the indicated treatment that results in tumor rejection, protects against challenge with loss of antigen variants and is associated with overall expansion of cytokine producing cells. This indicates a broadening of the repertoire of anti-tumor lymphocytes, promoted by the proposed regimen, to tumor associated antigens that are not borne by the immunotherapeutic molecule.

We claim:

1. A method of generating an enhanced T cell response to an antigen in a patient, the method comprising, administering to the patient:

a) a polypeptide comprising at least one MHC-class I restricted T cell epitope, and;

b) a double stranded RNA having a molecular weight from 10 to 50 Kd;

wherein the double-stranded RNA is pA:pU, and wherein said polypeptide and said double-stranded RNA are administered in an amount sufficient to generate a Tc1 response in the patient to the antigen.

2. The method of claim 1, wherein the polypeptide comprises at least one MHC-class I restricted influenza NP T cell epitope covalently attached to an IgG backbone without modification of the Fc portion.

3. The method of claim 2, wherein the MHC-class I restricted T cell epitope of the antigen is covalently attached within the Complementarity Determining Region (CDR) of the IgG.

4. The method of claim 1, wherein the pA:pU is provided in an amount sufficient to induce MHC class I-restricted Tc1 cells thereby producing IFN-y.

5. The method of claim 2, wherein the immunoglobulin backbone of the IgG is derived from human IgG, or is a humanized IgG.

6. The method of claim 1, wherein the patient is human.

7. The method of claim 1, wherein the antigen is a virus.

8. The method of claim 7, wherein the virus is influenza virus.

9. The method of claim 1, wherein the T cell epitope is selected from: influenza virus MI or M2; hepatitis C virus NS3; hepatitis B virus core antigen; human papilloma virus HPV 18-E7, HPV 16-E7, HPV 18-E6, HPV 16-E6; HIV-I: reverse transcriptase; HIV-I: gag; herpes simplex antigens; and respiratory syncytial virus antigens.

10. The method of claim 1, wherein the T-cell epitope is a tumor associated T cell epitope.

11. The method of claim 1, wherein the T cell epitope is selected from:
melanoma-gp100; MART-1; TRP-2; carcinoembryonic antigen precursor; Her-2; prostate tumor antigens; carcinoembryonic antigen precursor XP064845/NCB1; MUC 1; and mucin 1.

12. The method of claim 1, wherein the polypeptide and double-stranded RNA are admixed together.

13. The method of claim 1, wherein the polypeptide and double-stranded RNA are administered separately.

* * * * *

SEQUENCE LISTING

<160> NUMBER OF SEQ ID NOS: 53

<210> SEQ ID NO 1
<211> LENGTH: 107
<212> TYPE: PRT
<213> ORGANISM: Homo sapiens -continued

<400> SEQUENCE: 1

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 2
<211> LENGTH: 110
<212> TYPE: PRT
<213> ORGANISM: Homo sapiens

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Phe Asn Lys
                85                  90                  95

Ala Leu Pro Ala Pro Ile Glu Lys Thr Ile Ser Lys Ala Lys
            100                 105                 110

<210> SEQ ID NO 3
<211> LENGTH: 15
<212> TYPE: PRT
<213> ORGANISM: Homo sapiens

<400> SEQUENCE: 3

Glu Pro Lys Ser Cys Asp Lys Thr His Thr Cys Pro Pro Cys Pro
1               5                   10                  15

<210> SEQ ID NO 4
<211> LENGTH: 5
<212> TYPE: PRT
<213> ORGANISM: Homo sapiens

<400> SEQUENCE: 4

Gln Val Gln Leu Gln
1               5

<210> SEQ ID NO 5
<211> LENGTH: 11
<212> TYPE: PRT

```
<213> ORGANISM: Influenza A virus

<400> SEQUENCE: 5

Ser Phe Glu Arg Phe Glu Ile Phe Pro Lys Glu
1               5                   10

<210> SEQ ID NO 6
<211> LENGTH: 9
<212> TYPE: PRT
<213> ORGANISM: Unknown
<220> FEATURE:
<223> OTHER INFORMATION: Description of Unknown: MHC class
      I-restricted peptide

<400> SEQUENCE: 6

Thr Tyr Thr Gln Thr Arg Ala Leu Val
1               5

<210> SEQ ID NO 7
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Gly Gly Gly Gly Glu Pro Lys Ser Cys Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Phe Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 8
```

<211> LENGTH: 566
<212> TYPE: PRT
<213> ORGANISM: Influenza A virus

<400> SEQUENCE: 8

```
Met Lys Ala Asn Leu Leu Val Leu Cys Ala Leu Ala Ala Ala Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
    130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Glu Lys Glu Gly Ser Tyr Pro
                165                 170                 175

Lys Leu Lys Asn Ser Tyr Val Asn Lys Lys Gly Lys Glu Val Leu Val
                180                 185                 190

Leu Trp Gly Ile His His Pro Ser Asn Ser Lys Asp Gln Gln Asn Ile
            195                 200                 205

Tyr Gln Asn Glu Asn Ala Tyr Val Ser Val Val Thr Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Lys Pro Gly Asp Thr
                245                 250                 255

Ile Ile Phe Glu Ala Asn Gly Asn Leu Ile Ala Pro Arg Tyr Ala Phe
                260                 265                 270

Ala Leu Ser Arg Gly Phe Gly Ser Gly Ile Ile Thr Ser Asn Ala Ser
            275                 280                 285

Met His Glu Cys Asn Thr Lys Cys Gln Thr Pro Leu Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
```

```
                385                 390                 395                 400
        Glu Lys Met Asn Ile Gln Phe Thr Ala Val Gly Lys Glu Phe Asn Lys
                        405                 410                 415

Leu Glu Lys Arg Met Glu Asn Leu Asn Lys Lys Val Asp Asp Gly Phe
                    420                 425                 430

Leu Asp Ile Trp Thr Tyr Asn Ala Glu Leu Leu Val Leu Leu Glu Asn
                    435                 440                 445

Glu Arg Thr Leu Asp Phe His Asp Ser Asn Val Lys Asn Leu Tyr Glu
                    450                 455                 460

Lys Val Lys Ser Gln Leu Lys Asn Asn Ala Lys Glu Ile Gly Asn Gly
        465                 470                 475                 480

Cys Phe Glu Phe Tyr His Lys Cys Asp Asn Glu Cys Met Glu Ser Val
                        485                 490                 495

Arg Asn Gly Thr Tyr Asp Tyr Pro Lys Tyr Ser Glu Glu Ser Lys Leu
                    500                 505                 510

Asn Arg Glu Lys Val Asp Gly Val Lys Leu Glu Ser Met Gly Ile Tyr
                    515                 520                 525

Gln Ile Leu Ala Ile Tyr Ser Thr Val Ala Ser Ser Leu Val Leu Leu
                    530                 535                 540

Val Ser Leu Gly Ala Ile Ser Phe Trp Met Cys Ser Asn Gly Ser Leu
        545                 550                 555                 560

Gln Cys Arg Ile Cys Ile
                    565

<210> SEQ ID NO 9
<211> LENGTH: 498
<212> TYPE: PRT
<213> ORGANISM: Influenza A virus

<400> SEQUENCE: 9

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
                20                  25                  30

Val Gly Gly Ile Gly Arg Phe Tyr Ile Gln Met Cys Thr Glu Leu Gln
            35                  40                  45

Leu Ser Asp Tyr Glu Gly Arg Leu Ile Gln Asn Ser Ile Thr Ile Glu
        50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Lys Arg Asp Gly Lys Trp Met Arg Glu Leu Ile Leu Tyr Asp
            100                 105                 110

Lys Asp Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190
```

```
Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ile Tyr Gly Leu Val Val Ala Ser Gly
            275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Val His Lys Ser Gln Leu Ile Trp Met Ala Cys His Ser Ala
                325                 330                 335

Ala Phe Glu Asp Leu Arg Val Ser Ser Phe Ile Arg Gly Thr Lys Val
            340                 345                 350

Val Pro Arg Gly Gln Leu Thr Thr Arg Gly Val Gln Ile Ala Ser Asn
            355                 360                 365

Glu Asn Met Glu Thr Met Asp Ser Ile Thr Leu Glu Leu Arg Ser Lys
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Asn Glu Gly Arg Thr Ser Asp Met Arg Thr Glu Ile Ile Arg Met Met
            435                 440                 445

Glu Ser Ala Arg Pro Asp Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 10
<211> LENGTH: 114
<212> TYPE: PRT
<213> ORGANISM: Mus sp.

<400> SEQUENCE: 10

Glu Val Gln Leu Gln Gln Ser Gly Ala Glu Leu Val Lys Ala Gly Ser
1               5                   10                  15

Ser Val Lys Met Ser Cys Lys Ala Thr Gly Tyr Thr Phe Ser Ser Tyr
            20                  25                  30

Glu Leu Tyr Trp Val Arg Gln Ala Pro Gly Gln Gly Leu Glu Asp Leu
        35                  40                  45

Gly Tyr Ile Ser Ser Ser Ser Ala Tyr Pro Asn Tyr Ala Gln Lys Phe
    50                  55                  60
```

```
Gln Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Phe Cys
                 85                  90                  95

Ala Val Arg Val Ile Ser Arg Tyr Phe Asp Gly Trp Gly Gln Gly Thr
                100                 105                 110

Leu Val

<210> SEQ ID NO 11
<211> LENGTH: 252
<212> TYPE: PRT
<213> ORGANISM: Influenza A virus

<400> SEQUENCE: 11

Met Ser Leu Leu Thr Glu Val Glu Thr Tyr Val Leu Ser Ile Ile Pro
 1               5                  10                  15

Ser Gly Pro Leu Lys Ala Glu Ile Ala Gln Arg Leu Glu Asp Val Phe
                20                  25                  30

Ala Gly Lys Asn Thr Asp Leu Glu Val Leu Met Glu Trp Leu Lys Thr
             35                  40                  45

Arg Pro Ile Leu Ser Pro Leu Thr Lys Gly Val Leu Gly Phe Val Phe
 50                  55                  60

Thr Leu Thr Val Pro Ser Glu Arg Gly Leu Gln Arg Arg Arg Phe Val
 65                  70                  75                  80

Gln Asn Ala Leu Asn Gly Asn Gly Asp Pro Asn Asn Met Asp Lys Ala
                 85                  90                  95

Val Lys Leu Tyr Arg Lys Leu Lys Arg Glu Ile Thr Phe Tyr Gly Ala
                100                 105                 110

Lys Glu Val Ala Leu Ser Tyr Ser Thr Gly Ala Leu Ala Ser Cys Met
            115                 120                 125

Gly Leu Ile Tyr Asn Arg Met Gly Thr Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
                180                 185                 190

Ala Gly Ser Ser Glu Gln Ala Ala Glu Ala Met Glu Val Ala Ser Gln
            195                 200                 205

Ala Arg Gln Met Val Gln Ala Met Arg Thr Val Gly Thr His Pro Ser
        210                 215                 220

Ser Ser Ala Gly Leu Lys Asp Asp Leu Leu Glu Asn Leu Gln Ala Tyr
225                 230                 235                 240

Gln Lys Arg Met Gly Val Gln Leu Gln Arg Phe Lys
                245                 250

<210> SEQ ID NO 12
<211> LENGTH: 97
<212> TYPE: PRT
<213> ORGANISM: Influenza A virus

<400> SEQUENCE: 12

Met Ser Leu Leu Thr Glu Val Glu Thr Pro Thr Arg Asn Gly Trp Glu
 1               5                  10                  15

Cys Ser Cys Ser Asp Ser Ser Asp Pro Leu Val Ile Ala Ala Ser Ile
```

```
            20                  25                  30

Ile Gly Ile Leu His Phe Ile Leu Trp Ile Leu Asp Arg Leu Phe Phe
             35                  40                  45

Lys Cys Ile Tyr Arg Arg Leu Lys Tyr Gly Leu Lys Arg Gly Pro Ser
 50                  55                  60

Thr Glu Gly Val Pro Lys Ser Met Arg Glu Glu Tyr Arg Gln Glu Gln
 65                  70                  75                  80

Gln Asn Ala Val Asp Val Asp Gly His Phe Val Asn Ile Glu Leu
                 85                  90                  95

Glu

<210> SEQ ID NO 13
<211> LENGTH: 181
<212> TYPE: PRT
<213> ORGANISM: Hepatitis C virus

<400> SEQUENCE: 13

Ala Pro Ile Thr Ala Tyr Ala Gln Gln Thr Arg Gly Leu Leu Gly Cys
 1               5                  10                  15

Ile Ile Thr Ser Leu Thr Gly Arg Asp Arg Asn Gln Val Glu Gly Glu
                 20                  25                  30

Val Gln Val Val Ser Thr Ala Thr Gln Ser Phe Leu Ala Thr Cys Ile
             35                  40                  45

Asn Gly Val Cys Trp Thr Val Phe His Gly Ala Gly Ser Lys Thr Leu
 50                  55                  60

Ala Gly Pro Lys Gly Pro Ile Thr Gln Met Tyr Thr Asn Val Asp Gln
 65                  70                  75                  80

Asp Leu Val Gly Trp Pro Ala Pro Gly Ala Arg Ser Leu Thr Pro
                 85                  90                  95

Cys Thr Cys Gly Ser Ser Asp Leu Tyr Leu Val Thr Arg His Ala Asp
             100                 105                 110

Val Val Pro Val Arg Arg Arg Ser Asp Ser Arg Gly Ser Leu Leu Ser
             115                 120                 125

Pro Arg Pro Ile Ser Tyr Leu Lys Gly Ser Ser Gly Gly Pro Leu Leu
 130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                 165                 170                 175

Thr Thr Met Arg Ser
             180

<210> SEQ ID NO 14
<211> LENGTH: 139
<212> TYPE: PRT
<213> ORGANISM: Hepatitis B virus

<400> SEQUENCE: 14

Met Asp Ile Asp Pro Tyr Lys Glu Phe Gly Ala Ser Val Glu Leu Leu
 1               5                  10                  15

Ser Phe Leu Pro Ser Asp Phe Phe Pro Ser Ile Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
 50                  55                  60
```

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Arg Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile
    130                 135

<210> SEQ ID NO 15
<211> LENGTH: 105
<212> TYPE: PRT
<213> ORGANISM: Human papillomavirus

<400> SEQUENCE: 15

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 16
<211> LENGTH: 98
<212> TYPE: PRT
<213> ORGANISM: Human papillomavirus

<400> SEQUENCE: 16

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 17
<211> LENGTH: 158
<212> TYPE: PRT
<213> ORGANISM: Human papillomavirus

<400> SEQUENCE: 17

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Lys Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155

<210> SEQ ID NO 18
<211> LENGTH: 158
<212> TYPE: PRT
<213> ORGANISM: Human papillomavirus

<400> SEQUENCE: 18

Met His Gln Lys Arg Thr Ala Met Phe Gln Asp Pro Gln Glu Arg Pro
1               5                   10                  15

Arg Lys Leu Pro His Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg Tyr Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 19
<211> LENGTH: 661
<212> TYPE: PRT
<213> ORGANISM: Homo sapiens

<400> SEQUENCE: 19

Met Asp Leu Val Leu Lys Arg Cys Leu Leu His Leu Ala Val Ile Gly

-continued

```
1               5                  10                 15
Ala Leu Leu Ala Val Gly Ala Thr Lys Val Pro Arg Asn Gln Asp Trp
                20                 25                 30
Leu Gly Val Ser Arg Gln Leu Arg Thr Lys Ala Trp Asn Arg Gln Leu
                35                 40                 45
Tyr Pro Glu Trp Thr Glu Ala Gln Arg Leu Asp Cys Trp Arg Gly Gly
                50                 55                 60
Gln Val Ser Leu Lys Val Ser Asn Asp Gly Pro Thr Leu Ile Gly Ala
65                                 70                 75                 80
Asn Ala Ser Phe Ser Ile Ala Leu Asn Phe Pro Gly Ser Gln Lys Val
                85                 90                 95
Leu Pro Asp Gly Gln Val Ile Trp Val Asn Asn Thr Ile Ile Asn Gly
                100                105                110
Ser Gln Val Trp Gly Gly Gln Pro Val Tyr Pro Gln Glu Thr Asp Asp
                115                120                125
Ala Cys Ile Phe Pro Asp Gly Gly Pro Cys Pro Ser Gly Ser Trp Ser
                130                135                140
Gln Lys Arg Ser Phe Val Tyr Val Trp Lys Thr Trp Gly Gln Tyr Trp
145                150                155                160
Gln Val Leu Gly Gly Pro Val Ser Gly Leu Ser Ile Gly Thr Gly Arg
                165                170                175
Ala Met Leu Gly Thr His Thr Met Glu Val Thr Val Tyr His Arg Arg
                180                185                190
Gly Ser Arg Ser Tyr Val Pro Leu Ala His Ser Ser Ala Phe Thr
                195                200                205
Ile Thr Asp Gln Val Pro Phe Ser Val Ser Val Ser Gln Leu Arg Ala
                210                215                220
Leu Asp Gly Gly Asn Lys His Phe Leu Arg Asn Gln Pro Leu Thr Phe
225                230                235                240
Ala Leu Gln Leu His Asp Pro Ser Gly Tyr Leu Ala Glu Ala Asp Leu
                245                250                255
Ser Tyr Thr Trp Asp Phe Gly Asp Ser Ser Gly Thr Leu Ile Ser Arg
                260                265                270
Ala Leu Val Val Thr His Thr Tyr Leu Glu Pro Gly Pro Val Thr Ala
                275                280                285
Gln Val Val Leu Gln Ala Ala Ile Pro Leu Thr Ser Cys Gly Ser Ser
                290                295                300
Pro Val Pro Gly Thr Thr Asp Gly His Arg Pro Thr Ala Glu Ala Pro
305                310                315                320
Asn Thr Thr Ala Gly Gln Val Pro Thr Thr Glu Val Val Gly Thr Thr
                325                330                335
Pro Gly Gln Ala Pro Thr Ala Glu Pro Ser Gly Thr Thr Ser Val Gln
                340                345                350
Val Pro Thr Thr Glu Val Ile Ser Thr Ala Pro Val Gln Met Pro Thr
                355                360                365
Ala Glu Ser Thr Gly Met Thr Pro Glu Lys Val Pro Val Ser Glu Val
                370                375                380
Met Gly Thr Thr Leu Ala Glu Met Ser Thr Pro Glu Ala Thr Gly Met
385                390                395                400
Thr Pro Ala Glu Val Ser Ile Val Val Leu Ser Gly Thr Thr Ala Ala
                405                410                415
Gln Val Thr Thr Thr Glu Trp Val Glu Thr Thr Ala Arg Glu Leu Pro
                420                425                430
```

```
Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
                500                 505                 510

Thr Val Ser Cys Gln Gly Gly Leu Pro Lys Glu Ala Cys Met Glu Ile
            515                 520                 525

Ser Ser Pro Gly Cys Gln Pro Pro Ala Gln Arg Leu Cys Gln Pro Val
            530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
                580                 585                 590

Leu Gly Gln Val Pro Leu Ile Val Gly Ile Leu Leu Val Leu Met Ala
            595                 600                 605

Val Val Leu Ala Ser Leu Ile Tyr Arg Arg Arg Leu Met Lys Gln Asp
            610                 615                 620

Phe Ser Val Pro Gln Leu Pro His Ser Ser His His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 20
<211> LENGTH: 118
<212> TYPE: PRT
<213> ORGANISM: Homo sapiens

<400> SEQUENCE: 20

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
            115
```

<210> SEQ ID NO 21
<211> LENGTH: 237
<212> TYPE: PRT
<213> ORGANISM: Homo sapiens

<400> SEQUENCE: 21

Met Ser Pro Leu Trp Trp Gly Phe Leu Leu Ser Cys Leu Gly Cys Lys
1               5                   10                  15

Ile Leu Pro Gly Ala Gln Gly Gln Phe Pro Arg Val Cys Met Thr Val
            20                  25                  30

Asp Ser Leu Val Asn Lys Glu Cys Cys Pro Arg Leu Gly Ala Glu Ser
        35                  40                  45

Ala Asn Val Cys Gly Ser Gln Gln Gly Arg Gly Gln Cys Thr Glu Val
    50                  55                  60

Arg Ala Asp Thr Arg Pro Trp Ser Gly Pro Tyr Ile Leu Arg Asn Gln
65                  70                  75                  80

Asp Asp Arg Glu Leu Trp Pro Arg Lys Phe Phe His Arg Thr Cys Lys
                85                  90                  95

Cys Thr Gly Asn Phe Ala Gly Tyr Asn Cys Gly Asp Cys Lys Phe Gly
            100                 105                 110

Trp Thr Gly Pro Asn Cys Glu Arg Lys Lys Pro Pro Val Ile Arg Gln
        115                 120                 125

Asn Ile His Ser Leu Ser Pro Gln Glu Arg Glu Gln Phe Leu Gly Ala
    130                 135                 140

Leu Asp Leu Ala Lys Lys Arg Val His Pro Asp Tyr Val Ile Thr Thr
145                 150                 155                 160

Gln His Trp Val Gly Leu Leu Gly Pro Asn Gly Thr Gln Pro Gln Phe
                165                 170                 175

Ala Asn Cys Ser Val Tyr Asp Phe Phe Val Trp Leu His Tyr Tyr Ser
            180                 185                 190

Val Arg Asp Thr Leu Leu Gly Gly Phe Phe Pro Trp Leu Lys Val Tyr
        195                 200                 205

Tyr Tyr Arg Phe Val Ile Gly Leu Arg Val Trp Gln Trp Glu Val Ile
    210                 215                 220

Ser Cys Lys Leu Ile Lys Arg Ala Thr Thr Arg Gln Pro
225                 230                 235

<210> SEQ ID NO 22
<211> LENGTH: 337
<212> TYPE: PRT
<213> ORGANISM: Homo sapiens

<400> SEQUENCE: 22

Met Asp Leu Ser Arg Pro Arg Trp Ser Leu Trp Arg Arg Val Phe Leu
1               5                   10                  15

Met Ala Ser Leu Leu Ala Cys Gly Ile Cys Gln Ala Ser Gly Gln Ile
            20                  25                  30

Phe Ile Thr Gln Thr Leu Gly Ile Lys Gly Tyr Arg Thr Val Val Ala
        35                  40                  45

Leu Asp Lys Val Pro Glu Asp Val Gln Glu Tyr Ser Trp Tyr Trp Gly
    50                  55                  60

Ala Asn Asp Ser Ala Gly Asn Met Ile Ile Ser His Lys Pro Pro Ser
65                  70                  75                  80

Ala Gln Gln Pro Gly Pro Met Tyr Thr Gly Arg Glu Arg Val Asn Arg
                85                  90                  95

Glu Gly Ser Leu Leu Ile Arg Pro Thr Ala Leu Asn Asp Thr Gly Asn

```
            100             105             110
Tyr Thr Val Arg Val Ala Gly Asn Glu Thr Gln Arg Ala Thr Gly
            115             120             125

Trp Leu Glu Val Leu Glu Leu Gly Ser Asn Leu Gly Ile Ser Val Asn
130             135             140

Ala Ser Ser Leu Val Glu Asn Met Asp Ser Val Ala Ala Asp Cys Leu
145             150             155             160

Thr Asn Val Thr Asn Ile Thr Trp Tyr Val Asn Asp Val Pro Thr Ser
                165             170             175

Ser Ser Asp Arg Met Thr Ile Ser Pro Asp Gly Lys Thr Leu Val Ile
                180             185             190

Leu Arg Val Ser Arg Tyr Asp Arg Thr Ile Gln Cys Met Ile Glu Ser
                195             200             205

Phe Pro Glu Ile Phe Gln Arg Ser Glu Arg Ile Ser Leu Thr Val Ala
210             215             220

Tyr Gly Pro Asp Tyr Val Leu Leu Arg Ser Asn Pro Asp Asp Phe Asn
225             230             235             240

Gly Ile Val Thr Ala Glu Ile Gly Ser Gln Val Glu Met Glu Cys Ile
                245             250             255

Cys Tyr Ser Phe Leu Asp Leu Lys Tyr His Trp Ile His Asn Gly Ser
                260             265             270

Leu Leu Asn Phe Ser Asp Ala Lys Met Asn Leu Ser Ser Leu Ala Trp
                275             280             285

Glu Gln Met Gly Arg Tyr Arg Cys Thr Val Glu Asn Pro Val Thr Gln
290             295             300

Leu Ile Met Tyr Met Asp Val Arg Ile Gln Ala Pro His Glu Cys Ser
305             310             315             320

Ser Ser Pro Pro Gly Ser Cys Phe Ala His Leu Pro Ala Ser Met Pro
                325             330             335

Cys

<210> SEQ ID NO 23
<211> LENGTH: 1255
<212> TYPE: PRT
<213> ORGANISM: Homo sapiens

<400> SEQUENCE: 23

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
```

```
                130             135             140
Leu Thr Glu Ile Leu Lys Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
                195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
                290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
                370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
                450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560
```

```
Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975
```

Ser Arg Met Ala Arg Asp Pro Gln Arg Phe Val Val Ile Gln Asn Glu
        980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 24
<211> LENGTH: 9
<212> TYPE: PRT
<213> ORGANISM: Unknown
<220> FEATURE:
<223> OTHER INFORMATION: Description of Unknown: HLA-A2 anchor
    motif peptide
<220> FEATURE:
<221> NAME/KEY: MOD_RES
<222> LOCATION: (3)..(8)
<223> OTHER INFORMATION: Any amino acid except Cys

<400> SEQUENCE: 24

Phe Leu Xaa Xaa Xaa Xaa Xaa Xaa Val
1               5

<210> SEQ ID NO 25
<211> LENGTH: 875
<212> TYPE: PRT

<213> ORGANISM: Clostridium tetani

<400> SEQUENCE: 25

```
Lys Ile Ile Pro Pro Thr Asn Ile Arg Glu Asn Leu Tyr Asn Arg Thr
1               5                   10                  15

Ala Ser Leu Thr Asp Leu Gly Gly Glu Leu Cys Ile Lys Ile Lys Asn
            20                  25                  30

Glu Asp Leu Thr Phe Ile Ala Glu Lys Asn Ser Phe Ser Glu Glu Pro
        35                  40                  45

Phe Gln Asp Glu Ile Val Ser Tyr Asn Thr Lys Asn Lys Pro Leu Asn
    50                  55                  60

Phe Asn Tyr Ser Leu Asp Lys Ile Ile Val Asp Tyr Asn Leu Gln Ser
65                  70                  75                  80

Lys Ile Thr Leu Pro Asn Asp Arg Thr Thr Pro Val Thr Lys Gly Ile
                85                  90                  95

Pro Tyr Ala Pro Glu Tyr Lys Ser Asn Ala Ala Ser Thr Ile Glu Ile
            100                 105                 110

His Asn Ile Asp Asp Asn Thr Ile Tyr Gln Tyr Leu Tyr Ala Gln Lys
        115                 120                 125

Ser Pro Thr Thr Leu Gln Arg Ile Thr Met Thr Asn Ser Val Asp Asp
    130                 135                 140

Ala Leu Ile Asn Ser Thr Lys Ile Tyr Ser Tyr Phe Pro Ser Val Ile
145                 150                 155                 160

Ser Lys Val Asn Gln Gly Ala Gln Gly Ile Leu Phe Leu Gln Trp Val
                165                 170                 175

Arg Asp Ile Ile Asp Asp Phe Thr Asn Glu Ser Ser Gln Lys Thr Thr
            180                 185                 190

Ile Asp Lys Ile Ser Asp Val Ser Thr Ile Val Pro Tyr Ile Gly Pro
        195                 200                 205

Ala Leu Asn Ile Val Lys Gln Gly Tyr Glu Gly Asn Phe Ile Gly Ala
    210                 215                 220

Leu Glu Thr Thr Gly Val Val Leu Leu Leu Glu Tyr Ile Pro Glu Ile
225                 230                 235                 240

Thr Leu Pro Val Ile Ala Ala Leu Ser Ile Ala Glu Ser Ser Thr Gln
                245                 250                 255

Lys Glu Lys Ile Ile Lys Thr Ile Asp Asn Phe Leu Glu Lys Arg Tyr
            260                 265                 270

Glu Lys Trp Ile Glu Val Tyr Lys Leu Val Lys Ala Lys Trp Leu Gly
        275                 280                 285

Thr Val Asn Thr Gln Phe Gln Lys Arg Ser Tyr Gln Met Tyr Arg Ser
    290                 295                 300

Leu Glu Tyr Gln Val Asp Ala Ile Lys Lys Ile Ile Asp Tyr Glu Tyr
305                 310                 315                 320

Lys Ile Tyr Ser Gly Pro Asp Lys Glu Gln Ile Ala Asp Glu Ile Asn
                325                 330                 335

Asn Leu Lys Asn Lys Leu Glu Glu Lys Ala Asn Lys Ala Met Ile Asn
            340                 345                 350

Ile Asn Ile Phe Met Arg Glu Ser Ser Arg Ser Phe Leu Val Asn Gln
        355                 360                 365

Met Ile Asn Glu Ala Lys Lys Gln Leu Leu Glu Phe Asp Thr Gln Ser
    370                 375                 380

Lys Asn Ile Leu Met Gln Tyr Ile Lys Ala Asn Ser Lys Phe Ile Gly
385                 390                 395                 400
```

```
Ile Thr Glu Leu Lys Lys Leu Glu Ser Lys Ile Asn Lys Val Phe Ser
                405                 410                 415

Thr Pro Ile Pro Phe Ser Tyr Ser Lys Asn Leu Asp Cys Trp Val Asp
            420                 425                 430

Asn Glu Glu Asp Ile Asp Val Ile Leu Lys Lys Ser Thr Ile Leu Asn
        435                 440                 445

Leu Asp Ile Asn Asn Asp Ile Ile Ser Asp Ile Ser Gly Phe Asn Ser
    450                 455                 460

Ser Val Ile Thr Tyr Pro Asp Ala Gln Leu Val Pro Gly Ile Asn Gly
465                 470                 475                 480

Lys Ala Ile His Leu Val Asn Asn Glu Ser Ser Glu Val Ile Val His
                485                 490                 495

Lys Ala Met Asp Ile Glu Tyr Asn Asp Met Phe Asn Asn Phe Thr Val
            500                 505                 510

Ser Phe Trp Leu Arg Val Pro Lys Val Ser Ala Ser His Leu Glu Gln
        515                 520                 525

Tyr Gly Thr Asn Glu Tyr Ser Ile Ile Ser Ser Met Lys Lys His Ser
    530                 535                 540

Leu Ser Ile Gly Ser Gly Trp Ser Val Ser Leu Lys Gly Asn Asn Leu
545                 550                 555                 560

Ile Trp Thr Leu Lys Asp Ser Ala Gly Glu Val Arg Gln Ile Thr Phe
                565                 570                 575

Arg Asp Leu Pro Asp Lys Phe Asn Ala Tyr Leu Ala Asn Lys Trp Val
            580                 585                 590

Phe Ile Thr Ile Thr Asn Asp Arg Leu Ser Ser Ala Asn Leu Tyr Ile
        595                 600                 605

Asn Gly Val Leu Met Gly Ser Ala Glu Ile Thr Gly Leu Gly Ala Ile
    610                 615                 620

Arg Glu Asp Asn Asn Ile Thr Leu Lys Leu Asp Arg Cys Asn Asn Asn
625                 630                 635                 640

Asn Gln Tyr Val Ser Ile Asp Lys Phe Arg Ile Phe Cys Lys Ala Leu
                645                 650                 655

Asn Pro Lys Glu Ile Glu Lys Leu Tyr Thr Ser Tyr Leu Ser Ile Thr
            660                 665                 670

Phe Leu Arg Asp Phe Trp Gly Asn Pro Leu Arg Tyr Asp Thr Glu Tyr
        675                 680                 685

Tyr Leu Ile Pro Val Ala Ser Ser Lys Asp Val Gln Leu Lys Asn
    690                 695                 700

Ile Thr Asp Tyr Met Tyr Leu Thr Asn Ala Pro Ser Tyr Thr Asn Gly
705                 710                 715                 720

Lys Leu Asn Ile Tyr Tyr Arg Arg Leu Tyr Asn Gly Leu Lys Phe Ile
                725                 730                 735

Ile Lys Arg Tyr Thr Pro Asn Asn Glu Ile Asp Ser Phe Val Lys Ser
            740                 745                 750

Gly Asp Phe Ile Lys Leu Tyr Val Ser Tyr Asn Asn Asn Glu His Ile
        755                 760                 765

Val Gly Tyr Pro Lys Asp Gly Asn Ala Phe Asn Asn Leu Asp Arg Ile
    770                 775                 780

Leu Arg Val Gly Tyr Asn Ala Pro Gly Ile Pro Leu Tyr Lys Lys Met
785                 790                 795                 800

Glu Ala Val Lys Leu Arg Asp Leu Lys Thr Tyr Ser Val Gln Leu Lys
                805                 810                 815

Leu Tyr Asp Asp Lys Asn Ala Ser Leu Gly Leu Val Gly Thr His Asn
```

```
            820                 825                 830
Gly Gln Ile Gly Asn Asp Pro Asn Arg Asp Ile Leu Ile Ala Ser Asn
            835                 840                 845

Trp Tyr Phe Asn His Leu Lys Asp Lys Ile Leu Gly Cys Asp Trp Tyr
        850                 855                 860

Phe Val Pro Thr Asp Glu Gly Trp Thr Asn Asp
865                 870                 875

<210> SEQ ID NO 26
<211> LENGTH: 15
<212> TYPE: PRT
<213> ORGANISM: Unknown
<220> FEATURE:
<223> OTHER INFORMATION: Description of Unknown: Universal
      T helper epitope peptide

<400> SEQUENCE: 26

Gln Tyr Ile Lys Ala Asn Ser Lys Phe Ile Gly Ile Thr Glu Leu
1               5                   10                  15

<210> SEQ ID NO 27
<211> LENGTH: 190
<212> TYPE: PRT
<213> ORGANISM: Human immunodeficiency virus 1

<400> SEQUENCE: 27

Glu Ile Cys Thr Glu Met Glu Lys Glu Gly Lys Ile Ser Lys Ile Gly
1               5                   10                  15

Pro Glu Asn Pro Tyr Asn Thr Pro Val Phe Ala Ile Lys Lys Lys Asp
            20                  25                  30

Ser Thr Lys Trp Arg Lys Leu Val Asp Phe Arg Glu Leu Asn Lys Arg
        35                  40                  45

Thr Gln Asp Phe Trp Glu Val Gln Leu Gly Ile Pro His Pro Ala Gly
    50                  55                  60

Leu Lys Lys Lys Lys Ser Val Thr Val Leu Asp Val Gly Asp Ala Tyr
65                  70                  75                  80

Phe Ser Val Pro Leu Asp Lys Asp Phe Arg Lys Tyr Thr Ala Phe Thr
                85                  90                  95

Ile Pro Ser Thr Asn Asn Glu Thr Pro Gly Ile Arg Tyr Gln Tyr Asn
            100                 105                 110

Val Leu Pro Gln Gly Trp Lys Gly Ser Pro Ala Ile Phe Gln Ser Ser
        115                 120                 125

Met Thr Lys Ile Leu Glu Pro Phe Arg Lys Gln Asn Pro Glu Ile Val
    130                 135                 140

Ile Tyr Gln Tyr Met Asp Asp Leu Tyr Ile Gly Ser Asp Leu Glu Ile
145                 150                 155                 160

Gly Gln His Arg Thr Lys Ile Glu Glu Leu Arg Gln His Leu Leu Lys
                165                 170                 175

Trp Gly Leu Thr Thr Pro Asp Lys Lys His Gln Lys Glu Pro
            180                 185                 190

<210> SEQ ID NO 28
<211> LENGTH: 20
<212> TYPE: PRT
<213> ORGANISM: Unknown
<220> FEATURE:
<223> OTHER INFORMATION: Description of Unknown: Universal T
      helper epitope peptide

<400> SEQUENCE: 28
```

Phe Arg Lys Gln Asn Pro Asp Ile Val Ile Tyr Gln Tyr Met Asp Asp
1               5                   10                  15

Leu Tyr Val Gly
            20

<210> SEQ ID NO 29
<211> LENGTH: 236
<212> TYPE: PRT
<213> ORGANISM: Human immunodeficiency virus 1

<400> SEQUENCE: 29

Trp Asp Arg Leu His Pro Ala Gln Ala Gly Pro Ile Ala Pro Gly Gln
1               5                   10                  15

Ile Arg Glu Pro Arg Gly Ser Asp Ile Ala Gly Thr Thr Ser Thr Leu
            20                  25                  30

Gln Glu Gln Ile Thr Trp Met Thr Asn Asn Pro Pro Ile Pro Val Gly
        35                  40                  45

Glu Ile Tyr Lys Arg Trp Ile Ile Leu Gly Leu Asn Lys Ile Val Arg
    50                  55                  60

Met Tyr Ser Pro Val Ser Ile Leu Asp Ile Lys Gln Gly Pro Lys Glu
65                  70                  75                  80

Pro Phe Arg Asp Tyr Val Asp Arg Phe Phe Lys Ala Leu Arg Ala Glu
                85                  90                  95

Gln Ala Thr Gln Asp Val Lys Asn Trp Met Thr Asp Thr Leu Leu Val
            100                 105                 110

Gln Asn Ala Asn Pro Asp Cys Lys Ser Ile Leu Arg Gly Leu Gly Pro
        115                 120                 125

Gly Ala Ser Leu Glu Glu Met Met Thr Ala Cys Gln Gly Val Gly Gly
    130                 135                 140

Pro Ser His Lys Ala Arg Val Leu Ala Glu Ala Met Ser Gln Ala Asn
145                 150                 155                 160

Ser Val Asn Met Met Gln Arg Ser Asn Phe Lys Gly Pro Lys Arg Thr
                165                 170                 175

Val Lys Cys Phe Asn Cys Gly Lys Glu Gly His Ile Ala Arg Asn Cys
            180                 185                 190

Arg Ala Pro Arg Lys Lys Gly Cys Trp Lys Cys Gly Gln Glu Gly His
        195                 200                 205

Gln Met Lys Asp Cys Thr Glu Arg Gln Ala Asn Phe Leu Gly Lys Ile
    210                 215                 220

Trp Pro Ser His Lys Gly Arg Pro Gly Asn Phe Leu
225                 230                 235

<210> SEQ ID NO 30
<211> LENGTH: 110
<212> TYPE: PRT
<213> ORGANISM: Homo sapiens

<400> SEQUENCE: 30

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

```
Gln Val Glu Leu Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
            100                 105                 110

<210> SEQ ID NO 31
<211> LENGTH: 585
<212> TYPE: PRT
<213> ORGANISM: Homo sapiens

<400> SEQUENCE: 31

Met Ala Ser Pro Gly Ser Gly Phe Trp Ser Phe Gly Ser Glu Asp Gly
 1               5                  10                  15

Ser Gly Asp Ser Glu Asn Pro Gly Thr Ala Arg Ala Trp Cys Gln Val
             20                  25                  30

Ala Gln Lys Phe Thr Gly Gly Ile Gly Asn Lys Leu Cys Ala Leu Leu
         35                  40                  45

Tyr Gly Asp Ala Glu Lys Pro Ala Glu Ser Gly Gly Ser Gln Pro Pro
 50                  55                  60

Arg Ala Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
                 85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
```

```
                        325                 330                 335
Gly Thr Thr Val Tyr Gly Ala Phe Asp Pro Leu Leu Ala Val Ala Asp
            340                 345                 350
Ile Cys Lys Lys Tyr Lys Ile Trp Met His Val Asp Ala Ala Trp Gly
            355                 360                 365
Gly Gly Leu Leu Met Ser Arg Lys His Lys Trp Lys Leu Ser Gly Val
            370                 375                 380
Glu Arg Ala Asn Ser Val Thr Trp Asn Pro His Lys Met Met Gly Val
385                 390                 395                 400
Pro Leu Gln Cys Ser Ala Leu Leu Val Arg Glu Glu Gly Leu Met Gln
                405                 410                 415
Asn Cys Asn Gln Met His Ala Ser Tyr Leu Phe Gln Gln Asp Lys His
                420                 425                 430
Tyr Asp Leu Ser Tyr Asp Thr Gly Asp Lys Ala Leu Gln Cys Gly Arg
                435                 440                 445
His Val Asp Val Phe Lys Leu Trp Leu Met Trp Arg Ala Lys Gly Thr
            450                 455                 460
Thr Gly Phe Glu Ala His Val Asp Lys Cys Leu Glu Leu Ala Glu Tyr
465                 470                 475                 480
Leu Tyr Asn Ile Ile Lys Asn Arg Glu Gly Tyr Glu Met Val Phe Asp
                485                 490                 495
Gly Lys Pro Gln His Thr Asn Val Cys Phe Trp Tyr Ile Pro Pro Ser
            500                 505                 510
Leu Arg Thr Leu Glu Asp Asn Glu Glu Arg Met Ser Arg Leu Ser Lys
            515                 520                 525
Val Ala Pro Val Ile Lys Ala Arg Met Met Glu Tyr Gly Thr Thr Met
            530                 535                 540
Val Ser Tyr Gln Pro Leu Gly Asp Lys Val Asn Phe Phe Arg Met Val
545                 550                 555                 560
Ile Ser Asn Pro Ala Ala Thr His Gln Asp Ile Asp Phe Leu Ile Glu
                565                 570                 575
Glu Ile Glu Arg Leu Gly Gln Asp Leu
            580                 585

<210> SEQ ID NO 32
<211> LENGTH: 74
<212> TYPE: PRT
<213> ORGANISM: Unknown
<220> FEATURE:
<223> OTHER INFORMATION: Description of Unknown: Composite self
      epitope Insulin-GAD peptide
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (37)..(40)
<223> OTHER INFORMATION: Any amino acid
<220> FEATURE:
<221> NAME/KEY: MOD_RES
<222> LOCATION: (56)..(59)
<223> OTHER INFORMATION: Any amino acid

<400> SEQUENCE: 32

Cys Gly Ser His Leu Val Glu Ala Leu Tyr Leu Val Cys Gly Glu Arg
1               5                   10                  15

Gly Xaa Xaa Xaa Xaa Pro Arg Leu Ile Ala Phe Thr Ser Glu His Ser
            20                  25                  30
```

```
His Phe Ser Leu Xaa Xaa Xaa Leu Tyr Asn Ile Ile Lys Asn Arg
            35              40                  45

Glu Gly Tyr Glu Met Val Phe Xaa Xaa Xaa Xaa Pro Ser Leu Arg Thr
 50                  55                  60

Leu Glu Asp Asn Glu Glu Arg Met Ser Arg
 65                  70

<210> SEQ ID NO 33
<211> LENGTH: 54
<212> TYPE: PRT
<213> ORGANISM: Unknown
<220> FEATURE:
<223> OTHER INFORMATION: Description of Unknown: Composite non-self
      epitope Tetanus-gp100, MART-1, TRP-2 peptide
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (29)..(32)
<223> OTHER INFORMATION: Any amino acid
<220> FEATURE:
<221> NAME/KEY: MOD_RES
<222> LOCATION: (42)..(45)
<223> OTHER INFORMATION: Any amino acid

<400> SEQUENCE: 33

Gln Tyr Ile Lys Ala Asn Ser Lys Phe Ile Gly Ile Thr Glu Leu Xaa
 1               5                  10                  15

Xaa Xaa Xaa Phe Leu Asp Gln Val Ala Phe Ser Val Xaa Xaa Xaa Xaa
                20                  25                  30

Ala Ala Gly Ile Gly Ile Leu Thr Val Xaa Xaa Xaa Xaa Ser Val Arg
            35                  40                  45

Asp Thr Leu Leu Gly Gly
         50

<210> SEQ ID NO 34
<211> LENGTH: 8
<212> TYPE: PRT
<213> ORGANISM: Unknown
<220> FEATURE:
<223> OTHER INFORMATION: Description of Unknown: MHC class
      I-restricted peptide

<400> SEQUENCE: 34

Ser Ile Ile Asn Phe Glu Lys Leu
 1               5

<210> SEQ ID NO 35
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Lys His Leu Trp Phe Phe Leu Leu Leu Val Ala Ala Pro Arg Trp
 1               5                  10                  15

Val Leu Ser Gln Val Gln Leu Gln
                20

<210> SEQ ID NO 36
<211> LENGTH: 9
<212> TYPE: PRT
```

<213> ORGANISM: Homo sapiens

<400> SEQUENCE: 36

Phe Leu Asp Gln Val Ala Phe Ser Val
1               5

<210> SEQ ID NO 37
<211> LENGTH: 9
<212> TYPE: PRT
<213> ORGANISM: Homo sapiens

<400> SEQUENCE: 37

Phe Leu Asp Gln Arg Val Phe Val Val
1               5

<210> SEQ ID NO 38
<211> LENGTH: 9
<212> TYPE: PRT
<213> ORGANISM: Homo sapiens

<400> SEQUENCE: 38

Phe Leu Phe Leu Trp Phe Phe Glu Val
1               5

<210> SEQ ID NO 39
<211> LENGTH: 661
<212> TYPE: PRT
<213> ORGANISM: Homo sapiens

<400> SEQUENCE: 39

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Phe Leu Asp Gln Val Ala Phe Ser Val Ser Val Ser Gln Leu Arg Ala
    210                 215                 220

```
Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
            245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
            290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
            325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
            355                 360                 365

Ala Glu Ser Thr Gly Met Thr Pro Glu Lys Val Pro Val Ser Glu Val
370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
            405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
            450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
            485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
            515                 520                 525

Ser Ser Pro Gly Cys Gln Pro Ala Gln Arg Leu Cys Gln Pro Val
            530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
            565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
            595                 600                 605

Val Val Leu Ala Ser Leu Ile Tyr Arg Arg Arg Leu Met Lys Gln Asp
            610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
```

Ser Gly Gln Gln Val
            660

<210> SEQ ID NO 40
<211> LENGTH: 661
<212> TYPE: PRT
<213> ORGANISM: Homo sapiens

<400> SEQUENCE: 40

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
        195                 200                 205

Phe Leu Asp Gln Arg Val Phe Val Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

```
Val Pro Thr Thr Glu Val Ile Ser Thr Ala Pro Val Gln Met Pro Thr
            355                 360                 365

Ala Glu Ser Thr Gly Met Thr Pro Glu Lys Val Pro Val Ser Glu Val
370                 375                 380

Met Gly Thr Thr Leu Ala Glu Met Ser Thr Pro Glu Ala Thr Gly Met
385                 390                 395                 400

Thr Pro Ala Glu Val Ser Ile Val Leu Ser Gly Thr Thr Ala Ala
            405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
            485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
            515                 520                 525

Ser Ser Pro Gly Cys Gln Pro Pro Ala Gln Arg Leu Cys Gln Pro Val
530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
            565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Val Leu Met Ala
            595                 600                 605

Val Val Leu Ala Ser Leu Ile Tyr Arg Arg Arg Leu Met Lys Gln Asp
            610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
            645                 650                 655

Ser Gly Gln Gln Val
            660

<210> SEQ ID NO 41
<211> LENGTH: 661
<212> TYPE: PRT
<213> ORGANISM: Homo sapiens

<400> SEQUENCE: 41

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
            50                  55                  60
```

```
Gln Val Ser Leu Lys Val Ser Asn Asp Gly Pro Thr Leu Ile Gly Ala
 65                  70                  75                  80

Asn Ala Ser Phe Ser Ile Ala Leu Asn Phe Pro Gly Ser Gln Lys Val
             85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Pro Cys Pro Ser Gly Ser Trp Ser
        130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Phe Leu Phe Leu Trp Phe Phe Glu Val Ser Val Ser Gln Leu Arg Ala
210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
            355                 360                 365

Ala Glu Ser Thr Gly Met Thr Pro Glu Lys Val Pro Val Ser Glu Val
            370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
                420                 425                 430

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
            450                 455                 460

Arg Leu Val Lys Arg Gln Val Pro Leu Asp Cys Val Leu Tyr Arg Tyr
465                 470                 475                 480
```

```
Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Ala Gln Arg Leu Cys Gln Pro Val
530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 42
<211> LENGTH: 9
<212> TYPE: PRT
<213> ORGANISM: Homo sapiens

<400> SEQUENCE: 42

Leu Leu Pro Gly Gly Arg Pro Tyr Arg
1               5

<210> SEQ ID NO 43
<211> LENGTH: 8
<212> TYPE: PRT
<213> ORGANISM: Homo sapiens

<400> SEQUENCE: 43

Ser Val Tyr Asp Phe Phe Val Trp
1               5

<210> SEQ ID NO 44
<211> LENGTH: 235
<212> TYPE: PRT
<213> ORGANISM: Homo sapiens

<400> SEQUENCE: 44

Met Ser Pro Leu Trp Trp Gly Phe Leu Leu Ser Cys Leu Gly Cys Lys
1               5                   10                  15

Ile Leu Pro Gly Ala Gln Gly Gln Phe Pro Arg Val Cys Met Thr Val
            20                  25                  30

Asp Ser Leu Val Asn Lys Glu Cys Cys Pro Arg Leu Gly Ala Glu Ser
        35                  40                  45

Ala Asn Val Cys Gly Ser Gln Gln Gly Arg Gly Gln Cys Thr Glu Val
    50                  55                  60

Arg Ala Asp Thr Arg Pro Trp Ser Gly Pro Tyr Ile Leu Arg Asn Gln
```

```
            65                  70                  75                  80
Asp Asp Arg Glu Leu Trp Pro Arg Lys Phe Phe His Arg Thr Cys Lys
                    85                  90                  95

Cys Thr Gly Asn Phe Ala Gly Tyr Asn Cys Gly Asp Cys Lys Phe Gly
                100                 105                 110

Trp Thr Gly Pro Asn Cys Glu Arg Lys Lys Pro Val Ile Arg Gln
                115                 120                 125

Asn Ile His Ser Leu Leu Pro Gly Gly Arg Pro Tyr Arg Leu Gly Ala
                130                 135                 140

Leu Asp Leu Ala Lys Lys Arg Val His Pro Asp Tyr Val Ile Thr Thr
145                 150                 155                 160

Gln His Trp Val Gly Leu Leu Gly Pro Asn Gly Thr Gln Pro Gln Phe
                    165                 170                 175

Ala Asn Cys Ser Val Tyr Asp Phe Phe Val Trp Leu His Tyr Ser Val
                180                 185                 190

Tyr Asp Phe Phe Val Trp Phe Phe Pro Trp Leu Lys Val Tyr Tyr Tyr
                    195                 200                 205

Arg Phe Val Ile Gly Leu Arg Val Trp Gln Trp Glu Val Ile Ser Cys
    210                 215                 220

Lys Leu Ile Lys Arg Ala Thr Thr Arg Gln Pro
225                 230                 235

<210> SEQ ID NO 45
<211> LENGTH: 146
<212> TYPE: PRT
<213> ORGANISM: Homo sapiens

<400> SEQUENCE: 45

Met Gly Phe Leu Arg Arg Leu Ile Tyr Arg Arg Pro Met Ile Tyr
1               5                   10                  15

Val Glu Ser Ser Glu Glu Ser Ser Asp Glu Gln Pro Asp Glu Val Glu
                    20                  25                  30

Ser Pro Thr Gln Ser Gln Asp Ser Thr Pro Ala Glu Glu Arg Glu Asp
                35                  40                  45

Glu Gly Ala Ser Ala Ala Gln Gly Gln Glu Pro Glu Ala Asp Ser Gln
    50                  55                  60

Glu Leu Val Gln Pro Lys Thr Gly Cys Glu Pro Gly Asp Gly Pro Asp
65                  70                  75                  80

Thr Lys Arg Val Cys Leu Arg Asn Glu Glu Gln Met Lys Leu Pro Ala
                    85                  90                  95

Glu Gly Pro Glu Pro Glu Ala Asp Ser Gln Glu Val His Pro Lys
                100                 105                 110

Thr Gly Cys Glu Arg Gly Asp Gly Pro Asp Val Gln Glu Leu Gly Leu
                115                 120                 125

Pro Asn Pro Glu Glu Val Lys Thr Pro Glu Glu Asp Glu Gly Gln Ser
                130                 135                 140

Gln Pro
145

<210> SEQ ID NO 46
<211> LENGTH: 339
<212> TYPE: PRT
<213> ORGANISM: Homo sapiens

<400> SEQUENCE: 46

Met Glu Ser Arg Lys Asp Ile Thr Asn Gln Glu Glu Leu Trp Lys Met
```

-continued

```
1               5                   10                  15
Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
                35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
                115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
        180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
        260                 265                 270

Ala Trp Asn Lys Trp Ile Asp Ile Lys Gln Phe Val Trp Tyr Thr Pro
            275                 280                 285

Pro Thr Phe Met Ile Ala Val Phe Leu Pro Ile Val Val Leu Ile Phe
    290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 47
<211> LENGTH: 102
<212> TYPE: PRT
<213> ORGANISM: Homo sapiens

<400> SEQUENCE: 47

Met Ser Ala Arg Val Arg Ser Arg Ser Arg Gly Arg Gly Asp Gly Gln
1               5                   10                  15

Glu Ala Pro Asp Val Val Ala Phe Val Ala Pro Gly Glu Ser Gln Gln
                20                  25                  30

Glu Glu Pro Pro Thr Asp Asn Gln Asp Ile Glu Pro Gly Gln Glu Arg
```

```
                    35                  40                  45
Glu Gly Thr Pro Pro Ile Glu Glu Arg Lys Val Glu Gly Asp Cys Gln
 50                  55                  60
Glu Met Asp Leu Glu Lys Thr Arg Ser Glu Arg Gly Asp Gly Ser Asp
 65                  70                  75                  80
Val Lys Glu Lys Thr Pro Pro Asn Pro Lys His Ala Lys Thr Lys Glu
                 85                  90                  95
Ala Gly Asp Gly Gln Pro
                100

<210> SEQ ID NO 48
<211> LENGTH: 1255
<212> TYPE: PRT
<213> ORGANISM: Homo sapiens

<400> SEQUENCE: 48

Met Thr Pro Gly Thr Gln Ser Pro Phe Phe Leu Leu Leu Leu Leu Thr
 1               5                  10                  15
Val Leu Thr Val Val Thr Gly Ser Gly His Ala Ser Ser Thr Pro Gly
                20                  25                  30
Gly Glu Lys Glu Thr Ser Ala Thr Gln Arg Ser Ser Val Pro Ser Ser
                35                  40                  45
Thr Glu Lys Asn Ala Val Ser Met Thr Ser Ser Val Leu Ser Ser His
 50                  55                  60
Ser Pro Gly Ser Gly Ser Ser Thr Thr Gln Gly Gln Asp Val Thr Leu
 65                  70                  75                  80
Ala Pro Ala Thr Glu Pro Ala Ser Gly Ser Ala Ala Thr Trp Gly Gln
                85                  90                  95
Asp Val Thr Ser Val Pro Val Thr Arg Pro Ala Leu Gly Ser Thr Thr
                100                 105                 110
Pro Pro Ala His Asp Val Thr Ser Ala Pro Asp Asn Lys Pro Ala Pro
                115                 120                 125
Gly Ser Thr Ala Pro Pro Ala His Gly Val Thr Ser Ala Pro Asp Thr
                130                 135                 140
Arg Pro Ala Pro Gly Ser Thr Ala Pro Ala His Gly Val Thr Ser
145                 150                 155                 160
Ala Pro Asp Thr Arg Pro Ala Pro Gly Ser Thr Ala Pro Pro Ala His
                165                 170                 175
Gly Val Thr Ser Ala Pro Asp Thr Arg Pro Ala Pro Gly Ser Thr Ala
                180                 185                 190
Pro Pro Ala His Gly Val Thr Ser Ala Pro Asp Thr Arg Pro Ala Pro
                195                 200                 205
Gly Ser Thr Ala Pro Pro Ala His Gly Val Thr Ser Ala Pro Asp Thr
                210                 215                 220
Arg Pro Ala Pro Gly Ser Thr Ala Pro Pro Ala His Gly Val Thr Ser
225                 230                 235                 240
Ala Pro Asp Thr Arg Pro Ala Pro Gly Ser Thr Ala Pro Pro Ala His
                245                 250                 255
Gly Val Thr Ser Ala Pro Asp Thr Arg Pro Ala Pro Gly Ser Thr Ala
                260                 265                 270
Pro Pro Ala His Gly Val Thr Ser Ala Pro Asp Thr Arg Pro Ala Pro
                275                 280                 285
Gly Ser Thr Ala Pro Pro Ala His Gly Val Thr Ser Ala Pro Asp Thr
                290                 295                 300
```

```
Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
            325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
            405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
            435                 440                 445

Gly Ser Thr Ala Pro Pro Ala His Gly Val Thr Ser Ala Pro Asp Thr
450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
            485                 490                 495

Gly Val Thr Ser Ala Pro Asp Thr Arg Pro Ala Pro Gly Ser Thr Ala
                500                 505                 510

Pro Pro Ala His Gly Val Thr Ser Ala Pro Asp Thr Arg Pro Ala Pro
            515                 520                 525

Gly Ser Thr Ala Pro Pro Ala His Gly Val Thr Ser Ala Pro Asp Thr
530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
            565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
            595                 600                 605

Gly Ser Thr Ala Pro Pro Ala His Gly Val Thr Ser Ala Pro Asp Thr
610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
            645                 650                 655

Gly Val Thr Ser Ala Pro Asp Thr Arg Pro Ala Pro Gly Ser Thr Ala
                660                 665                 670

Pro Pro Ala His Gly Val Thr Ser Ala Pro Asp Thr Arg Pro Ala Pro
            675                 680                 685

Gly Ser Thr Ala Pro Pro Ala His Gly Val Thr Ser Ala Pro Asp Thr
690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
```

```
                        725                 730                 735
Gly Val Thr Ser Ala Pro Asp Thr Arg Pro Ala Pro Gly Ser Thr Ala
                    740                 745                 750
Pro Pro Ala His Gly Val Thr Ser Ala Pro Asp Thr Arg Pro Ala Pro
                755                 760                 765
Gly Ser Thr Ala Pro Pro Ala His Gly Val Thr Ser Ala Pro Asp Thr
            770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                805                 810                 815
Gly Val Thr Ser Ala Pro Asp Thr Arg Pro Ala Pro Gly Ser Thr Ala
                820                 825                 830
Pro Pro Ala His Gly Val Thr Ser Ala Pro Asp Thr Arg Pro Ala Pro
                835                 840                 845
Gly Ser Thr Ala Pro Pro Ala His Gly Val Thr Ser Ala Pro Asp Thr
            850                 855                 860
Arg Pro Ala Pro Gly Ser Thr Ala Pro Pro Ala His Gly Val Thr Ser
865                 870                 875                 880
Ala Pro Asp Thr Arg Pro Ala Pro Gly Ser Thr Ala Pro Pro Ala His
                885                 890                 895
Gly Val Thr Ser Ala Pro Asp Thr Arg Pro Ala Pro Gly Ser Thr Ala
                900                 905                 910
Pro Pro Ala His Gly Val Thr Ser Ala Pro Thr Arg Pro Ala Pro
                915                 920                 925
Gly Ser Thr Ala Pro Pro Ala His Gly Val Thr Ser Ala Pro Asp Asn
                930                 935                 940
Arg Pro Ala Leu Gly Ser Thr Ala Pro Pro Val His Asn Val Thr Ser
945                 950                 955                 960
Ala Ser Gly Ser Ala Ser Gly Ser Ala Ser Thr Leu Val His Asn Gly
                965                 970                 975
Thr Ser Ala Arg Ala Thr Thr Thr Pro Ala Ser Lys Ser Thr Pro Phe
            980                 985                 990
Ser Ile Pro Ser His His Ser Asp Thr Pro Thr Thr Leu Ala Ser His
        995                 1000                1005
Ser Thr Lys Thr Asp Ala Ser Ser Thr His His Ser Ser Val Pro
    1010                1015                1020
Pro Leu Thr Ser Ser Asn His Ser Thr Ser Pro Gln Leu Ser Thr
    1025                1030                1035
Gly Val Ser Phe Phe Phe Leu Ser Phe His Ile Ser Asn Leu Gln
    1040                1045                1050
Phe Asn Ser Ser Leu Glu Asp Pro Ser Thr Asp Tyr Tyr Gln Glu
    1055                1060                1065
Leu Gln Arg Asp Ile Ser Glu Met Phe Leu Gln Ile Tyr Lys Gln
    1070                1075                1080
Gly Gly Phe Leu Gly Leu Ser Asn Ile Lys Phe Arg Pro Gly Ser
    1085                1090                1095
Val Val Val Gln Leu Thr Leu Ala Phe Arg Glu Gly Thr Ile Asn
    1100                1105                1110
Val His Asp Val Glu Thr Gln Phe Asn Gln Tyr Lys Thr Glu Ala
    1115                1120                1125
Ala Ser Arg Tyr Asn Leu Thr Ile Ser Asp Val Ser Val Ser Asp
    1130                1135                1140
```

```
Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Ala Ser Ala Asn Leu
    1250                1255

<210> SEQ ID NO 49
<211> LENGTH: 263
<212> TYPE: PRT
<213> ORGANISM: Ovine respiratory syncytial virus

<400> SEQUENCE: 49

Met Ser Asn His Thr His His Phe Glu Phe Lys Thr Leu Lys Lys Ala
1               5                   10                  15

Trp Lys Ala Ser Lys Tyr Phe Ile Val Gly Leu Ser Cys Leu Tyr Lys
                20                  25                  30

Leu Asn Leu Lys Ser Leu Val Gln Met Ala Leu Ser Ala Leu Ala Met
            35                  40                  45

Ile Thr Leu Val Ser Leu Thr Ile Thr Ala Ile Ile Tyr Ile Ser Thr
        50                  55                  60

Gly Asn Thr Lys Ala Lys Pro Met Pro Thr Pro Thr Ile Gln Ile Thr
65                  70                  75                  80

Gln Gln Phe Gln Asn His Thr Ser Leu Pro Pro Thr Glu His Asn His
                85                  90                  95

Asn Ser Thr His Ser Pro Thr Gln Gly Thr Thr Ser Pro His Thr Phe
            100                 105                 110

Ala Val Asp Val Thr Glu Gly Thr Arg Tyr Tyr His Leu Thr Leu Lys
        115                 120                 125

Thr Gln Gly Gly Lys Thr Lys Gly Pro Pro Thr Pro His Ala Thr Arg
    130                 135                 140

Lys Pro Pro Ile Ser Ser Gln Lys Ser Asn Pro Ser Glu Ile Gln Gln
145                 150                 155                 160

Asp Tyr Ser Asp Phe Gln Ile Leu Pro Tyr Val Pro Cys Asn Ile Cys
                165                 170                 175

Glu Gly Asp Ser Ala Cys Leu Ser Leu Cys Gln Asp Arg Ser Glu Ser
            180                 185                 190

Ile Leu Asp Lys Ala Leu Thr Thr Thr Pro Lys Lys Thr Pro Lys Pro
        195                 200                 205

Met Thr Thr Lys Lys Pro Thr Lys Thr Ser Thr His Ile Arg Thr Ser
    210                 215                 220

Leu Arg Asn Lys Leu Tyr Ile Lys Thr Asn Met Thr Thr Pro His
225                 230                 235                 240

Gly Leu Ile Ser Thr Ala Lys His Asn Lys Asn Gln Ser Thr Val Gln
```

-continued

```
                245                 250                 255
Asn Pro Arg His Thr Leu Ala
            260

<210> SEQ ID NO 50
<211> LENGTH: 192
<212> TYPE: PRT
<213> ORGANISM: Human respiratory syncytial virus

<400> SEQUENCE: 50

Ala Thr Asp Gln Ile Lys Asn Thr Thr Pro Thr Tyr Leu Thr Gln Asn
1               5                   10                  15

Pro Gln Leu Gly Ile Ser Phe Ser Asn Leu Ser Glu Thr Thr Ser Gln
            20                  25                  30

Pro Thr Thr Ile Leu Ala Ser Thr Thr Pro Ser Ala Glu Ser Thr Pro
        35                  40                  45

Gln Ser Thr Thr Val Lys Ile Lys Asn Thr Thr Thr Thr Gln Ile Gln
    50                  55                  60

Pro Ser Lys Pro Thr Thr Lys Gln Arg Gln Asn Lys Pro Gln Asn Lys
65                  70                  75                  80

Pro Asn Asn Asp Phe His Phe Glu Val Phe Asn Phe Val Pro Cys Ser
                85                  90                  95

Ile Cys Ser Asn Asn Pro Thr Cys Trp Ala Ile Cys Lys Arg Ile Pro
            100                 105                 110

Asn Lys Lys Pro Gly Lys Lys Thr Thr Thr Lys Pro Thr Lys Lys Pro
        115                 120                 125

Thr Ile Lys Thr Thr Lys Lys Asp Pro Lys Pro Gln Thr Thr Lys Pro
    130                 135                 140

Lys Glu Val Leu Thr Thr Lys Pro Thr Glu Lys Pro Thr Ile Ser Thr
145                 150                 155                 160

Thr Lys Thr Asn Ile Arg Thr Thr Leu Leu Thr Ser Asn Thr Thr Gly
                165                 170                 175

Asn Pro Glu His Thr Ser Gln Lys Gly Asn Pro Pro Leu Asn His Leu
            180                 185                 190

<210> SEQ ID NO 51
<211> LENGTH: 94
<212> TYPE: PRT
<213> ORGANISM: Human herpes virus 1

<400> SEQUENCE: 51

Thr Pro Pro Met Pro Ser Ile Gly Leu Glu Glu Glu Glu Glu Glu Glu
1               5                   10                  15

Gly Ala Gly Asp Gly Glu His Leu Glu Gly Gly Asp Gly Thr Arg Asp
            20                  25                  30

Thr Leu Pro Gln Ser Pro Gly Pro Ala Phe Pro Leu Ala Glu Asp Val
        35                  40                  45

Glu Lys Asp Lys Pro Asn Arg Pro Val Val Pro Ser Pro Asp Pro Asn
    50                  55                  60

Asn Ser Pro Ala Arg Pro Glu Thr Ser Arg Pro Lys Thr Pro Pro Thr
65                  70                  75                  80

Ile Ile Gly Pro Leu Ala Thr Arg Pro Thr Thr Arg Leu Thr
                85                  90

<210> SEQ ID NO 52
<211> LENGTH: 14
<212> TYPE: PRT
```

-continued

```
<213> ORGANISM: Human herpes virus 1

<400> SEQUENCE: 52

Met Ser Trp Ala Leu Glu Met Ala Asp Thr Phe Leu Asp Thr
1               5                   10

<210> SEQ ID NO 53
<211> LENGTH: 261
<212> TYPE: PRT
<213> ORGANISM: Human herpes virus 2

<400> SEQUENCE: 53

Met Ser Arg Arg Arg Gly Pro Arg Arg Arg Gly Pro Arg Arg Arg Pro
1               5                   10                  15

Arg Pro Gly Ala Pro Ala Val Pro Arg Pro Gly Ala Pro Ala Val Pro
            20                  25                  30

Arg Pro Gly Ala Leu Pro Thr Ala Asp Ser Gln Met Val Pro Ala Tyr
        35                  40                  45

Asp Ser Gly Thr Ala Val Glu Ser Ala Pro Ala Ala Ser Ser Leu Leu
    50                  55                  60

Arg Arg Trp Leu Leu Val Pro Gln Ala Asp Asp Ser Asp Asp Ala Asp
65                  70                  75                  80

Tyr Ala Gly Asn Asp Asp Ala Glu Trp Ala Asn Ser Pro Pro Ser Glu
                85                  90                  95

Gly Gly Gly Lys Ala Pro Glu Ala Pro His Ala Ala Pro Ala Ala Ala
            100                 105                 110

Cys Pro Pro Pro Pro Pro Arg Lys Glu Arg Gly Pro Gln Arg Pro Leu
        115                 120                 125

Pro Pro His Leu Ala Leu Arg Leu Arg Thr Thr Thr Glu Tyr Leu Ala
    130                 135                 140

Arg Leu Ser Leu Arg Arg Arg Arg Pro Pro Ala Ser Pro Pro Ala Asp
145                 150                 155                 160

Ala Pro Arg Gly Lys Val Cys Phe Ser Pro Arg Val Gln Val Arg His
                165                 170                 175

Leu Val Ala Trp Glu Thr Ala Ala Arg Leu Ala Arg Arg Gly Ser Trp
            180                 185                 190

Ala Arg Glu Arg Ala Asp Arg Asp Arg Phe Arg Arg Arg Val Ala Ala
        195                 200                 205

Ala Glu Ala Val Ile Gly Pro Cys Leu Glu Pro Glu Ala Arg Ala Arg
    210                 215                 220

Ala Arg Ala Arg Ala Arg Ala His Glu Asp Gly Gly Pro Ala Glu Glu
225                 230                 235                 240

Glu Glu Ala Ala Ala Ala Ala Arg Gly Ser Ser Ala Ala Ala Gly Pro
                245                 250                 255

Gly Arg Arg Ala Val
            260
```